US011273161B2

(12) United States Patent
Madison et al.

(10) Patent No.: US 11,273,161 B2
(45) Date of Patent: Mar. 15, 2022

(54) METHODS OF TREATING AUTISM SPECTRUM DISORDERS

(71) Applicant: The Broad Institute, Inc., Cambridge, MA (US)

(72) Inventors: Jon Madison, Cambridge, MA (US); Jeffrey Cottrell, Cambridge, MA (US)

(73) Assignee: The Broad Institute, Inc., Cambridge, MA (US)

(*) Notice: Subject to any disclaimer, the term of this patent is extended or adjusted under 35 U.S.C. 154(b) by 0 days.

(21) Appl. No.: 16/438,790

(22) Filed: Jun. 12, 2019

(65) Prior Publication Data

US 2020/0009149 A1 Jan. 9, 2020

Related U.S. Application Data

(63) Continuation of application No. PCT/US2017/067099, filed on Dec. 18, 2017.

(60) Provisional application No. 62/582,472, filed on Nov. 7, 2017, provisional application No. 62/559,765, filed on Sep. 18, 2017, provisional application No. 62/435,986, filed on Dec. 19, 2016.

(51) Int. Cl.
| | |
|---|---|
| *A61K 31/52* | (2006.01) |
| *A61K 31/198* | (2006.01) |
| *A61K 31/7105* | (2006.01) |
| *C12N 15/113* | (2010.01) |
| *C12N 15/52* | (2006.01) |

(52) U.S. Cl.
CPC ............ *A61K 31/52* (2013.01); *A61K 31/198* (2013.01); *A61K 31/7105* (2013.01); *C12N 15/113* (2013.01); *C12N 15/52* (2013.01); *C12N 2310/11* (2013.01); *C12Y 403/02002* (2013.01)

(58) Field of Classification Search
CPC ....... A61K 31/198; A61K 31/52; A61P 25/00; A61P 25/28
See application file for complete search history.

(56) References Cited

U.S. PATENT DOCUMENTS

| 6,027,889 A | 2/2000 | Barany et al. | |
|---|---|---|---|
| 6,214,571 B1 * | 4/2001 | Carrera ................ | A61K 31/198 435/15 |
| 2003/0119004 A1 | 6/2003 | Wenz et al. | |
| 2015/0051288 A1 | 2/2015 | Talalay et al. | |
| 2015/0126496 A1 | 5/2015 | Page et al. | |
| 2015/0224164 A1 | 8/2015 | Glass et al. | |

FOREIGN PATENT DOCUMENTS

| EP | 0332435 A2 | 9/1989 |
|---|---|---|
| WO | 1992007569 A1 | 5/1992 |
| WO | 2001092579 A2 | 12/2001 |
| WO | 2009023495 A2 | 2/2009 |

OTHER PUBLICATIONS

Van Den Berghe et al., Progress in Neurobiology, 1992, 39, p. 547-561. (Year: 1992).*
Camici et al., Neurochemistry International, 2010, 56, p. 367-378. (Year: 2010).*
Ye et al. "Fluorescent microsphere-based readout technology for multiplexed human single nucleotide polymorphism analysis and bacterial identification" Human Mutation, 17(4): 305-316 (2001).
Camici et al., "Pediatric neurological syndromes and inborn errors of purine metabolism," Neurochemistry International, 56: 367-378 (2010).
Carielle et al. "Resolution of a Missense Mutant in Human Genomic DNA by Denaturing Gradient Gel Electrophoresis and Direct Sequencing Using In Vitro DNA Amplification: HPRTMunich," American Journal of Human Genetics 42: 726-734(1988).
Casey et al. "Inhibition of adenylosuccinate by L-Alanosyl-5-Aminoimidazole-4-Carboxylic Acid Ribonucleotide (Alanosyl-Aicor)," Biochemical Pharmacology, 36(5): 705-709 (1987).
Chen et al., "A Microsphere-Based Assay for Multiplexed Single Nucleotide Polymorphism Analysis Using Single Base Chain Extension," Genome Research, 10: 549-557 (2000).
Cotton et al., "Reactivity of cytosine and thymine in single-base-pair mismatches with hydroxylamine and osmium tetroxide and its application to the study of mutations," 85(12): 4397-4401 (1988).
Crowther et al., "Identification of inhibitors for putative malaria drug targets among novel antimalarial compounds," Molecular & Biochemical Parasitology, 175:21-29 (2011).
De La Vega et al., New Generation Pharmacogenomic Tools: A SNP Linkage Disequilibrium Map, Validated SMP Assay Resource, and High-Throughput Instrumentation System for Large-Scale Genetic Studies, BioTechniques, 32: S48-S 54 (2002).
Donti et al., "Diagnosis of adenylosuccinate lyase deficiency by metabolomic profiling in plasma reveals a phenotypic spectrum," Molecular Genetics and Metabolism Reports, 8: 61-66 (2016).
Escamilla et al., "Kctd13 deletion reduces synaptic transmission via increased RhoA," Nautre,551(7679):227-231 (2017).
Faham et al., "Mismatch repair detection (MRD): high-throughput scanning for DNA variations," Human Molecular Genetics, 10(6): 1657-1664 (2001).
Faham et al., "Multiplexed variation scanning for 1,000 amplicons in hundreds of patients using mismatch repair detection (MRD) on tag arrays," Proceeding of the National Academy of Sciences, UDS, 102(41): 14717-14722 (2005).
Fan et al., "Parallel Genotyping of Human SNPs Using Generic High-density Oligonucleotide Tag Arrays," Genome Res, 10(6): 853-860 (2000).
Grossman et al., "High-density multiplex detection of nucleic acid sequences: oligonucleotide ligation assay and sequence-coded separation," Nuc. Acids Res. 22(21): 4527-4534 (1994).
Hanessian et al., "An Enzyme-Bound Bisubstrate Hybrid Inhibitor of Adenylosuccinate Synthetase," Anged. Chem. Int. Ed. 38(21): 3159-3162 (1999).

(Continued)

*Primary Examiner* — Jonathan S Lau
(74) *Attorney, Agent, or Firm* — McNeill Baur PLLC

(57) ABSTRACT

Methods of diagnosing and treating autism spectrum disorders are provided.

7 Claims, 26 Drawing Sheets

Specification includes a Sequence Listing.

(56) References Cited

OTHER PUBLICATIONS

Jacquemont et al., "Mirror extreme BMI phenotypes associated with gene dosage at the chromosome 16p11.2 locus," Mature, 478(7367): 97-102 (2011).

Jaeken et al., "Adenylosuccinase deficiency: a newly recognized variant," J. Inherit. Metab. Dis.15: 416-418 (1992).

Jurecka et al., "Adenylosuccinate lyase deficiency," J Inherit Metab Dis, 38:231-242 (2015).

Kumar et al., "Recurrent 16p11.2 microdeletions in autism," Hum. Mol. Genet. 17: 628-638 (2008).

Lin et al. "Spatiotemporal 16p11.2 Protein Network Implicates Cortical Late Mid-Fetal Brain Development and KCTD13-Cul3-RhoA Pathway in Psychiatric Diseases," Neuron, 85: 742-754 (2015).

Marshall et al., "Structural Variation of Chromosomes in Autism Spectrum Disorder," The American Journal of Human Genetics 82:477-488 (2008).

McClay et al., "High-Throughput Single-Nucleotide Polymorphism Genotyping by Fluorescent Competitive Allele-Specific Polymerase Chain Reaction (SNiPTag)," Analytical Biochemistry, 301: 200-206 (2002).

Mhlanga et al., "Using molecular beacons to detect single-nucleotide polymorphisms with real-time PCR" Methods 25: 463-471 (2001).

Mihaylova et al., "The AMP-activated protein kinase (AMPK) signaling pathway coordinates cell growth, autophagy, & metabolism," 13(9): 1016-1023 (2012).

Myers et al. "Detection of single base substitutions in total genomic DNA" Nature, 313: 495-498 (1985).

Myers et al., "Detection of single base substitutions by ribonuclease cleavage at mismatches in RNA:DNA duplexes" Science 230: 1242-1246 (1985).

Naldini, Gene therapy returns to centre stage, Nature, 526: 351-360 (2015).

Naviaux et al., "Low-dose suramin in autism spectrum disorder: a small, phase I/II, randomized clinical trial," Annals of Clinical and Translational Neurology, 4(7):491-505 (2017).

Newton et al., "Analysis of any point mutation in DNA. The amplification refractory mutation system (ARMS)" Nucleic Acids Research, 17(7): 2503-25106 (1989).

Orita et al., "Detection of polymorphisms of human DNA by gel electrophoresis as single-strand conformation polymorphisms," Proceedings of the National Academy of Sciences, USA, 86: 2766-2770 (1989).

Orita et al., "Rapid and sensitive detection of point mutations and DNA polymorphisms using the polymerase chain reaction" Genomics, 5: 874-879 (1989).

Page et al., "Purine metabolism abnormalities in a hyperuricosuric subclass of autism," Biochemica et Biophysica Acta, 1500: 291-296 (2000).

Pastinen et al., "Minisequencing: A Specific Tool for DNA Analysis and Diagnostics on Oligonucleotide Arrays," Genome Res 7(6): 606-614 (1997).

PCT, International Search Report and Written Opinion for PCTUS201767099, dated May 15, 2018.

Ranade et al., "High-Throughput Genotyping with Single Nucleotide Polymorphisms" Genome Res. 30(6): 1262-1268 (2001).

Ruano et al., "Direct haplotyping of chromosomal segments from multiple heterozygotes via allele-specific PCR amplification" Nucleic Acids Research 17(20): 8392 (1989).

Salerno et al., "Succinylpurinemic autism: increased sensitivity of defective adenylosuccinate lyase towards 4-hydroxy-2-nonenal," Biochemica et Biophysica Acta, 1500: 335-341 (2000).

Sanders et al., "Insights into Autism Spectrum Disorder Genomic Architecture and Biology from 71 Risk Loci," 87(6): 1215-1233 (2015).

Sheng et al., "The Regulation and Function of c-fos and Other Immediate Early Genes in the Nervous System." Neuron, 4: 477-485 (1990).

Shenk et al., "Biochemical method for mapping mutational alterations in DNA with S1 nuclease: the location of deletions and temperature-sensitive mutations in simian virus 40," Proceedings of the National Academy, USA, 72(3): 989-993(1975).

Shi, "Enabling large-scale pharmacogenetic studies by high-throughput mutation detection and genotyping technologies," Clin. Chem. 47(2): 164-172 (2001).

Stenesen et al., "Dietary adenine controls adult lifespan via adenosine nucleotide biosynthesis and AMPK, and regulates the longevity benefit of caloric restriction" Cell Metabolism, 17(1): 101-12 (2013).

Sztainberg et al., "Reversal of phenotypes in MECP2 duplication mice using genetic rescue or antisense oligonucleotides," Nature, 528: 123-126 (2015).

Tibrewal et al., "Evaluation of hadacidin analogues," Bioorganic & Medicinal Chemistry Letters, 21: 517-519 (2011).

Tyagi et al. "Multicolor molecular beacons for allele discrimination" Nature Biotechnology, 16: 49-53 (1998).

Tyagi, et al., "Identification of the Antimetabolite of L-Alanosine, L-Alanosyl-5-Amino-4-Imidazolecarboxylic Acid Ribonucleotide, in Tumors and Assessment of Its Inhibition of Adenylosuccinate Synthetase," Cancer Research, 40 (12):4390-4397 (1980).

Van Den Berghe et al., "The Purine Nucleotide Cycle and Its Molecular Defects," Progress in Neurobiology, 39: 547-561 (1992).

Van Werkhoven et al., "Early disgnosis of adenylosuccinate lyase deficiency using a high-throughput screening method and a trial of oral S-adenosyl-L-Methionine as a treatment method," Developmental Medicine and Child Neurology, 55(11): 1060-1064 (2013).

Weiss ete al., "Association between Microdeletion and Microduplication at 16p11.2 and Autism," The New England Journal of Medicine, 358(7): 667-675 (2008).

Winter et al., "A method to detect and characterize point mutations in transcribed genes: amplification and overexpression of the mutant c-Ki-ras allele in human tumor cells" Proceedings of the National Academy of Sciences, USA, 82(22): 7575 (1985).

Wu et al., "The ligation amplification reaction (LAR)-amplification of specific DNA sequences using sequential rounds of template-dependent ligation," Genomics 4(4): 560-569 (1989).

* cited by examiner

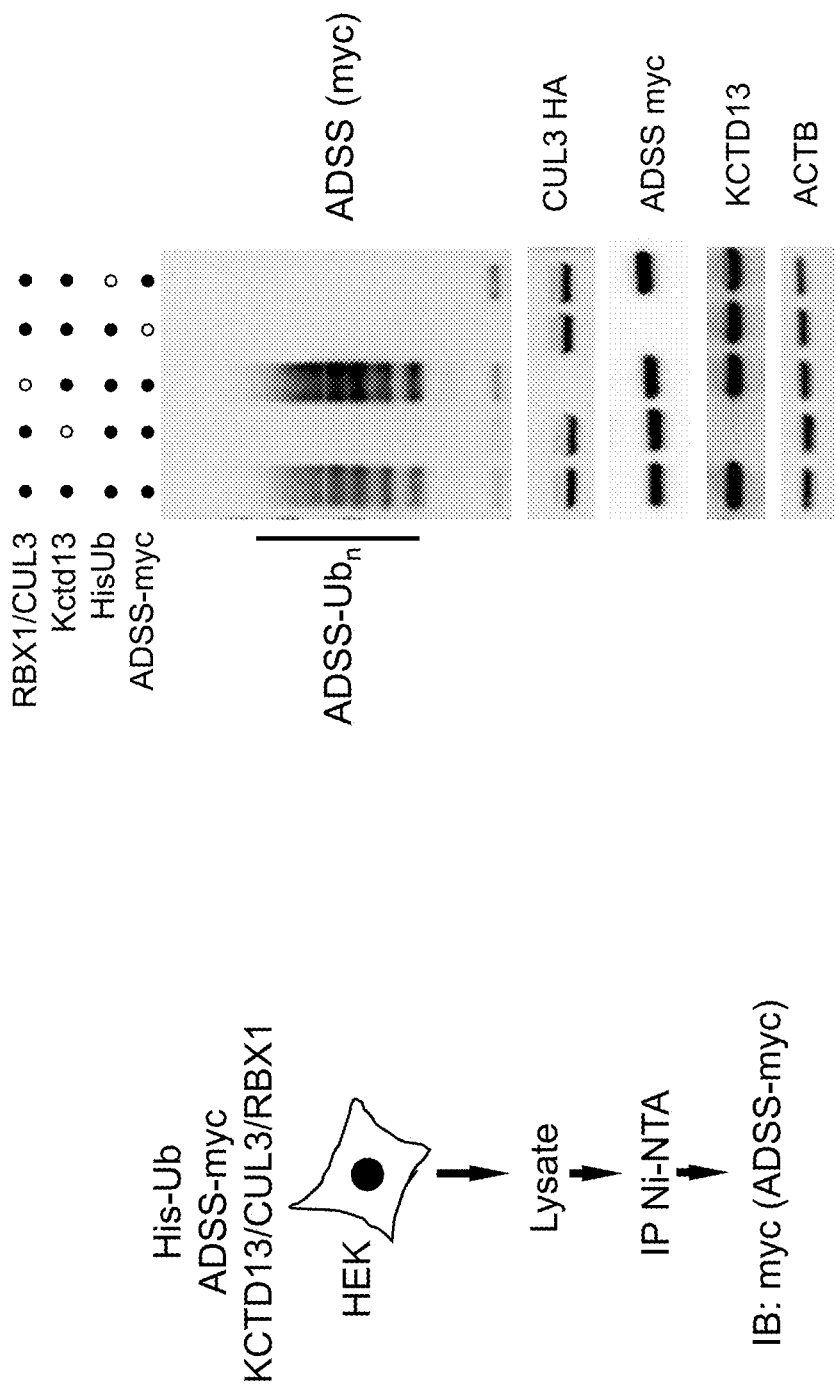

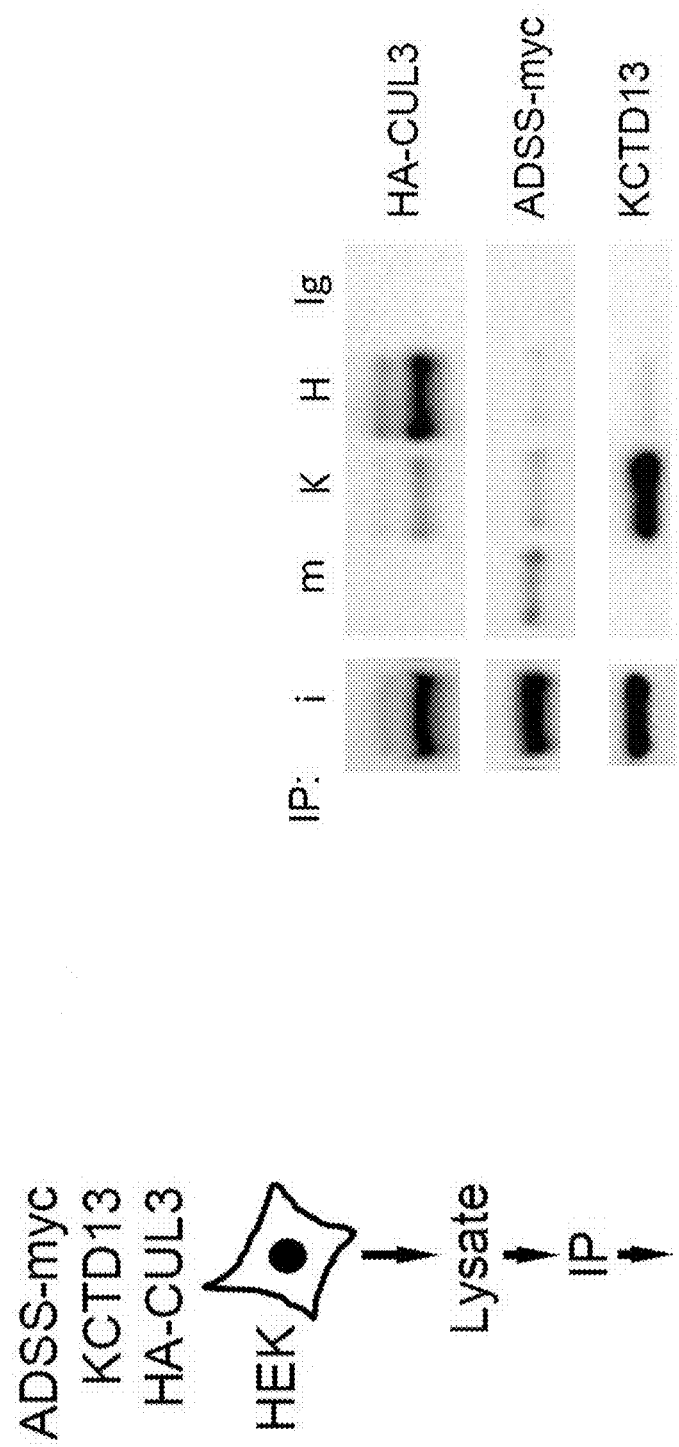

METHODS OF TREATING AUTISM SPECTRUM DISORDERS

CROSS-REFERENCE TO RELATED APPLICATIONS

This application is a continuation of International Application No. PCT/US2017/67099, filed Dec. 18, 2017, which claims the benefit of priority of U.S. Provisional Application Nos. 62/435,986, filed Dec. 19, 2016; 62/559,765, filed Sep. 18, 2017; and 62/582,472, filed Nov. 7, 2017; each of which is incorporated by reference herein in its entirety for any purpose.

SEQUENCE LISTING

The instant application contains a Sequence Listing which has been submitted electronically in ASCII format and is hereby incorporated by reference in its entirety. Said ASCII copy, created on Jun. 12, 2019, is named 2019-06-12_01180-0001-00US_Seq_List_ST25.txt and is 22,685 bytes in size.

FIELD

The present application relates to field of treatment of autism spectrum disorders.

BACKGROUND

Autism spectrum disorders (ASDs) are one of a group of linked neurodevelopment disorders (NDDs). ASDs are characterized by abnormalities in social interaction and communication, restricted interests, and repetitive behaviors. Symptoms of autism typically appear in the first two years of life and affect brain function and development. Classification of ASDs in the Diagnosis and Statistical Manual of Mental Disorders, Fifth Edition (DSM-5) lists distinct forms including Asperger syndrome, Rett syndrome, childhood disintegrative disorder, and pervasive developmental disorder not otherwise specified (PDD-NOS). Many other NDDs exhibit behaviors and symptoms similar to autism.

The US Centers for Disease Control and Prevention (CDC) estimate that 1 in 88 children in the US have an ASD, with a ten-fold increase in prevalence over the past 40 years that is only partially explained by improved diagnosis and awareness. Compared with girls, boys are approximately four to five times more likely to be diagnosed with an ASD.

ASDs are highly heritable and exhibit a 2-3% recurrence rate in siblings and a 60%-90% concordance rate in siblings. However, known genetic causes (including chromosomal abnormalities or Fragile-X syndrome) account for only 10%-20% of ASD cases. The interaction of numerous genes, as well as environmental factors, is thought to confer susceptibility to ASDs. Cellular dysfunction, including neuroinflammation, oxidative stress, mitochondrial abnormalities, and abnormal synaptic plasticity, have been proposed as cellular mechanisms predisposing individuals to ASDs.

There are currently no effective methods of treatment or prevention of ASDs. Treatments are needed that can improve core features of ASDs and affect the neurodevelopmental trajectory of ASDs.

SUMMARY

In some embodiments, a method of treatment of an autism spectrum disorder (ASD) is provided comprising modulating the activity of the molecular pathway involved in the conversion of IMP to AMP and/or downstream signaling through AMP-kinase (AMPK) in a subject in need thereof.

In some embodiments, a method of treatment of an autism spectrum disorder is provided comprising modulating the amount or activity of one or more enzymes in the molecular pathways involved in the conversion of inosine monophosphate (IMP) to adenosine monophosphate (AMP) or downstream signaling through AMPK in a subject in need thereof.

In some embodiments, a method of treatment of an ASD is provided comprising modulating the amount or activity of one or more metabolites of the molecular pathways involved in the conversion of IMP to AMP or downstream signaling through AMPK in a subject in need thereof.

In some embodiments, a method of treatment of an ASD is provided comprising administering to a subject in need thereof an adenylosuccinate (succinyl-adenosine monophosphate or S-AMP) modulator.

In some embodiments, the S-AMP modulator is an adenylosuccinate synthetase (ADSS) inhibitor. In some embodiments, the ADSS inhibitor is an antisense oligonucleotide, an siRNA, a peptide, or a small molecule.

In some embodiments, the ADSS inhibitor is a small molecule. In some embodiments, the ADSS inhibitor is L-alanosine or D,L-alanosine.

In some embodiments, the ADSS inhibitor is selected from hydantocidin, hydantocidin phosphate, hydantocidin-hadacidin S hybrid inhibitor, and hydantocidin-hadacidin R hybrid inhibitor, shown below.

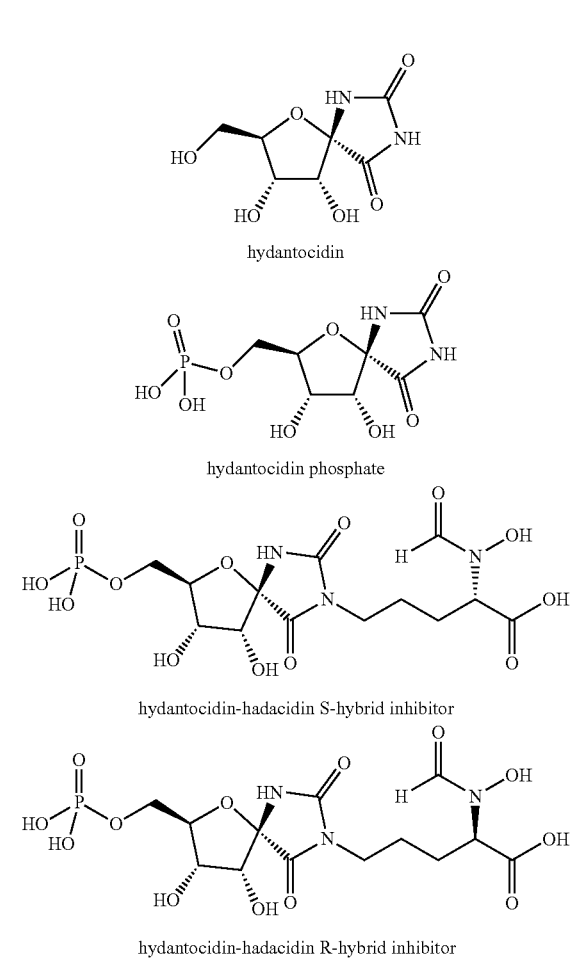

hydantocidin hydantocidin phosphate hydantocidin-hadacidin S-hybrid inhibitor hydantocidin-hadacidin R-hybrid inhibitor In some embodiments, the ADSS inhibitor is selected from GE-101, GE-109, and hadacidin, shown below.

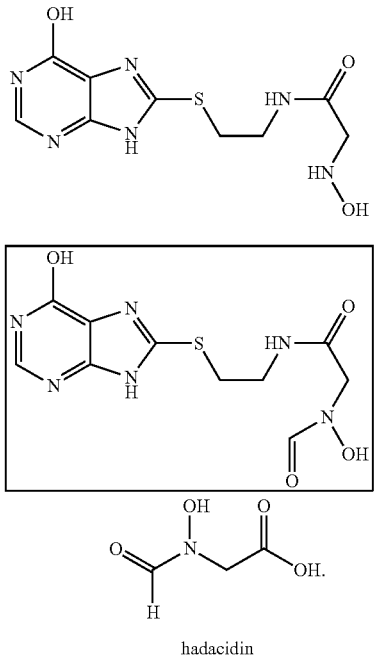

In some embodiments, the ADSS inhibitor is selected from AdSS-1 and AdSS-2:

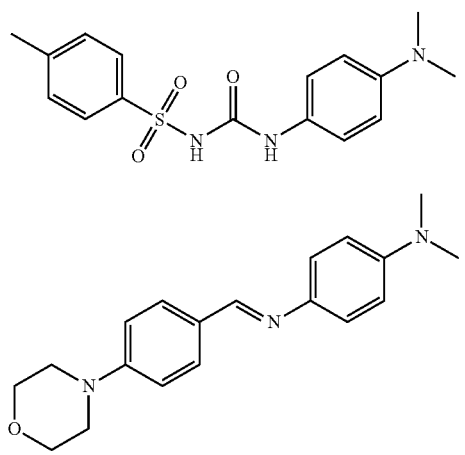

In some embodiments, the ADSS inhibitor is a compound having structure A:

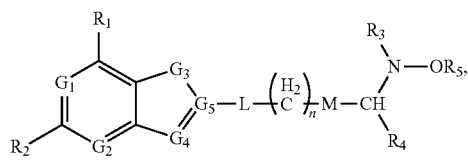

wherein each of $R_1$ and $R_2$ is independently selected from the group consisting of —H, a halogen, —$NH_2$, —OH, —NH—$R_3$, and —O—$R_3$;

each of $G_1$, $G_2$, and $G_4$, is independently selected from the group consisting of CH, N, O, and S, or $G_4$ is independently C=O group;

$G_3$ is independently selected from the group consisting of $CH_2$, NH, O, C=O group and S;

$G_5$ is independently selected from the group consisting of C and N;

L is absent or is selected from the group consisting of O, NH, and S;

$R_3$ is selected from a group consisting of —H, an $C_1$-$C_{18}$ alkyl, an aryl, —C(O)—H, and —C(O)-alkyl;

$R_4$ is selected from a group consisting of —H, —C(O)O—; and —C(O)—$R_3$;

$R_5$ is selected from a group consisting of —H, an $C_1$-$C_{18}$ alkyl, and an aryl;

M is absent or is selected from the group consisting of —$CH_2$—; —NH—; —NH—C(O)—; —O—, and —S—; and n is an integer having the value between 1 and 6.

In some embodiments, $G_1$, $G_2$, and $G_4$ are N, $G_3$ is NH, and $G_5$ is C.

Various nonlimiting exemplary small molecule ADSS inhibitors are described, e.g., in WO 2009/023495 and WO 92/07569; Crowther et al., 2011, *Mol. Biol. Parisitol.*, 175: 21-29; and Hanessian et al., 1999, *Angew Chem Int Ed* 38: 3159-62.

In some embodiments, the ADSS inhibitor is an antisense oligonucleotide. In some embodiments, the antisense oligonucleotide is complementary to a portion of the ADSS mRNA.

In some embodiments, the ADSS inhibitor is an siRNA. In some embodiments, the siRNA targets a portion of the ADSS mRNA.

In some embodiments, the ADSS inhibitor is a peptide.

In some embodiments, the S-AMP modulator is an adenylosuccinate lyase activator. In some embodiments, the adenylosuccinate lyase activator increases the amount of adenylosuccinate lyase and/or increases the activity of adenylosuccinate lyase.

In some embodiments, the method comprises increasing the amount of adenylosuccinate lyase. In some embodiments, the amount of adenylosuccinate lyase is increased by administering a nucleic acid that encodes adenylosuccinate lyase. In some embodiments, the amount of adenylosuccinate lyase is increased by inhibiting its degradation.

In some embodiments, the method comprises increasing the activity of adenylosuccinate lyase. In some embodiments, the activity of adenylosuccinate lyase is increased by the addition of an activator. In some embodiments an activator of adenylosuccinate lyase activity is a small molecule. In some embodiments, an activator of adenylosuccinate lyase activity is a peptide.

In some embodiments, a method of treating an ASD is provided comprising reducing the amount of S-Ado in a subject in need thereof. In some embodiments, a method of treating an ASD is provided comprising administering to a subject in need thereof a succinyl-adenosine (S-Ado) reducing agent. In some embodiments, the S-Ado reducing agent is an antibody that binds S-Ado. In some embodiments, the antibody is an antibody fragment. In some embodiments, the antibody fragment is selected from an scFv, Fab, Fab', F(ab')2 fragment. In some embodiments, the S-Ado reducing agent is an abzyme.

In some embodiments, an S-Ado reducing agent is an agent that modulates the activity of one or more enzymes responsible for the synthesis or degradation of S-Ado. In some embodiments, an S-Ado reducing agent is an agent that inhibits the enzymatic synthesis of S-Ado. In some embodiments, an S-Ado reducing agent is an agent that activates the enzymatic degradation of S-Ado. In some embodiments, an S-Ado reducing agent is an agent that activates the conversion of S-Ado into a non-S-Ado form. In some embodiments, an S-Ado reducing agent is a peptide. In some embodiments, an S-Ado reducing agent is a small molecule.

In some embodiments, a method of treating an ASD is provided comprising reducing the amount or activity of AMPK. In some embodiments, the activity of AMPK is modulated by the administration of an AMPK inhibitor. In some embodiments, the amount of AMPK is modulated by decreasing the amount of AMP. In some embodiments, the AMPK inhibitor is an antisense oligonucleotide, an siRNA, a peptide, or a small molecule.

In some embodiments, the AMPK inhibitor is a small molecule. In some such embodiments, the small molecule inhibits the activity of AMPK. In some embodiments, the AMPK inhibitor is dorsomorphin, such as dorsomorphin hydrochloride.

In some embodiments, the AMPK inhibitor is an antisense oligonucleotide. In some such embodiments, the antisense oligonucleotide reduces the amount of AMPK. In some embodiments, the antisense oligonucleotide is complementary to a portion of the AMPK mRNA.

In some embodiments, the AMPK inhibitor is an siRNA. In some such embodiments, the siRNA reduces the amount of AMPK. In some embodiments, the siRNA is complementary to a portion of the AMPK mRNA.

In some embodiments, the AMPK inhibitor is a peptide. In some such embodiments, the peptide inhibits the activity of AMPK.

In some embodiments, the subject has a 16p11.2 deletion. In some embodiments, the subject has a mutation in the KCTD13 gene. In some embodiments, the mutation in the KCTD13 gene is a loss-of-function mutation. In some embodiments, the mutation in the KCTD13 gene is a partial or total deletion of the KCTD13 gene, or a missense mutation, or a nonsense mutation.

In some embodiments, the subject has a mutation in the CUL3 gene. In some embodiments, the mutation in the CUL3 gene is a loss-of-function mutation. In some embodiments, the mutation in the CUL3 gene is a partial or total deletion of the CUL3 gene, or a missense mutation, or a nonsense mutation.

In some embodiments, the subject has an elevated level of S-Ado. In some embodiments, the elevated level of S-Ado is determined in a blood, urine, or CSF sample from the subject.

In some embodiments, treating an autism spectrum disorder comprises alleviating at least one symptom of the autism spectrum disorder. In some embodiments, alleviating at least one symptom comprises reducing the number, severity, and/or frequency of seizures; preventing and/or slowing developmental delay; improving and/or slowing the decline in intellectual ability; reducing the incidence of obesity; reducing social interaction deficit; improving language; reducing repetitive behaviors; reducing sleep disorders; reducing mood disorders; reducing anxiety; reducing gastrointestinal symptoms; reducing hyperactivity; and/or reducing attention deficits.

In some embodiments, a method of identifying a subject who would benefit from treatment with an ADSS inhibitor is provided comprising determining the level of S-Ado in a sample from the subject, wherein an elevated level of S-Ado in the sample indicates the subject would benefit from treatment with an S-AMP modulator. In some embodiments, the level of S-Ado in the sample is compared to a reference level of S-Ado. In some embodiments, the method further comprises determining whether the subject has a 16p11.2 deletion, wherein a 16p11.2 deletion indicates the subject would benefit from treatment with an S-AMP modulator.

In some embodiments, the method further comprises determining whether the subject has a mutation in the KCTD13 gene, wherein a mutation in the KCTD13 gene indicates the subject would benefit from treatment with an S-AMP modulator. In some embodiments, the mutation in the KCTD13 gene is a loss-of-function mutation. In some embodiments, the mutation in the KCTD13 gene is a partial or total deletion of the KCTD13 gene.

In some embodiments, the method further comprises determining whether the subject has a mutation in the CUL3 gene, wherein a mutation in the CUL3 gene indicates the subject would benefit from treatment with an S-AMP modulator. In some embodiments, the mutation in the CUL3 gene is a loss-of-function mutation. In some embodiments, the mutation in the CUL3 gene is a partial or total deletion of the CUL3 gene.

In some embodiments, a method of identifying a subject who would benefit from treatment with an ADSS inhibitor is provided comprising determining whether the subject has a 16p11.2 deletion, wherein a 16p11.2 deletion indicates the subject would benefit from treatment with an ADSS inhibitor.

In some embodiments, a method of identifying a subject who would benefit from treatment with an ADSS inhibitor is provided comprising determining whether the subject has a mutation in the KCTD13 gene, wherein a mutation in the KCTD13 gene indicates the subject would benefit from treatment with an ADSS inhibitor. In some embodiments, the mutation in the KCTD13 gene is a loss-of-function mutation. In some embodiments, the mutation in the KCTD13 gene is a partial or total deletion of the KCTD13 gene.

In some embodiments, a method of identifying a subject who would benefit from treatment with an ADSS inhibitor is provided comprising determining whether the subject has a mutation in the CUL3 gene, wherein a mutation in the CUL3 gene indicates the subject would benefit from treatment with an ADSS inhibitor. In some embodiments, the mutation in the CUL3 gene is a loss-of-function mutation. In some embodiments, the mutation in the CUL3 gene is a partial or total deletion of the CUL3 gene.

In some embodiments, the method further comprises determining the level of S-Ado in a sample from the subject, wherein an elevated level of S-Ado in the sample indicates the subject would benefit from treatment with an S-AMP modulator.

In some embodiments, the subject exhibits at least one symptom of an autism spectrum disorder. In some embodiments, at least one symptom of an autism spectrum disorder is selected from development delay, intellectual disability, seizures, increased risk of obesity; social interaction deficit; language impairment; repetitive behaviors; sleep disorder; mood disorder; anxiety; gastrointestinal symptoms; hyperactivity; and attention deficits. In some embodiments, the subject has been previously diagnosed as having an autism spectrum disorder.

In some embodiments, the subject does not have an adenylosuccinate lyase deficiency.

In some embodiments, the S-AMP modulator is selected from an ADSS inhibitor, an adenylosuccinate lyase activator, and an S-Ado reducing agent.

In some embodiments, the method comprises administering to the subject an S-AMP modulator. In some embodiments, the S-AMP modulator is an ADSS inhibitor.

In some embodiments, the ADSS inhibitor is an antisense oligonucleotide, an siRNA, a peptide, or a small molecule.

In some embodiments, the ADSS inhibitor is a small molecule. In some embodiments, the ADSS inhibitor is L-alanosine or D,L-alanosine.

In some embodiments, the ADSS inhibitor is selected from hydantocidin, hydantocidin phosphate, hydantocidin-hadacidin S hybrid inhibitor, and hydantocidin-hadacidin R hybrid inhibitor, shown below.

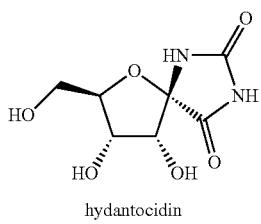

hydantocidin

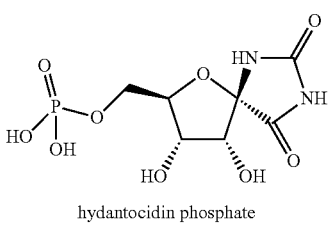

hydantocidin phosphate

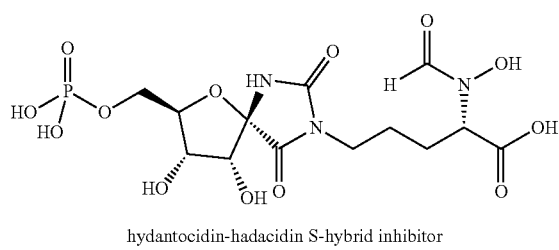

hydantocidin-hadacidin S-hybrid inhibitor

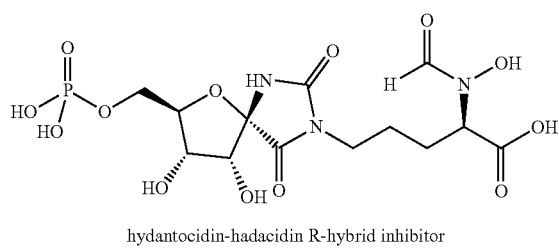

hydantocidin-hadacidin R-hybrid inhibitor

In some embodiments, the ADSS inhibitor is selected from GE-101, GE-109, and hadacidin, shown below.

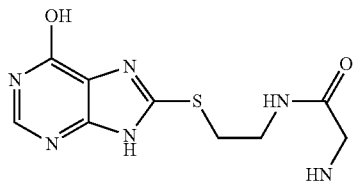

GE-101

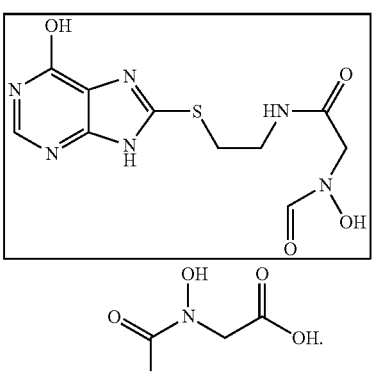

GE-109

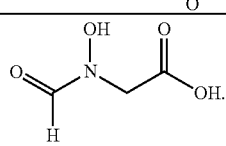

hadacidin

In some embodiments, the ADSS inhibitor is selected from AdSS-1 and AdSS-2:

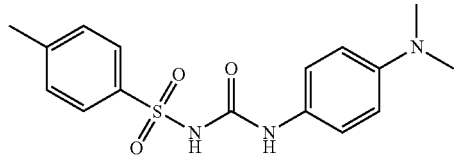

AdSS-1

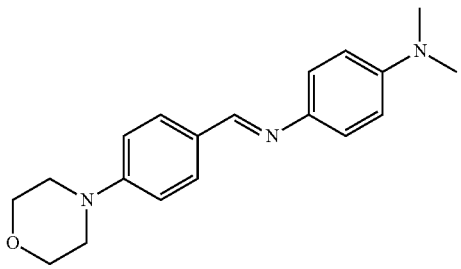

AdSS-2

In some embodiments, the ADSS inhibitor is a compound having structure A:

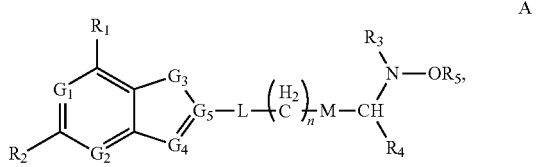

A wherein each of $R_1$ and $R_2$ is independently selected from the group consisting of —H, a halogen, —$NH_2$, —OH, —NH—$R_3$, and —O—$R_3$;

each of $G_1$, $G_2$, and $G_4$, is independently selected from the group consisting of CH, N, O, and S, or $G_4$ is independently C=O group;

$G_3$ is independently selected from the group consisting of $CH_2$, NH, O, C=O group and S;

$G_5$ is independently selected from the group consisting of C and N;

L is absent or is selected from the group consisting of O, NH, and S;

$R_3$ is selected from a group consisting of —H, an $C_1$-$C_{18}$ alkyl, an aryl, —C(O)—H, and —C(O)-alkyl;

$R_4$ is selected from a group consisting of —H, —C(O)O—; and —C(O)—$R_3$;

$R_5$ is selected from a group consisting of —H, an $C_1$-$C_{18}$ alkyl, and an aryl;

M is absent or is selected from the group consisting of —$CH_2$—; —NH—; —NH—C(O)—; —O—, and —S—; and n is an integer having the value between 1 and 6.

In some embodiments, $G_1$, $G_2$, and $G_4$ are N, $G_3$ is NH, and $G_5$ is C.

Various nonlimiting exemplary small molecule ADSS inhibitors are described, e.g., in WO 2009/023495 and WO 92/07569; Crowther et al., 2011, *Mol. Biol. Parisitol.*, 175: 21-29; and Hanessian et al., 1999, *Angew Chem Int Ed* 38: 3159-62.

In some embodiments, the ADSS inhibitor is an antisense oligonucleotide. In some embodiments, the antisense oligonucleotide is complementary to a portion of the ADSS mRNA.

In some embodiments, the ADSS inhibitor is an siRNA. In some embodiments, the siRNA targets a portion of the ADSS mRNA.

In some embodiments, the ADSS inhibitor is a peptide.

In some embodiments, the S-AMP modulator is an adenylosuccinate lyase activator. In some embodiments, the adenylosuccinate lyase activator increases the level of adenylosuccinate lyase and/or increases the activity of adenylosuccinate lyase. In some embodiments, the method comprises administering a nucleic acid that encodes adenylosuccinate lyase.

In some embodiments, the method comprises administering to the subject a succinyl-adenosine (S-Ado) reducing agent. In some embodiments, the S-Ado reducing agent is an antibody that binds S-Ado. In some embodiments, the antibody is an antibody fragment. In some embodiments, the antibody fragment is selected from an scFv, Fab, Fab', F(ab')2 fragment.

In some embodiments, a method of monitoring treatment of a subject with an S-AMP modulator or S-Ado reducing agent comprises determining the level of S-Ado in a sample from the subject. In some embodiments, the level of S-Ado is determined at at least two time points. In some embodiments, the level of S-Ado is determined in a first sample from the subject and in a second sample from the subject, wherein the second sample from the subject is taken at a later point in time than the first sample from the subject. In some embodiments, the first sample from the subject is taken prior to treatment with an S-AMP modulator or S-Ado reducing agent and the second sample from the subject is taken after administration of at least one dose of an S-AMP modulator or S-Ado reducing agent.

In some embodiments, the first sample from the subject is taken at a first time point and the second sample from the subject is taken at a second time point, wherein at least one dose of an S-AMP modulator or S-Ado reducing agent is administered between the first time point and the second time point. In some embodiments, a decrease in the level of S-Ado in the second sample compared to the first sample indicates the treatment is effective.

In some embodiments, the method is a method of monitoring treatment of a subject with an S-AMP modulator. In some embodiments, the S-AMP modulator is an ADSS inhibitor.

In some embodiments, the ADSS inhibitor is an antisense oligonucleotide, an siRNA, a peptide, or a small molecule. In some embodiments, the ADSS inhibitor is a small molecule.

In some embodiments, the ADSS inhibitor is L-alanosine or D,L-alanosine.

In some embodiments, the ADSS inhibitor is an antisense oligonucleotide. In some embodiments, the antisense oligonucleotide is complementary to a portion of the ADSS mRNA. In some embodiments, the ADSS inhibitor is an siRNA. In some embodiments, the siRNA is complementary to a portion of the ADSS mRNA. In some embodiments, the ADSS inhibitor is a peptide. In some embodiments, the S-AMP modulator is an adenylosuccinate lyase activator.

In some embodiments, the adenylosuccinate lyase activator increases the level of adenylosuccinate lyase and/or increases the activity of adenylosuccinate lyase.

In some embodiments, the method comprises administering a nucleic acid that encodes adenylosuccinate lyase. In some embodiments, the method is a method of monitoring treatment of a subject with an S-Ado reducing agent. In some embodiments, the S-Ado reducing agent is an antibody that binds S-Ado. In some embodiments, the antibody is an antibody fragment. In some embodiments, the antibody fragment is selected from an scFv, Fab, Fab', F(ab')2 fragment.

In some embodiments, the sample is selected from a blood sample, a urine sample, and a CSF sample.

In any of the embodiments described herein, a method of treating an ASD further comprises placing the subject on a low purine diet.

In some embodiments, a method of treating an autism spectrum disorder in a subject comprises placing the subject on a low purine diet. In some embodiments, the subject has a 16p11.2 deletion. In some embodiments, the subject has a mutation in the KCTD13 gene. In some embodiments, the mutation in the KCTD13 gene is a loss-of-function mutation. In some embodiments, the mutation in the KCTD13 gene is a partial or total deletion of the KCTD13 gene, a missense mutation, or a nonsense mutation. In some embodiments, the subject has a mutation in the CUL3 gene. In some embodiments, the mutation in the CUL3 gene is a loss-of-function mutation. In some embodiments, the mutation in the CUL3 gene is a partial or total deletion of the CUL3 gene, a missense mutation, or a nonsense mutation. In some embodiments, the subject has an elevated level of S-Ado. In some embodiments, the elevated level of S-Ado is determined in a blood, urine, or CSF sample from the subject. In some embodiments, treating an autism spectrum disorder comprises alleviating at least one symptom of the autism spectrum disorder. In some embodiments, alleviating at least one symptom comprises reducing the number, severity, and/or frequency of seizures; preventing and/or slowing developmental delay; improving and/or slowing the decline in intellectual ability; reducing the incidence of obesity; reducing social interaction deficit; improving language; reducing repetitive behaviors; reducing sleep disorders;

reducing mood disorders; reducing anxiety; reducing gastrointestinal symptoms; reducing hyperactivity; and/or reducing attention deficits.

In some embodiments, a method of monitoring treatment of a subject having an autism spectrum disorder with low purine diet is provided, comprising determining the level of S-Ado in a sample from the subject. In some embodiments, the level of S-Ado is determined at at least two time points. In some embodiments, the level of S-Ado is determined in a first sample from the subject and in a second sample from the subject, wherein the second sample from the subject is taken at a later point in time than the first sample from the subject. In some embodiments, the first sample from the subject is taken prior to treatment with a low purine diet and the second sample from the subject is taken after treatment with the low purine diet. In some embodiments, the second sample from the subject is taken after at least 1 week, at least 2 weeks, at least 3 weeks, at least 4 weeks, at least 6 weeks, at least 2 months, at least 3 months, at least 6 months, or at least 1 year after the start of treatment with the low purine diet. In some embodiments, a decrease in the level of S-Ado in the second sample compared to the first sample indicates the treatment is effective. In some embodiments, the method is a method of monitoring treatment of a subject with a low purine diet.

It is to be understood that both the foregoing general description and the following detailed description are exemplary and explanatory only and are not restrictive of the claims.

BRIEF DESCRIPTION OF THE DRAWINGS

FIGS. 6A-6B show experimental protocol (A) and results (B) on the effect of KCTD13 transfection on ubiquitination of ADSS in a HEK model with exogenous expression of HisUb and RBX1/CUL3. Ni-NTA refers to magnetic beads. IB=immunoblot; IP=immunoprecipitation; Ub=ubiquitin.

FIGS. 10A-10B show the experimental conditions (A) and results (B) for the immunoprecipitation experiment to study the ADSS-KCTD13-CUL3 interaction. i=input; Ig=non-specific Ig control; K=KCTD13 antibody; m=myc antibody.

DESCRIPTION OF CERTAIN EMBODIMENTS

I. Definitions

Figure 1:
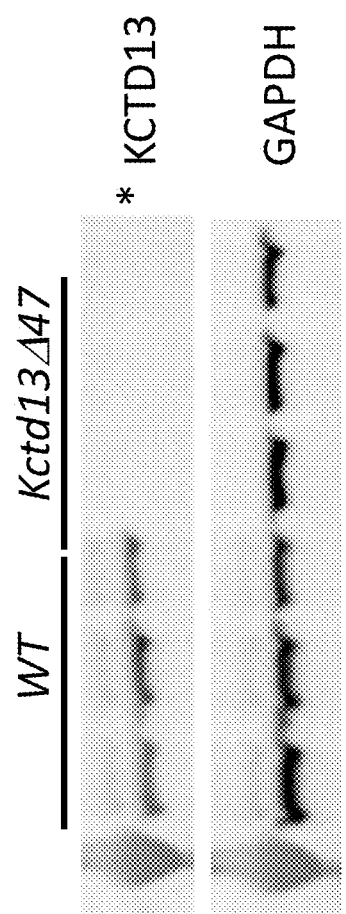
FIG. 1 provides western blot analysis of KCTD13 and glyceraldehyde 3-phosphate dehydrogenase (GAPDH) levels in Kctd13Δ47 mice compared to wildtype (WT).

As used herein, the term "about" refers to a numeric value, including, for example, whole numbers, fractions, and percentages, whether or not explicitly indicated. The term "about" generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. In some embodiments, an antibody may be a chimeric antibody, a humanized antibody, or a human antibody.

The term antibody includes, but is not limited to, fragments that are capable of binding to an antigen, such as Fv, single-chain Fv (scFv), Fab, Fab', di-scFv, sdAb (single domain antibody) and (Fab')$_2$ (including a chemically linked F(ab')$_2$). The term antibody also includes, but is not limited to, chimeric antibodies, humanized antibodies, and antibodies of various species such as mouse, human, cynomolgus monkey, etc. Antibody fragments also include either orientation of single chain scFvs, tandem di-scFv, diabodies, tandem tri-sdcFv, minibodies, etc. Antibody fragments also include nanobodies (sdAb, an antibody having a single, monomeric domain, such as a pair of variable domains of heavy chains, without a light chain). An antibody fragment can be referred to as being a specific species in some embodiments (for example, human scFv or a mouse scFv).

An "abzyme" or "catalytic antibody" refers to a monoclonal antibody with catalytic activity.

The term "antisense oligonucleotide" refers to a single-stranded oligonucleotide comprising 8 to 50 monomeric units and having a nucleobase sequence that permits hybridization to a corresponding segment of a target nucleic acid. An antisense oligonucleotide may comprise natural, non-natural, and/or modified nucleosides and/or internucleoside linkages.

The term "siRNA" refers to a double-stranded oligonucleotide comprising a first strand comprising 10 to 30 monomeric units and a second strand comprising 10 to 30 monomeric units that is complementary to the first strand, wherein the first strand or second strand has a nucleobase sequence that permits hybridization to a corresponding segment of a target nucleic acid. The first strand and second strand may have 0, 1, 2, or 3 mismatches with respect to one another.

The term "monoclonal antibody" refers to an antibody of a substantially homogeneous population of antibodies, that is, the individual antibodies comprising the population are identical except for possible naturally-occurring mutations that may be present in minor amounts. Monoclonal antibodies are specific, being directed against a single antigenic site. Furthermore, in contrast to polyclonal antibody preparations, which typically include different antibodies directed against different determinants (epitopes), each antibody in a monoclonal antibody preparation is directed against a single determinant on the antigen. Thus, a sample of monoclonal antibodies can bind to the same epitope on the antigen. The modifier "monoclonal" indicates the character of the antibody as being obtained from a substantially homogeneous population of antibodies, and is not to be construed as requiring production of the antibody by any particular method. For example, the monoclonal antibodies may be made by the hybridoma method, by recombinant DNA methods, or be isolated from phage libraries.

The term "peptide" as used herein refers to a molecule formed by linking at least two, and up to 300, amino acids by amide bonds. The amino acids of a peptide may be natural, non-natural, and/or modified amino acids. In some embodiments, a peptide comprises 2-200 amino acids, or 2-100 amino acids, or 2-50 amino acids, or 2-30 amino acids, or 10-300 amino acids, or 10-200 amino acids, or 10-100 amino acids, or 10-50 amino acids.

The term "vector" is used to describe a polynucleotide that can be engineered to contain a cloned polynucleotide or polynucleotides that can be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated".

The term "biological sample" means a quantity of a substance from a living thing or formerly living thing. Such substances include, but are not limited to, blood, (for example, whole blood), plasma, serum, urine, amniotic fluid, synovial fluid, endothelial cells, leukocytes, monocytes, cerebrospinal fluid, other cells, organs, and tissues.

A "reference" as used herein, refers to any sample, standard, or level that is used for comparison purposes. A reference may be obtained from a healthy and/or non-diseased sample. In some examples, a reference may be obtained from an untreated sample, or may be a sample from the subject prior to treatment. In some examples, a reference is obtained from one or more healthy individuals who are not the subject or patient.

An "autism spectrum disorder" or an "ASD" refers to any one of a group of complex disorders of brain development. "Autism" may be used interchangeably with ASD. ASD includes, but is not limited to, autistic disorder, Rett syndrome, childhood disintegrative disorder, pervasive developmental disorder—not otherwise specified (PDD-NOS), and Asperger syndrome. ASD can be associated with intellectual disability, impairments in communication skills and social interactions, difficulties in motor coordination and attention, seizures, increased risk of obesity, and other symptoms such as sleep and gastrointestinal disturbances. ASD encompasses disorders with varying degrees of impairment, and symptoms may also include restricted, repetitive, and stereotyped patterns of behavior. ASD may have a single-gene or multi-gene etiology, but the etiology of an ASD in an individual subject may also be unknown.

"Adenylosuccinate synthetase" and "ADSS" as used herein refer to any native ADSS that results from expression and processing of ADSS in a cell. As used herein, "ADSS" also comprises related adenylosuccinate synthetase like (ADSSL) proteins. The term includes ADSS from any vertebrate source, including mammals such as primates (e.g., humans and cynomolgus monkeys) and rodents (e.g., mice and rats), unless otherwise indicated. The term also includes naturally occurring variants of ADSS, e.g., splice variants, isoforms, isozymes, or allelic variants. The amino acid sequence of an exemplary human ADSS protein is shown in SEQ ID NO: 12.

"Adenylosuccinate lyase" and "ADSL" as used herein refer to any native ADSL that results from expression and processing of ADSL in a cell. The term includes ADSL from any vertebrate source, including mammals such as primates (e.g., humans and cynomolgus monkeys) and rodents (e.g., mice and rats), unless otherwise indicated. The term also includes naturally occurring variants of ADSL, e.g., splice variants, isoforms, isozymes, or allelic variants. The amino acid sequence of an exemplary human ADSL protein is shown in SEQ ID NO: 13.

"AMP kinase" and "AMPK" and "5'-AMP-activated protein kinase" as used herein refer to any native AMP kinase that results from expression and processing of AMP kinase in a cell. The term includes AMP kinase from any vertebrate source, including mammals such as primates (e.g., humans and cynomolgus monkeys) and rodents (e.g., mice and rats), unless otherwise indicated. The term also includes naturally occurring variants of AMP kinase, e.g., splice variants, isoforms, isozymes, or allelic variants. AMP kinase is a heterotrimeric protein comprising $\alpha$, $\beta$, and $\gamma$ subunits. The amino acid sequences of exemplary human AMP kinase subunits are shown in SEQ ID Nos: 17-19.

An "S-AMP modulator" or "adenylosuccinate modulator" or "succinyl-adenosine monophosphate modulator" refers to an agent that decreases the production or level of S-AMP. S-AMP modulators include, but are not limited to, adenylosuccinate synthetase (ADSS) inhibitors and adenylosuccinate lyase activators.

An "AMPK modulator" refers to an agent that decreases the amount or activity of AMPK. AMPK modulators include, but are not limited to, AMPK inhibitors and AMP reducing agents.

An "AMPK inhibitor" or refers to an agent that inhibits the expression or activity of AMPK, and/or reduces the level of AMPK.

An "AMP reducing agent" refers to an agent that decreases the amount of AMP.

An "adenylosuccinate synthetase inhibitor" or "ADSS inhibitor" refers to an agent that inhibits the expression or activity of ADSS, and/or reduces the level of ADSS.

An "adenylosuccinate lyase activator" refers to an agent that increases the expression, level, or activity of adenylosuccinate lyase.

An "succinyl-adenosine reducing agent" or "S-Ado reducing agent" refers to an agent that reduces the level of free S-Ado and/or its metabolites in a subject. In some embodiments, an S-Ado reducing agent reduces the level of extracellular free S-Ado and/or its metabolites in a subject. In some embodiments, an S-Ado reducing agent reduces the level of S-Ado and/or its metabolites in blood, urine, and/or cerebrospinal fluid. Reduction of free S-Ado and/or its metabolites includes degradation of S-Ado and/or its metabolites and/or binding of S-Ado and/or its metabolites such that its deleterious effects are substantially mitigated.

An "effective amount" of an agent, e.g., a pharmaceutical formulation, refers to an amount effective, at dosages and for periods of time necessary, to achieve the desired therapeutic or prophylactic result.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In various embodiments, the individual or subject is a human.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

A "pharmaceutically acceptable salt" means a physiologically and pharmaceutically acceptable salt of a compounds, i.e., a salt that retains the desired biological activity of the compound and does not impart undesired toxicological effects thereto. Any of the compounds described herein, such as any of the small molecule inhibitors, includes pharmaceutically acceptable salts thereof.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of a disease or condition, alleviation of symptoms, diminishment of any direct or indirect pathological consequences of the disease or condition, decreasing the rate of disease progression, amelioration or palliation of the disease or condition, and remission or improved prognosis. In some embodiments, methods are provided that delay development of a condition or disease or one or more symptoms of the condition or disease, or slow the progression of a disease or condition.

II. Exemplary Therapeutic Methods

16p11.2 has been identified as a risk locus for autism. See, e.g., Sanders et al., 2015, Neuron 87: 1215-33; Kumar et al., 2008, *Hum. Mol. Genet.* 17: 628-38; Weiss et al., 2008, *New Engl. J. Med.* 358: 667-675; Marshall et al., 2008, *Am. J. Hum. Genet.*, 82: 477-88. KCTD13, a protein that binds to CUL3 and is involved in the ubiquitination pathway, is one of many genes located in 16p11.2. Deletion of KCTD13 has been proposed to cause an increase in RhoA, which leads to stress fiber formation, axon growth inhibition, enhanced cell spreading, loss of dendritic spines, and neurite retraction. See, e.g., Lin et al. 2015, *Neuron,* 85: 742-754.

The present inventors have identified adenylosuccinate synthetase (ADSS) as a substrate of a ubiquitin ligase complex involving Kctd13 and Cul3, and have demonstrated that deletion of KCTD13 gene results in a statistically significant decrease in ADSS ubiquitination and a concomitant increase in ADSS protein levels. As discussed below, the increase in ADSS protein levels is expected to lead to the presence of extracellular S-Ado and its metabolites in individuals with loss-of-function KCTD13 gene mutations.

ADSS catalyzes the conversion of IMP to adenylosuccinate (S-AMP), which is then converted to AMP by adenylosuccinate lyase. See, e.g., FIG. 4. A build-up of S-AMP leads to dephosphorylation of S-AMP and secretion of S-Ado from cells. S-Ado is not detectable in the blood, urine, or cerebrospinal fluid of healthy individuals, suggesting that secretion of S-Ado is the result of a dysregulated AMP synthesis pathway. Intriguingly, mutations in the second enzyme in the pathway, adenylosuccinate lyase (ADSL), can result in a rare condition referred to as ADSL deficiency, in which S-Ado and another ADSL substrate, succinylaminoimidazole carboxamide ribotide (SAICAR), accumulate in urine, CSF, and plasma. Patients with ADSL deficiency exhibit neurological symptoms, including severe psychomotor retardation, microcephaly, early onset of seizures, and autistic features. See, e.g., Jurecka et al., 2015, *J. Inherit. Metab. Dis.,* 38: 231-242.

Increased S-AMP levels also result in increased AMP levels through the normal enzymatic conversion of S-AMP to AMP by ADSL. AMP is a key regulator of AMP Kinase (AMPK). In the presence of high levels of AMP, AMPK is upregulated and actives a number of different molecular pathways including those involved in glucose metabolism, lipid metabolism, cell growth/autophagy, polarity, and transcription. See, e.g., Mihaylova et al., 2012, *Nat. Cell Biol.*, 13: 1016-23. Thus, the loss-of-function KCTD13 gene mutations may lead to aberrantly activated signaling through one or more of these pathways via aberrantly upregulated AMPK.

Prior the present disclosure, there was no known link between ADSS and the AMP synthesis pathway and the risk loci identified in autism.

Methods of treating an autism spectrum disorder are provided herein. In some embodiments, a method of treatment of an autism spectrum disorder is provided comprising administering to a subject in need thereof an adenylosuccinate (S-AMP) modulator. In some embodiments, a method of treating an autism spectrum disorder (ASD) is provided comprising administering to a subject in need thereof a succinyl-adenosine (S-Ado) reducing agent. In some embodiments, a method of treating an ASD is provided comprising reducing the amount or activity of AMPK. In some such embodiments, the method comprises administering to a subject with ASD an AMPK modulator, such as an AMPK inhibitor or an AMP reducing agent. In some embodiments, a method of treating an ASD in a subject comprises a low purine diet, alone or in combination with other treatments, including the treatments described herein. Low purine diets are well known, e.g., for the treatment and prevention of kidney stones and gout.

In various embodiments, the subject has a 16p11.2 deletion. The 16p11.2 deletion may include deletion of all or a portion of the KCTD13 gene. In some embodiments, the subject has a mutation in the KCTD13 gene, which may be a partial or full deletion, insertion, point mutation, and the like. In some embodiments, the mutation in the KCTD13 gene is a loss-of-function mutation. In some embodiments, the loss-of-function mutation in the KCTD13 gene is a partial or total deletion of the KCTD13 gene.

In some embodiments, the subject has a mutation in the CUL3 gene, which may be a partial or full deletion, insertion, point mutation, and the like. In some embodiments, the mutation in the CUL3 gene is a loss-of-function mutation. In some embodiments, the mutation in the CUL3 gene is a partial or total deletion of the CUL3 gene.

In some embodiments, the subject has an elevated level of S-Ado. In some embodiments, the elevated level of S-Ado is determined in a blood, plasma, urine, or CSF sample from the subject.

In some embodiments, the subject has both a 16p11.2 deletion, which may include a partial or full deletion of the KCTD13 gene and an elevated level of S-Ado. In some embodiments, the subject has both a loss-of-function mutation in the KCTD13 gene and an elevated level of S-Ado. In some embodiments, the subject has both a loss-of-function mutation in the CUL3 gene and an elevated level of S-Ado. In some embodiments, the subject has an elevated level of S-Ado and exhibits one or more symptoms of an autism spectrum disorder. As discussed above, the elevated level of S-Ado may be determined in a blood, plasma, urine, or CSF sample from the subject.

In some embodiments, treating an autism spectrum disorder comprises alleviating at least one symptom of the autism spectrum disorder. In some such embodiments, alleviating at least one symptom comprises reducing the number, severity, and/or frequency of seizures; preventing and/or slowing developmental delay; improving and/or slowing the decline in intellectual ability; reducing the incidence of obesity; reducing social interaction deficit; improving language; reducing repetitive behaviors; reducing sleep disorders; reducing mood disorders; reducing anxiety; reducing gastrointestinal symptoms; reducing hyperactivity; and/or reducing attention deficits.

In various embodiments, methods comprise administering to a subject with an autism spectrum disorder, or a subject suspected of having an autism spectrum disorder, or a subject predicted to develop an autism spectrum disorder, or a subject at risk for developing an autism spectrum disorder, a modulator of adenylosuccinate (S-AMP modulator). In various embodiments, the subject has been identified as having an autism spectrum disorder, or suspected of having an autism spectrum disorder, or predicted to develop an autism spectrum disorder, or at risk for developing an autism disorder, using any diagnostic criteria in the art or described herein. In various embodiments, the S-AMP modulator reduces the production or level of S-AMP.

A. Exemplary S-AMP Modulators

In some embodiments, the S-AMP modulator is an adenylosuccinate synthetase (ADSS) inhibitor. An ADSS inhibitor refers to an agent that inhibits the expression or activity of ADSS, and/or reduces the level of ADSS. That is, in various embodiments, an ADSS inhibitor may inhibit the expression of the ADSS protein, e.g., by inhibiting translation of the ADSS mRNA into the ADSS protein. In some embodiments, an ADSS inhibitor inhibits the activity of ADSS, such as by binding to ADSS and interfering with its enzymatic activity.

In some embodiments, the S-AMP modulator is an adenylosuccinate lyase activator. An adenylosuccinate lyase activator refers to an agent that increases the expression, level, or activity of adenylosuccinate lyase. That is, in various embodiments, an adenylosuccinate lyase activator may involve expressing adenylosuccinate lyase in a cell, such as by administering a nucleic acid encoding adenylosuccinate lyase. An adenylosuccinate lyase activator may also be an inhibitor of a cellular factor that itself inhibits adenylosuccinate lyase, such as a microRNA.

1. Exemplary ADSS Inhibitors

In various embodiments, an adenylosuccinate synthetase (ADSS) inhibitor is an agent that inhibits the expression or activity, and/or reduces the level of ADSS. An ADSS inhibitor may, in various embodiments, be a small molecule, a peptide, an siRNA, or an antisense oligonucleotide.

In some embodiments, an ADSS inhibitor is a small molecule. A small molecule ADSS inhibitor may, in some embodiments, bind to the active site of ADSS and compete for binding of the natural substrates, such as IMP and/or L-aspartate. In some embodiments, a small molecule ADSS inhibitor is an IMP mimic. In some embodiments, a small molecule inhibitor is an L-aspartate mimic.

In some embodiments, an ADSS inhibitor is a peptide. A peptide is a polymeric compound of amino acids comprising up to 300 amino acid units linked by amide bonds. In some embodiments, a peptide inhibitor comprises fewer than 200, fewer than 100, fewer than 50, fewer than 40, fewer than 30, fewer than 20, or fewer than 10 amino acids. In some embodiments, a peptide inhibitor comprises 2-200 amino acids, or 2-100 amino acids, or 2-50 amino acids, or 2-30 amino acids, or 10-300 amino acids, or 10-200 amino acids, or 10-100 amino acids, or 10-50 amino acids. The amino acids of a peptide may be natural, non-natural, and/or modified. In some embodiments, a peptide ADSS inhibitor comprises an L-aspartate or L-aspartate mimic and competitively inhibits binding of ADSS substrate L-aspartate.

In some embodiments, an ADSS inhibitor is an antisense oligonucleotide. Antisense oligonucleotides are well known in the art. Antisense oligonucleotides are typically 8-50, 8-40, or 8-30 nucleosides long and, in some embodiments, comprise one or more modified nucleosides and/or modified base moieties and/or modified internucleoside linkages. In some embodiments, an antisense oligonucleotide mediates RNaseH activity, which causes degradation of the target mRNA. Antisense oligonucleotides are reviewed, for example, in Antisense Drug Technology, Ed. Stanley T. Corrke, CRC Press, 2007.

In some embodiments, an ADSS inhibitor is an siRNA. siRNAs are double-stranded oligonucleotides in which one strand has a nucleobase sequence that permits hybridization to a corresponding segment of a target nucleic acid. siRNAs may comprise various modifications. Such modifications, and siRNAs generally, are well known in the art. See, e.g., *siRNA Design: Methods and Protocols*, Ed. Debra J. Taxman, Springer-Verlag New York, LLC, 2013.

A nonlimiting exemplary small molecule ADSS inhibitor is L-alanosine [L-2-amino-3-(N-hydroxy-N-nitrosamino) propionic acid]. Another nonlimiting exemplary small molecule ADSS inhibitor is D,L-alanosine (3-(Hydroxynitrosoamino)-D,L-alanine). Further exemplary ADSS inhibitors include, but are not limited to, hydantocidin, hydantocidin phosphate, hydantocidin-hadacidin S hybrid inhibitor, and hydantocidin-hadacidin R hybrid inhibitor, shown below.

Further exemplary ADSS inhibitors include, but are not limited to, GE-101, GE-109, and hadacidin, shown below.

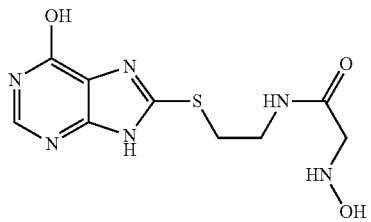

GE-101

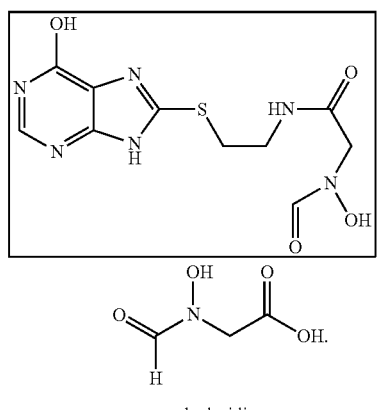

GE-109 hadacidin

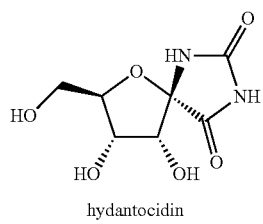

hydantocidin

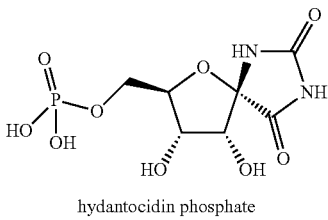

hydantocidin phosphate

Further exemplary ADSS inhibitors include AdSS-1 and AdSS-2:

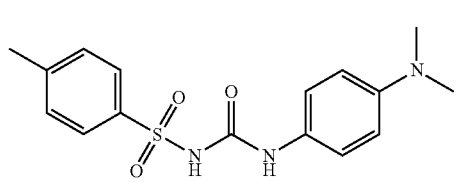

AdSS-1

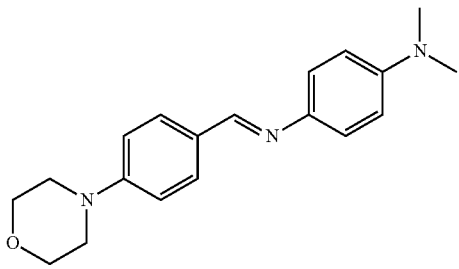

AdSS-2

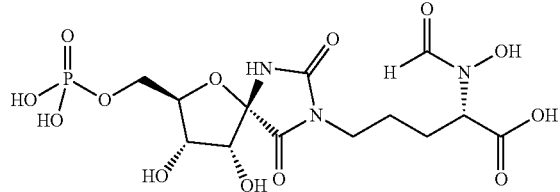

hydantocidin-hadacidin S-hybrid inhibitor

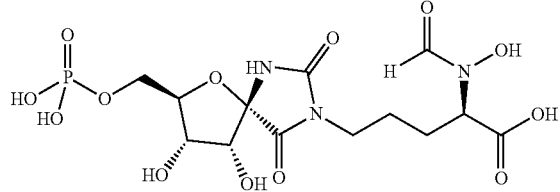

hydantocidin-hadacidin R-hybrid inhibitor

Further exemplary ADSS inhibitors include compounds having structure A:

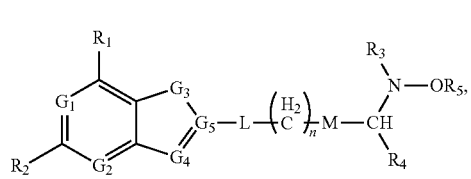

A wherein each of $R_1$ and $R_2$ is independently selected from the group consisting of —H, a halogen, —$NH_2$, —OH, —NH—$R_3$, and —O—$R_3$;

each of $G_1$, $G_2$, and $G_4$, is independently selected from the group consisting of CH, N, O, and S, or $G_4$ is independently C=O group;

$G_3$ is independently selected from the group consisting of $CH_2$, NH, O, C=O group and S;

$G_5$ is independently selected from the group consisting of C and N;

L is absent or is selected from the group consisting of O, NH, and S;

$R_3$ is selected from a group consisting of —H, an $C_1$-$C_{18}$ alkyl, an aryl, —C(O)—H, and —C(O)-alkyl;

$R_4$ is selected from a group consisting of —H, —C(O)O—, and —C(O)—$R_3$;

$R_5$ is selected from a group consisting of —H, an $C_1$-$C_{18}$ alkyl, and an aryl;

M is absent or is selected from the group consisting of —$CH_2$—; —NH—; —NH—C(O)—; —O—, and —S—; and n is an integer having the value between 1 and 6.

In some embodiments, $G_1$, $G_2$, and $G_4$ are N, $G_3$ is NH, and $G_5$ is C.

Various ADSS inhibitors are known in the art and are described, for example, in PCT Publication Nos. WO 2009/023495A2 and WO 92/07569; Crowther et al., 2011, *Mol. Biol. Parisitol.*, 175: 21-29; and Hanessian et al., 1999, *Angew Chem Int Ed* 38: 3159-62.

2. Exemplary Adenylosuccinate Lyase Activators

In various embodiments, an adenylosuccinate lyase activator is an agent that increases the expression, level and/or activity of adenylosuccinate lyase. In various embodiments, an adenylosuccinate lyase activator may involve expressing adenylosuccinate lyase in a cell, such as by administering a nucleic acid encoding adenylosuccinate lyase. Administering a nucleic acid encoding adenylosuccinate lyase may comprise gene therapy, for example. Gene therapy strategies are reviewed, for example, in Naldini, 2015, *Nature*, 526: 351-360.

In some embodiments, an adenylosuccinate lyase activator may also be an inhibitor of a cellular factor that itself inhibits adenylosuccinate lyase, such as a microRNA. For example, an antisense oligonucleotide that targets a microRNA that inhibits adenylosuccinate lyase will result in an increase in adenylosuccinate lyase levels.

B. Exemplary S-Ado Reducing Agents

In various embodiments, methods comprise administering to a subject with an autism spectrum disorder, or a subject suspected of having an autism spectrum disorder, or a subject predicted to develop an autism spectrum disorder, or a subject at risk for developing an autism spectrum disorder, a succinyl-adenosine reducing agent (S-Ado reducing agent). In various embodiments, the subject has been identified as having an autism spectrum disorder, or suspected of having an autism spectrum disorder, or predicted to develop an autism spectrum disorder, or at risk for developing an autism disorder, using any diagnostic criteria in the art or described herein. In various embodiments, the S-Ado reducing agent reduces the level of S-Ado and/or its metabolites outside of cells. In various embodiments, the S-Ado reducing agent may sequester S-Ado and/or its metabolites and/or cause degradation of S-Ado and/or its metabolites.

In some embodiments, an S-Ado reducing agent is an antibody that binds S-Ado and/or one or more of its metabolites. In some embodiments, an S-Ado reducing agent is an antibody that binds S-Ado. In some such embodiments, by binding S-Ado and/or one or more of its metabolites, and antibody reduces or eliminates one or more negative effects of S-Ado and/or one or more of its metabolites. As noted herein, the term "antibody" includes various antibody structures, including but not limited to monoclonal antibodies, polyclonal antibodies, multispecific antibodies (e.g., bispecific antibodies), and antibody fragments so long as they exhibit the desired antigen-binding activity. In some embodiments, an S-Ado reducing agent is an abzyme.

C. Exemplary AMPK Modulators

In various embodiments, methods comprise administering to a subject with an autism spectrum disorder, or a subject suspected of having an autism spectrum disorder, or a subject predicted to develop an autism spectrum disorder, or a subject at risk for developing an autism spectrum disorder, an AMPK modulator. In various embodiments, the subject has been identified as having an autism spectrum disorder, or suspected of having an autism spectrum disorder, or predicted to develop an autism spectrum disorder, or at risk for developing an autism disorder, using any diagnostic criteria in the art or described herein. In various embodiments, the AMPK modulator reduces the amount or activity of AMPK. In some embodiments, the activity of AMPK is modulated by the administration of an AMPK inhibitor. In some embodiments, the amount of AMPK is modulated by decreasing the amount of AMP.

In some embodiments, the AMPK inhibitor is an antisense oligonucleotide, an siRNA, a peptide, or a small molecule.

In some embodiments, an AMPK inhibitor is a small molecule. A small molecule AMPK inhibitor may, in some embodiments, bind to AMPK and compete for binding of the natural ligand(s), such as AMP. In some embodiments, a small molecule AMPK inhibitor is an AMP mimic. Non-limiting exemplary AMPK inhibitors include dorsomorphin, such as dorsomorphin hydrochloride.

In some embodiments, an AMPK inhibitor is a peptide. A peptide is a polymeric compound of amino acids comprising up to 300 amino acid units linked by amide bonds. In some embodiments, a peptide inhibitor comprises fewer than 200, fewer than 100, fewer than 50, fewer than 40, fewer than 30, fewer than 20, or fewer than 10 amino acids. In some embodiments, a peptide inhibitor comprises 2-200 amino acids, or 2-100 amino acids, or 2-50 amino acids, or 2-30 amino acids, or 10-300 amino acids, or 10-200 amino acids, or 10-100 amino acids, or 10-50 amino acids. The amino acids of a peptide may be natural, non-natural, and/or modified. In some embodiments, a peptide AMPK inhibitor competitively inhibits binding of AMPK to a ligand.

In some embodiments, an AMPK inhibitor is an antisense oligonucleotide. Antisense oligonucleotides are well known in the art. Antisense oligonucleotides are typically 8-50, 8-40, or 8-30 nucleosides long and, in some embodiments, comprise one or more modified nucleosides and/or modified base moieties and/or modified internucleoside linkages. In some embodiments, an antisense oligonucleotide mediates RNaseH activity, which causes degradation of the target mRNA. Antisense oligonucleotides are reviewed, for example, in Antisense Drug Technology, Ed. Stanley T. Corrke, CRC Press, 2007.

In some embodiments, an AMPK inhibitor is an siRNA. siRNAs are double-stranded oligonucleotides in which one strand has a nucleobase sequence that permits hybridization to a corresponding segment of a target nucleic acid. siRNAs may comprise various modifications. Such modifications, and siRNAs generally, are well known in the art. See, e.g., *siRNA Design: Methods and Protocols*, Ed. Debra J. Taxman, Springer-Verlag New York, LLC, 2013.

In some embodiments, an AMPK modulator inhibits AMPK amount and/or activity by reducing the level of AMP (an AMP reducing agent). In some embodiments, an AMP reducing agent is an antibody that binds AMP. In some embodiments, an AMP reducing agent is an abzyme. In some embodiments, an AMP reducing agent increases the activity or amount of an enzyme that drives conversion of AMP to another molecule. For example, in some embodiments, an AMP reducing agent increases the activity or amount of adenylate kinase (which converts AMP+ATP to 2 ADP), ATP synthase (which converts ADP to ATP), myoadenylate deaminase (which converts AMP to IMP), and/or nucleotidase (which converts AMP to adenosine).

D. Exemplary Pharmaceutical Compositions and Routes of Administration

In some embodiments, compositions comprising one or more of the therapeutic agents provided herein are provided in formulations with a wide variety of pharmaceutically acceptable carriers (see, for example, Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In some embodiments, pharmaceutical compositions are administered in an amount effective for treatment of (including prophylaxis of) an autism spectrum disorder. The therapeutically effective amount is typically dependent on the weight of the subject being treated, his or her physical or health condition, the extensiveness of the condition to be treated, or the age of the subject being treated.

A therapeutic agent provided herein may be administered in vivo by various routes, including, but not limited to, intravenous, intra-arterial, parenteral, intraperitoneal or subcutaneous. The appropriate formulation and route of administration may be selected according to the particular therapeutic agent and intended application.

A therapeutic agent provided herein may be administered in conjunction with a low purine diet.

III. Exemplary Diagnostic Methods

In some embodiments, a method of identifying a subject who would benefit from treatment with an S-AMP modulator and/or low purine diet is provided. In some such embodiments, the method comprises determining the level of S-Ado in a sample from the subject, wherein an elevated level of S-Ado in the sample indicates the subject would benefit from treatment with an S-AMP modulator and/or low purine diet. In some embodiments, the level of S-Ado in the sample is compared to a reference level of S-Ado. The level of S-Ado may be determined in a sample selected from a blood, plasma, urine, and/or CSF sample. In various embodiments, the subject may be selected for S-Ado testing because they have been identified as having an autism spectrum disorder, or suspected of having an autism spectrum disorder, or predicted to develop an autism spectrum disorder, or at risk for developing an autism spectrum disorder. Such identifications may be made on the basis of any criteria in the art for identifying such subjects, and may include, for example, neurological assessments, genetic assessments, cognitive testing and/or language testing. In some embodiments, a subject is identified using the Autism-Diagnosis Interview-Revised (ADI-R), the Autism Diagnostic Observation Schedule (ADOS-G), and/or the Childhood Autism Rating Scale (CARS).

In some embodiments, a method of identifying a subject who would benefit from treatment with an S-AMP modulator and/or a low purine diet comprises determining whether the subject has a 16p11.2 deletion, wherein a 16p11.2 deletion indicates the subject would benefit from treatment with an S-AMP modulator and/or a low purine diet.

In some embodiments, a method of identifying a subject who would benefit from treatment with an S-AMP modulator and/or a low purine diet comprises determining whether the subject has a mutation in the KCTD13 gene, wherein a mutation in the KCTD13 gene indicates the subject would benefit from treatment with an S-AMP modulator and/or a low purine diet. In some embodiments, the mutation in the KCTD13 gene is a loss-of-function mutation. In some embodiments, the mutation in the KCTD13 gene is a partial or total deletion of the KCTD13 gene.

In some embodiments, a method of identifying a subject who would benefit from treatment with an S-AMP modulator and/or a low purine diet comprises determining whether the subject has a mutation in the CUL3 gene, wherein a mutation in the CUL3 gene indicates the subject would benefit from treatment with an S-AMP modulator and/or a low purine diet. In some embodiments, the mutation in the CUL3 gene is a loss-of-function mutation. In some embodiments, the mutation in the CUL3 gene is a partial or total deletion of the CUL3 gene.

A method of identifying a subject who would benefit from treatment with an S-AMP modulator and/or a low purine diet may comprise any combination of determining the level of S-Ado in a sample from the subject, determining whether the subject has a 16p11.2 deletion, determining whether the subject has a mutation in the KCTD13 gene, determining whether the subject has a mutation in the CUL3 gene, and/or determining whether the subject exhibits autism spectrum disorder symptoms, or is otherwise predicted to develop an autism spectrum disorder or at risk of developing an autism spectrum disorder.

In some embodiments, the subject exhibits at least one symptom of an autism spectrum disorder. In some embodiments, at least one symptom of an autism spectrum disorder is selected from development delay, intellectual disability, seizures, and increased risk of obesity; social interaction deficit; language impairment; repetitive behaviors; sleep disorder; mood disorder; anxiety; gastrointestinal symptoms; hyperactivity; and attention deficits. In some embodiments, the subject has been previously diagnosed as having an autism spectrum disorder.

In some embodiments, the subject does not have an adenylosuccinate lyase (ADSL) deficiency.

A. Exemplary Methods of Detecting Nucleic Acid Variations

Methods of determining presence of genomic variations, such as 16p11.2 deletions, mutations in the KCTD13 gene, and/or mutations in the CUL3 gene in a sample from a subject are known in the art. For example, assays for detection of specific variations, using real-time PCR are known (available from, for example, Qiagen, Valencia, Calif.).

A nucleic acid, may be e.g., genomic DNA, RNA transcribed from genomic DNA, or cDNA generated from RNA. A nucleic acid may be derived from a vertebrate, e.g., a mammal. A nucleic acid is said to be "derived from" a particular source if it is obtained directly from that source or if it is a copy of a nucleic acid found in that source.

Variations in nucleic acids and amino acid sequences may be detected by certain methods known to those skilled in the art. Such methods include, but are not limited to, DNA sequencing; primer extension assays, including allele-specific nucleotide incorporation assays and allele-specific primer extension assays (e.g., allele-specific PCR, allele-specific ligation chain reaction (LCR), and gap-LCR); allele-specific oligonucleotide hybridization assays (e.g., oligonucleotide ligation assays); cleavage protection assays in which protection from cleavage agents is used to detect mismatched bases in nucleic acid duplexes; analysis of MutS protein binding; electrophoretic analysis comparing the mobility of variant and wild type nucleic acid molecules; denaturing-gradient gel electrophoresis (DGGE, as in, e.g., Myers et al. (1985) Nature 313:495); analysis of RNase cleavage at mismatched base pairs; analysis of chemical or enzymatic cleavage of heteroduplex DNA; mass spectrometry (e.g., MALDI-TOF); genetic bit analysis (GBA); 5' nuclease assays (e.g., TaqMan®); and assays employing molecular beacons. Certain of these methods are discussed in further detail below.

Detection of variations in target nucleic acids may be accomplished by molecular cloning and sequencing of the target nucleic acids using techniques known in the art. Alternatively, amplification techniques such as the polymerase chain reaction (PCR) can be used to amplify target nucleic acid sequences directly from a genomic DNA preparation from tissue. The nucleic acid sequence of the amplified sequences can then be determined and variations identified therefrom. Amplification techniques are known in the art, and include, for example, the polymerase chain reaction (PCR).

In various embodiments, the ligase chain reaction may be used to amplify target nucleic acid sequences. See, e.g., Wu et al., Genomics 4:560-569 (1989). In addition, allele-specific PCR may be used to detect variations (e.g., substitutions) in a nucleic acid sequence. See, e.g., Ruano and Kidd (1989) Nucleic Acids Research 17:8392; McClay et al. (2002) Analytical Biochem. 301:200-206. In some embodiments of this technique, an allele-specific primer is used in which the 3' terminal nucleotide of the primer is complementary to (i.e., capable of specifically base-pairing with) a particular variation in the target nucleic acid. If the particular variation is not present, an amplification product is not observed. In some embodiments, amplification Refractory Mutation System (ARMS) can also be used to detect variations (e.g., substitutions). ARMS is described, e.g., in European Patent Application Publication No. 0332435, and in Newton et al., Nucleic Acids Research, 17:7, 1989.

Other methods useful for detecting variations (such as substitutions or deletions) include, but are not limited to, (1) allele-specific nucleotide incorporation assays, such as single base extension assays (see, e.g., Chen et al. (2000) Genome Res. 10:549-557; Fan et al. (2000) Genome Res. 10:853-860; Pastinen et al. (1997) Genome Res. 7:606-614; and Ye et al. (2001) Hum. Mut. 17:305-316); (2) allele-specific primer extension assays (see, e.g., Ye et al. (2001) Hum. Mut. 17:305-316; and Shen et al. Genetic Engineering News, vol. 23, Mar. 15, 2003), including allele-specific PCR; (3) 5'nuclease assays (see, e.g., De La Vega et al. (2002) BioTechniques 32:S48-S54 (describing the TaqMan® assay); Ranade et al. (2001) Genome Res. 11:1262-1268; and Shi (2001) Clin. Chem. 47:164-172); (4) assays employing molecular beacons (see, e.g., Tyagi et al. (1998) Nature Biotech. 16:49-53; and Mhlanga et al. (2001) Methods 25:463-71); and (5) oligonucleotide ligation assays (see, e.g., Grossman et al. (1994) Nuc. Acids Res. 22:4527-4534; patent application Publication No. US 2003/0119004 A1; PCT International Publication No. WO 01/92579 A2; and U.S. Pat. No. 6,027,889).

Variations may also be detected by mismatch detection methods. Mismatches are hybridized nucleic acid duplexes which are not 100% complementary. The lack of total complementarity may be due to deletions, insertions, inversions, or substitutions. One example of a mismatch detection method is the Mismatch Repair Detection (MRD) assay described, e.g., in Faham et al., Proc. Natl Acad. Sci. USA 102:14717-14722 (2005) and Faham et al., Hum. Mol. Genet. 10:1657-1664 (2001). Another example of a mismatch cleavage technique is the RNase protection method, which is described in Winter et al., Proc. Natl. Acad. Sci. USA, 82:7575, 1985, and Myers et al., Science 230:1242, 1985. For example, a method of the invention may involve the use of a labeled riboprobe which is complementary to the human wild-type target nucleic acid. The riboprobe and target nucleic acid derived from the tissue sample are annealed (hybridized) together and subsequently digested with the enzyme RNase A, which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of the target nucleic acid, but can be a portion of the target nucleic acid, provided it encompasses the position suspected of having a variation.

In a similar manner, DNA probes can be used to detect mismatches, for example through enzymatic or chemical cleavage. See, e.g., Cotton et al., Proc. Natl. Acad. Sci. USA, 85:4397, 1988; and Shenk et al., Proc. Natl. Acad. Sci. USA, 72:989, 1975. Mismatches may also be detected by shifts in the electrophoretic mobility of mismatched duplexes relative to matched duplexes. see, e.g., Cariello, Human Genetics, 42:726, 1988. With either riboprobes or DNA probes, the target nucleic acid suspected of comprising a variation may be amplified before hybridization. Changes in target nucleic acid can also be detected using Southern hybridization, especially if the changes are gross rearrangements, such as deletions and insertions.

In some embodiments, restriction fragment length polymorphism (RFLP) probes for the target nucleic acid or surrounding marker genes can be used to detect variations, e.g., insertions or deletions. Insertions and deletions may also be detected by cloning, sequencing and amplification of a target nucleic acid. Single stranded conformation polymorphism (SSCP) analysis can also be used to detect base change variants of an allele. See, e.g., Orita et al., Proc. Natl. Acad. Sci. USA 86:2766-2770, 1989, and Genomics, 5:874-879, 1989.

In some embodiments, a genomic deletion may be determined using deletion analysis. In some embodiments, the deletion may be genotyped based on genomic testing that determines the copy number of sequences, such as chromosomal microarray (CMA) or fluorescence in situ hybridization (FISH). In some embodiments, a genomic deletion may be determined using multiplex ligation-dependent probe amplification (MLPA). In some embodiments, a commercially available service for determining a genomic deletion may be used (e.g., CGC Genetics).

In some embodiments, compositions suitable for use in performing the methods described herein are provided. For example, arrays are provided that can be used in such methods. In some embodiments, an array comprises individual or collections of nucleic acid molecules useful for detecting variations. For instance, an array may comprise a series of discretely placed individual allele-specific oligonucleotides or sets of allele-specific oligonucleotides. Several techniques are known in the art for attaching nucleic acids to a solid substrate such as a glass slide. One method is to incorporate modified bases or analogs that contain a reactive moiety that is capable of attachment to a solid substrate, such as an amine group, a derivative of an amine group, or another group with a positive charge, into nucleic acid molecules that are synthesized. The synthesized product is then contacted with a solid substrate, such as a glass slide coated with an aldehyde or other reactive group. The aldehyde or other reactive group will form a covalent link with the reactive moiety on the amplified product, which will become covalently attached to the glass slide. Other methods, such as those using amino propryl silican surface chemistry are also known in the art.

The presence of 16p11.2 deletions, mutations in the KCTD13 gene, and/or mutations in the CUL3 gene according to any of the methods described herein may be determined using any suitable biological sample obtained from a subject. Biological samples may be obtained from vertebrate animals, and in particular, humans.

B. Exemplary Methods of Determining S-Ado Levels

In some embodiments, levels of succinyladenosine (S-Ado) and/or its metabolites are determined in extracellular fluids such as blood, plasma, cerebrospinal fluid and/or urine. Any method of determining S-Ado levels may be used. Nonlimiting exemplary methods of detecting S-Ado and/or its metabolites include, but are not limited to, HPLC with UV detection or HPLC-MS. See, e.g., Jurecka et al., 2015, *J. Inherit. Metab. Dis.* 38: 231-242). In some embodiments, a Bratton-Marshall assay (using N-1-naphthyl ethylene diamine dihydrochloride) and thin-layer chromatography (TLC) is used to identify S-Ado in urine, cerebrospinal fluid, blood and/or plasma. See, e.g., Jaeken, *J. Inherit. Metab. Dis.* 15: 416-418, 1992. In some embodiments, the Bratton-Marshall test and TLC with Pauly reagent detects the presence of urinary S-Ado. In some embodiments, high-performance liquid chromatography with photodiode array detection (HPLC-DAD) can resolve S-Ado from serum, urine, blood and/or CSF by reverse-phase high-pressure liquid chromatography (RP-HPLC) with detection by UV spectroscopy. In some embodiments, levels of S-Ado and/or its metabolites can be measured using HPLC combined with electrospray ionization tandem mass spectrometry.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1. Generation of Kctd13Δ47 Mice

As the role of ubiquitin ligase pathways in schizophrenia and autism is unclear, a mouse model of alteration in expression of KCTD13 was developed. KCTD13 is a substrate-specific adapter of a BTB-CUL3-RBX1 (BCR) E3 ubiquitin-protein ligase complex involved in regulation of cytoskeleton structure.

The CRISPR/Cas9 system guide RNAs targeting the first exon of Kctd13 were used to create a deletion in exon 1 of the mouse Kctd13 gene (NCBI Gene ID 233877). Out of frame deletion in exon 1 of Kctd13 would be expected to result in edited sequences that do not produce any protein products.

A. In Vitro Validation of Single Guide RNAs (sgRNAs)

sgRNAs were designed using the CRISPRtool (crispr.mit.edu), the sequences of which were screened for Kctd13 are (sgRNA1 is the one that made the mouse) SEQ ID Nos: 1-3 (Table 1). To validate sgRNA targeting of the Kctd13 locus, U6-sgRNA PCR products were generated using Herculase II DNA polymerase (Agilent), purified using QIAquick PCR Purification Kit (Qiagen), and co-transfected with a Cas9 expression plasmid into mouse N2a cells (ATCC) using Lipofectamine 2000 (Life Technologies). Three days after transfection, genomic DNA was extracted with QuickExtract DNA Extraction Solution (Epicenter) and used as a template for PCR amplification with Herculase II DNA polymerase (Agilent). PCR amplicons were purified, and 200 ng was used as an input into the SURVEYOR assay (Transgenomic), run on a 2% E-gel (Life Technologies), and quantified using relative band intensities.

TABLE 1 sgRNAs designed for Kctd13

| SEQ ID NO | Description | Sequence |
|---|---|---|
| 1 | sgRNA1 | gccggctgcggccgaatgct |
| 2 | sgRNA2 | aggggcttcagactgtacga |
| 3 | sgRNA3 | caccacgctgcgcaccctca |

B. Preparation of Cas9 mRNA and sgRNA RNA for Zygote Injection

Human codon optimized Cas9 (from *Streptococcus pyogenes*) capped and polyadenylated mRNA was prepared by in vitro transcription using mMessage mMachine T7 ULTRA Transcription Kit (Ambion). sgRNA RNA was prepared by in vitro transcription using Megashortscript T7 Transcription Kit (Ambion) with an annealed partially double stranded template (Table 2).

TABLE 2 sgRNA sequences

| SEQ ID NO | Description | Sequence |
|---|---|---|
| 8 | Reverse sgRNA IVT primer 1 | Aaaaaagcac cgactcggtg ccacttttttc aagctgataa cggactagcc ttattttaac ttgctatttc tagctctaaa acagcattcg gccgcagccg gccctatagt gagtcgtatt a |
| 9 | Reverse sgRNA IVT primer 2 | Aaaaaagcac cgactcggtg ccacttttttc aagttgataa cggactagcc ttattttaac ttgctatttc tagctctaaa actcgtacag tctgaagccc ctccctatag tgagtcgtat ta |
| 10 | Reverse sgRNA IVT primer 3 | Aaaaaagcac cgactcggtg ccacttttttc aagttgataa cggactagcc ttattttaac ttgctatttc tagctctaaa actgagggtg cgcagcgtgg tgccctatag tgAgtcgtat ta |

Both Cas9 mRNA and sgRNA RNA were purified by MEGAclear Transcription Clean-Up Kit (Ambion) and mixed to a final concentration of 200 ng/μl Cas9 mRNA and 50 ng/μl sgRNA RNA in $H_2O$ for injection.

C. Generation of Germline Mutant Mice

Three-five week old C57BL/6N (Taconic) female mice (superovulation and plugged 0.5 dpc) were used as zygote donors and CD-1(ICR) females were used as foster mothers. Three days prior to zygote injections, pregnant mare's serum (PMS) 5 IU was administered IP to each donor female. Forty-seven hours later hCG 5 IU was administered by IP injection and then females were paired with stud males. Donor females were sacrificed 0.5 pcd and ovaducts were collected and placed into 0.1% hyaluronidase/flushing holding media (FHM) (Millipore). Using two pairs of forceps the swollen ampulla was torn open releasing the eggs/cumulus cell bunch. The zygotes were washed in drops of FHM and the cumulus cells were removed and put into KSOM-aa culture medium (Millipore) for an hour before injection. 5 μl of Cas9/sgRNA RNA mixture was loaded into a microinjection needle (prepared by Needle puller Sutter P-97) and attached to the microinjector (Eppendorf microinjector 5242). Sets of eggs were placed into 100 μl FHM drops covered with mineral oil at room temperature. The larger pronucleus was injected until an obvious expansion occurred. Eggs were placed back into the warm and equilibrated KSOM-aa culture medium and incubated overnight. Twelve hours later the two-cell stage embryos were surgically implanted bilaterally into the oviducts of 0.5 dpc CD-1 recipients. A maximum of 26 two-cell embryos were transferred into one recipient and monitored for pregnancy. To identify progeny that contained indels in the targeted Kctd13 exon, the genotyping primers Kctd13 forward primer 1 (SEQ ID NO: 4) and Kctd13 reverse primer 2 (SEQ ID No: 6) were used.

TABLE 3

Primers for identification of edited products

| SEQ ID NO | Description | Sequence |
|---|---|---|
| 4 | Kctd13 forward primer 1 | cggagtagct gtggagagtg g |
| 5 | Kctd13 reverse primer 1 | AAAAAAAGCA CCGACTCGGT GCCACTTTTT CAAGTTGATA Acggactagc cttattttaa cttgCTATTT CTAGCTCTAA AACagcattc ggccgcagcc ggcggtgTTT CGTCCTTTCC ACaag |
| 6 | Kctd13 reverse primer 2 | AAAAAAAGCA CCGACTCGGT GCCACTTTTT CAAGTTGATA Acggactagc cttattttaa cttgCTATTT CTAGCTCTAA AACtcgtaca gtctgaagcc cctCggtgTT TCGTCCTTTC CACaag |
| 7 | Kctd13 reverse primer 3 | AAAAAAAGCA CCGACTCGGT GCCACTTTTT CAAGTTGATA Acggactagc cttattttaa cttgCTATTT CTAGCTCTAA AACtgagggt gcgcagcgtg gtgCggtgTT TCGTCCTTTC CACaag |

D. Genotyping kctd13Δ47 Mice

During the course of working with the kctd13Δ47 mice, an amplification bias was found that made genotyping heterozygote mice difficult. A primer pair and probe was developed suitable for droplet digital PCR that allowed accurately genotyping all allelic combinations of the kctd13Δ47 allele. The genotyping primers were SEQ ID NOs: 14-16.

TABLE 4 kctd13.447 genotyping probe set

| SEQ ID NO | Description | Sequence |
|---|---|---|
| 14 | Kctd13 F 47_64 nt | tccgctcactggcatgtc |
| 15 | Kctd13 R 47_64 nt | cacactcgaggggctagg |

TABLE 4-continued kctd13.447 genotyping probe set

| SEQ ID NO | Description | Sequence |
|---|---|---|
| 16 | Kctd13 probe 47_64 nt | /56-FAM/tgcggccga/ZEN/atgcttggagtcc/3IABkFQ/ |

To genotype mice, genomic DNA from either ear clip or tail clips was obtained by adding 75 uL of 25 mM NaOH, 0.2 mM EDTA to the tissue and incubating for 30 minutes at 95° C. followed by neutralization with 75 uL 40 mM Tris-HCL pH5. Genotyping was carried out by mixing 1 µL of the genomic DNA mixture with the ddPCR assay and 1×ddPCR mix for Probes (Bio-Rad). Droplets were prepared according to the manufacturer's instructions in a Bio-Rad Droplet generator. Droplets were cycled according to the manufacturer's instructions. Following cycling droplets were counted in an X100 ddPCR instrument (Bio-Rad). Bio-Rad ddPCR Quantasoft software was used to determine the DNA content of each sample/genotype of each mouse.

E. Kctd13 Antibody Generation and Confirmation of Kctd13 Knockout

A peptide specific antibody was generated against the C-terminal peptide CVRRHITHDERPHGQQIVFKD-OH of KCTD13 (SEQ ID NO: 11). This peptide was injected into two New Zealand white rabbits (Dana-Farber Institute, 21$^{st}$ Century Biochemicals). The resulting serum was affinity purified against the same peptide and eluted into PBS. This polyclonal antibody, Pr2905, was used at a dilution of 1:1000 for western blots and 1:50 for immunoprecipitations.

Protein lysates were generated from mouse neurons prepared from wildtype or Kctd13Δ47 mice. C57B6 timed pregnant females were euthanized following IACUC approved method. E18 embryos were collected and rapidly decapitated. Embryos were then washed in dissection media (Hibernate-E (Hib-E, Gibco) supplemented with 100 U/mL penicillin streptomycin (Pen/Strep, Gibco)). Brains were isolated, cortices were separated from the midbrain and meninges was removed from each cortex. Each cortex was cut into six pieces; five cortices were pooled for dissociation. To dissociate 5 cortices, one Papain kit (Worthington LK3176) was reconstituted in 5 mLs Hib-E and activated at 37° C. for 10 minutes. Following activation, DNAse I (Sigma) was added to a concentration of 10 µg/mL and filter sterilized using a 0.22 µm filter. Cortices were washed twice with 5 mLs of Hib-E and 5 mLs of activated papain/DNAseI was added to the cortices and incubated for 8 minutes at 37° C. Following digestion, cortices were washed three times with 10 ml Hib-E per wash. Cortices were then triturated 10-15 times with a P1000 pipette in 1 mL NBActive4 supplemented with 10 µg/mL DNAseI filter sterilized using a 0.22 µm filter. The cell mixture was then allowed to settle for 1 minute at room temperature and the supernatant was transferred to a new tube containing 4 mLs of NBActive4 media and spun at 1K rpm for 5 minutes at room temperature. The supernatant was aspirated and the pellet was gently resuspended in 1 mL NBActive4 media. Cells were counted in a hemocytometer, diluted and plated at 1 million cells/well in a 6 well poly-D-lysine (Corning, Biocoat) or 6 million cells/10 cm poly-D-lysine plate (Corning, Biocoat).

To inhibit proteasome function, neurons were treated for 5 hours with 2 µM bortezomib in DMSO. To inhibit Cullin function, cells were treated for 5 hours with 2 µM MLN4924. Following treatments, cells were collected in ubiquitin lysis buffer (1×CST lysis buffer (Cell Signaling Technology), Phosphatase Inhibitor Cocktail 2 (PIC2; Sigma), Phosphatase Inhibitor Cocktail 3 (PIC3; Sigma), 0.1 mM chloracetimide (Sigma), 10 mM NaF (Sigma), 2 mM PMSF (Aldrich), Roche protease inhibitor mini (Roche), 50 µM PR-619 (Lifesensors), 2 mM 1,10 orthophenanthroline (Sigma)) by scraping. Lysates were sonicated with Diagenode bath sonicator for 5' and spun at 12 k for 10 minutes and supernatants were transferred to a new tube. Laemli buffer was added to samples, boiled, run on an Bis-Tris SDS PAGE gel and western transferred to a nitrocellulose membrane.

Antibodies used from western blots and immunoprecipitations were Myc-tag Rabbit mAb (CST 71D10-2278S), KCTD13 Rabbit (Pr2905), HA-tag Rabbit mAb (CST C29F4-3724S), IgG Rabbit polyclonal ChIP Grade 0.2 mg/ml (ab27478), V5-tag Rabbit mAb (CST D3H8Q-13202S), Myc-tag Mouse mAb (CST 9B11-2276S), KCTD13 (B-12) Mouse monoclonal IgG 200 ug/ml (sc-393994), KCTD13 Rabbit polyclonal Ab (21$^{st}$ Centory Biochemicals, Pr2905), HA-tag Mouse mAb (CST 6E2-2376S), Anti-V5 Antibody Mouse monoclonal 50 uL at 1.01 mg/mL (Invitrogen P/N 46-0705), and B-actin Rabbit mAb (HRP Conjugate) (CST D6A8-12620S).

Protein lysates from DIV21 cultures were run on western blots and probed with the Pr2905 antibody or glyceraldehyde 3-phosphate dehydrogenase (GAPDH) control antibodies. FIG. 1 shows knockdown of KCTD13 levels in Kctd13Δ47 mice compared to wildtype (WT), with no change in GAPDH levels.

Example 2: Proteomic and Mass Spectrometry Analysis of Kctd13Δ47 Mice

Figure 2:
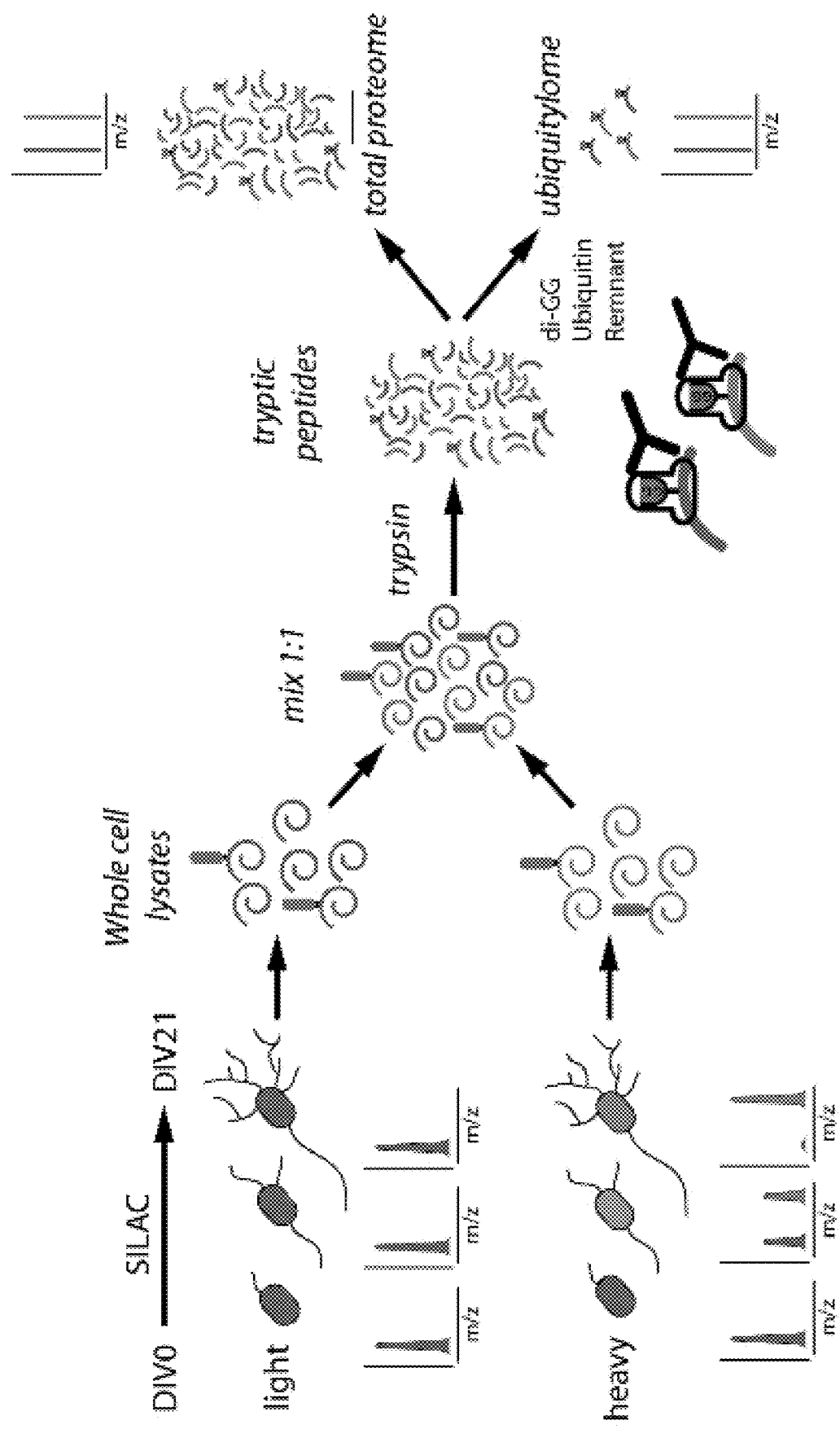
FIG. 2 shows an overview of the stable isotope labeling using amino acids in cell culture (SILAC) labeling and trypsin digestion procedures.

Experiments were designed to quantitatively compare ubiquitylomes and proteomes between wildtype and Kctd13Δ47 mice. An overview of the stable isotope labeling using amino acids in cell culture (SILAC) labeling and trypsin digestion procedures is presented in FIG. 2.

A. SILAC Labeling of Mouse Primary Neurons

Forebrains (cortex, hippocampus and striatum) were dissected from either wildtype C57B6 or Kctd13Δ47 C57B6. E18 timed pregnant females were euthanized using IACUC approved methods. Neurons were dissected and dissociated using papain as described above. Neurons were plated on 10 cM poly-D-lysine coated plates at a density of 6 million cells per plate in either heavy or light SILAC media. Neurons were fed every other day for 21 days in vitro. This feeding schedule resulted in greater than 95% labeling of cells. Neurons were then scraped into ubiquitin lysis buffer. Plates of a common genotype and metabolic labeling state were pooled for further processing. SILAC labels were flipped for each genotype. K-ε-GG and total proteome profiling were later performed for both replicates.

B. Cell Lysis and Trypsin Digestion for K-ε-GG and Proteome Profiling

SILAC-labeled neurons were lysed on plates by washing once with 10 mLs ice cold PBS and then scraping into 350 µL of ice cold urea lysis buffer (8 M urea, 50 mM Tris-HCl, pH 7.5, 150 mM NaCl, 1 mM EDTA, 2 µg/ml aprotinin (Sigma-Aldrich), 10 µg/ml leupeptin (Roche Applied Science), 1 mM phenylmethylsulfonyl fluoride (PMSF), 50 µM PR-619, and 1 mM chloroacetamide). Plates of a common genotype and label were pooled for processing. Following lysis, samples were centrifuged at 20,000×g for 15 minutes at 4° C. to remove insoluble material. Protein concentrations were determined using a bicincohoninic acid (BCA) protein assay (Pierce) and samples were mixed equitably per SILAC state. Proteins were reduced with 5 mM dithiothreitol for 45 minutes at room temperature (RT) and subsequently carbamidomethylated with 10 mM iodoacetamide for 30 min at RT in the dark. Samples were diluted to 2 M urea with 50 mM Tris-HCl, pH 7.5, and digested with sequencing grade trypsin (Promega) at 25° C. overnight using an enzyme to substrate ratio of 1:50. Digested samples were acidified to 1% formic acid (FA) (Sigma-Aldrich). Tryptic peptides were desalted on 500-mg tC18 Sep-Pak SPE cartridges (Waters). Cartridges were conditioned with 5 ml of 100% acetonitrile (MeCN), 5 ml of 50% MeCN/0.1% FA, and four times with 5 ml of 0.1% trifluoroacetic acid (TFA). Up to 15 mg of sample was loaded onto a single cartridge, and subsequently washed 3× with 5 ml of 0.1% TFA. Samples were eluted from cartridges by washing 2× with 3 ml of 50% MeCN/0.1% FA. Desalted samples were dried overnight in a Savant SC210A SpeedVac concentrator (Thermo Scientific).

C. Basic pH Reverse Phase (bRP) Fractionation

Offline bRP fractionation was completed using a custom-manufactured Zorbax 300 Extend-C18 column (9.4×250 mm, 300 Å, 5 µm, Agilent) on an Agilent 1100 series HPLC system. Approximately 15 mg of peptide sample was resuspended in 1.8 ml of basic RP solvent A (2% MeCN, 5 mM ammonium formate, pH 10), separated into 2 HPLC vials and injected with Solvent A at flow rate of 3 ml/min. A 64-min method was used for fractionation. The gradient was composed of an initial increase to 8% Solvent B (1.1% B/min) (90% MeCN, 5 mM ammonium formate), followed by a 38-minute linear phase (0.5% B/min) where the amount of solvent B was increased from 8% to 27% and ramp phases where the Solvent B amount was increased from 31% (1% B/min) to 39% (0.5% B/min), and finally to 60% (3% B/min). A total of 96 2 ml fractions were collected every 0.66 min at a flow rate of 3 ml/min. For the proteome profiling, 5% of each fraction was pooled into 22 fractions. For ubiquitination profiling, 95% of each fraction was pooled into 8 fractions using a concatenated pooling strategy. Pooled samples were dried using a SpeedVac concentrator.

D. K-ε-GG Enrichment

Samples were then enriched for the ubiquitin remnant motif (K-ε-GG). The anti-K-ε-GG antibody was obtained from the PTMScan® ubiquitin remnant motif (K-ε-GG) kit (Cell Signaling Technology). Prior to enrichment, the antibody was covalently coupled to Protein A agarose beads by chemical cross-linking with DMP. For cross-linking, the antibody bound beads were first washed 3× with 1 ml of 100 mM sodium borate, pH 9 and then incubated in 1 ml of 20 mM dimethyl pimelimidate (DMP) for 30 minutes with rotation at RT. The reaction was stopped by washing beads 2× with 1 ml of 200 mM ethanolamine, pH 8 followed by incubation for 2 hours at 4° C. with rotation. Antibody-bound beads were washed three times in 1.5 ml of ice cold immunoprecipitation (IAP) buffer (50 mM MOPS, pH 7.2, 10 mM sodium phosphate, 50 mM NaCl), resuspended in IAP buffer, and stored at 4° C. For K-ε-GG enrichment, bRP fractions we reconstituted in 1.5 ml of IAP buffer and each fraction was incubated with 32 µg of cross-linked anti-K-ε-GG antibody for 1 hour, at 4° C., while rotating. Following incubation, samples were spun down at 2000×g and the supernatant was removed. Antibody-bound beads were washed 4× with 1.5 ml of ice cold PBS and peptides were then eluted from the beads with 2×50 µl of 0.15% TFA. Eluted peptides were desalted using C18 StageTips. Each 8 StageTip was packed with two plugs of C18 material (Empore™ C18 Extraction Disk; 3M) and then conditioned with 100 µl of MeOH, 100 µl of 50% MeCN/0.1% FA, and 2× with 100 µl of 0.1% FA. K-ε-GG peptides were loaded onto the conditioned StageTips, washed 2× with 100 µl of 0.1% FA, eluted with 50 µl of 50% MeCN/0.1% FA, and dried to completeness.

E. LC-MS/MS Analysis

K-ε-GG and global proteome fractions were reconstituted in 8 µl and 20 µl of 3% MeCN/1% FA, respectively, and analyzed by nanoflow-UPLC-HCD-MS/MS using a Q Exactive mass spectrometer (Thermo Fisher Scientific) coupled on-line to a Proxeon Easy-nLC 1000 system. 4 µl and 1 µl of K-ε-GG and global proteome samples was injected, respectively, for each analysis. Samples were injected onto a microcapillary column (360 µm OD×75 µm ID) packed with 24 cm of ReproSil-Pul C18-AQ 1.9 µm beads (Dr. Maisch GmbH) that was equipped with an integrated electrospray emitter tip (10 µm). For online analyses, the column was heated to 50 C using a 20 cm column heater (Phoenix S&T). For LC separation, solvent A was 0.1% FA/3% MeCN and solvent B was 90% MeCN/0.1% FA. Peptides were eluted into the mass spectrometer at a flow rate of 200 nl/min using a gradient consisting of a linear phase at 0.3% B/min, followed by a ramp to 60% B (10% B/min). The total analysis time for each sample was 150 minutes. The Q Exactive instrument was operated in the data-dependent mode acquiring HCD MS/MS scans (R=17,500) after each MS1 scan (R=70,000) on the 12 top most abundant ions using an MS1 ion target of 3×106 ions and an MS2 target of 5×104 ions. The maximum ion time utilized for the MS/MS scans was 120 ms; the HCD-normalized collision energy was set to 25; the dynamic exclusion time was set to 20 s, and the peptide match and isotope exclusion functions were enabled.

F. K-ε-GG and Proteome MS Data Analysis

MS data was analyzed with the MaxQuant software version 1.3.0.5 and searched against the mouse Uniprot database that contained 248 common laboratory contaminants was provided by the MaxQuant software package. The search parameters were as follows: enzyme specificity was set to trypsin, maximum number of mixed cleavages set to 2, precursor mass tolerance was at 20 ppm for the first search, and set to 6 ppm for the main search. Oxidized methionines and N-terminal protein acetylation were searched as variable modifications, with carbamidomethylation of cysteines searched as a fixed modification. For searching K-ε-GG data files, Gly-Gly addition to lysines was also searched as a variable modification. The minimum peptide length was set to 6, and false discovery rate for peptide, protein, and site identification was set to 1%. The filter labeled amino acids and peptide quantification functions were enabled. For proteome data, proteins were considered in the dataset if they were identified by 2 or more razor/unique peptides and quantified by 3 or more ratio counts in both biological replicates. For the K-ε-GG data, K-ε-GG sites were considered if they were confidently localized (>0.75) and quantified in both biological replicates.

G. Identification of Adenylosuccinate Synthetase (ADSS) as a Target Regulated by Kctd13

Figure 3:
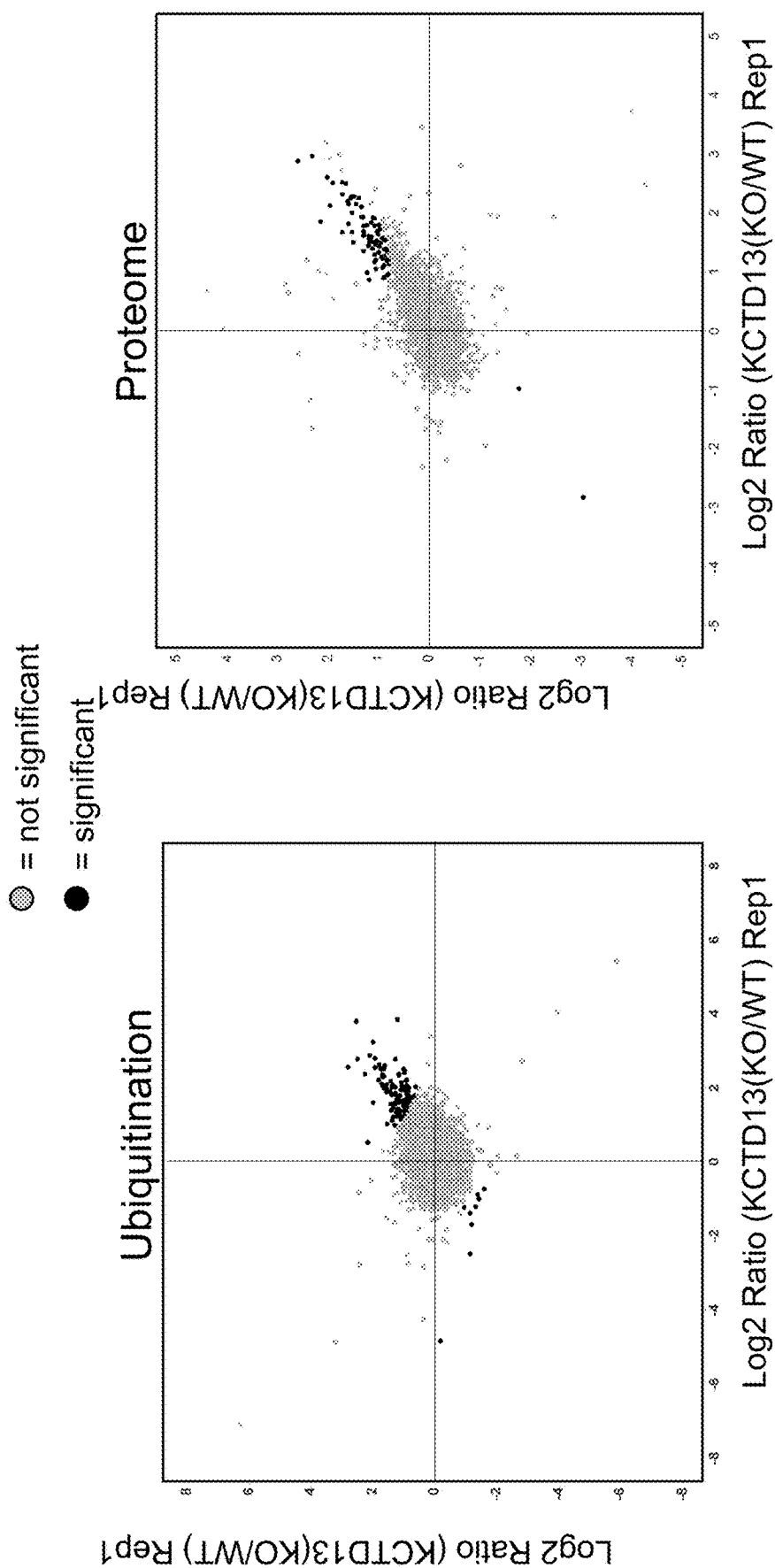
FIGS. 3A-3B show ubiquitination (A) and proteome (B) analysis of Kctd13Δ47 mice compared to WT.
Figure 4:
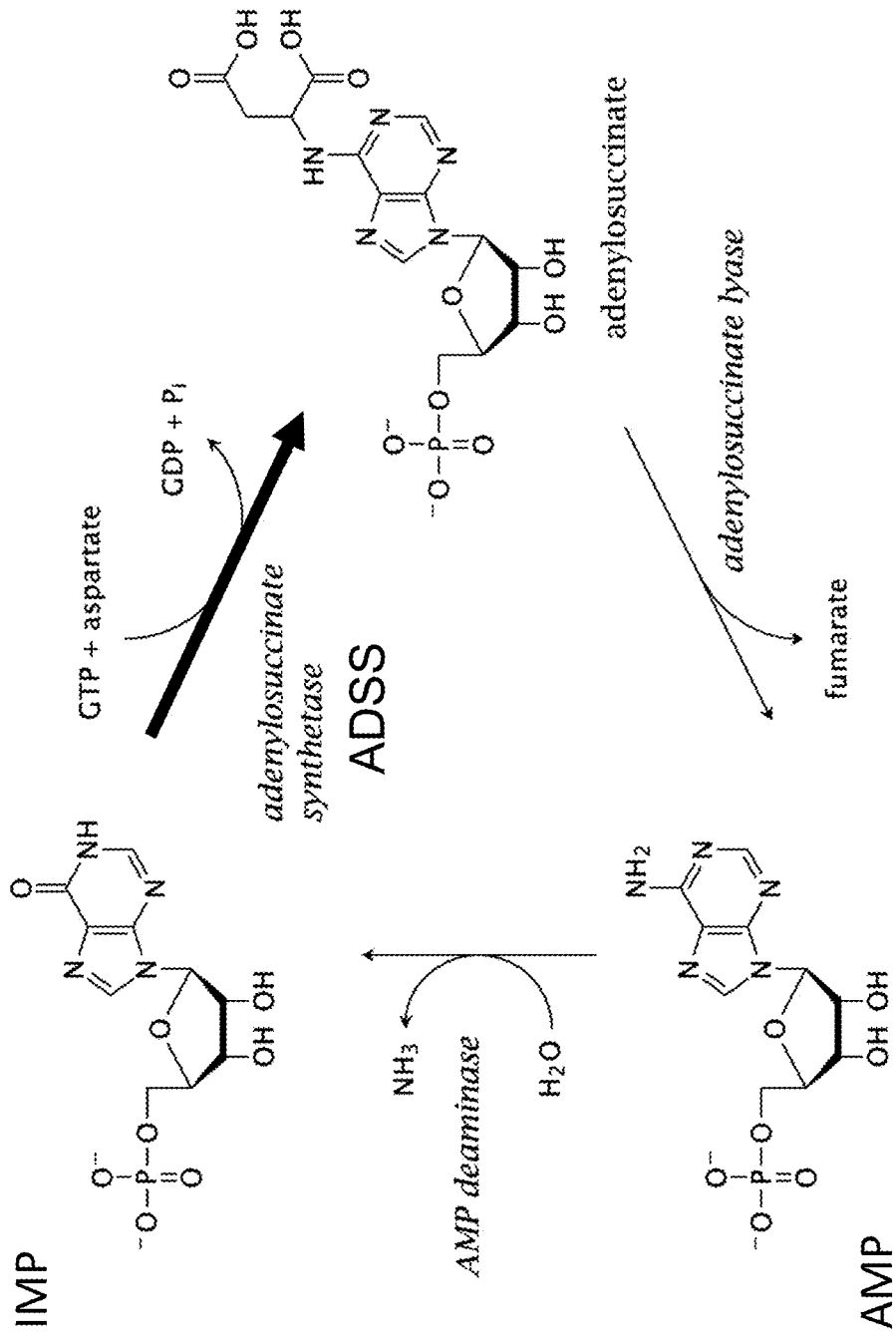
FIG. 4 describes the reaction mediated by ADSS.

Results on proteome and ubiquitination analysis in Kctd13Δ47 mice versus wildtype controls are shown in FIGS. 3A and 3B. For both ubiquitination analysis (FIG. 3A) and proteome analysis (FIG. 3B), adenylsuccinate synthase (ADSS) was identified as significantly regulated in Kctd13Δ47 mice versus wildtype controls. Thus, ADSS may be a ubiquitin ligase and proteasome substrate. FIG. 4 highlights the role of ADSS in catalyzing the first committed step in the de novo synthesis of adenosine monophosphate (AMP) from inosine monophosphate (IMP).

Figures 5A, 5B:
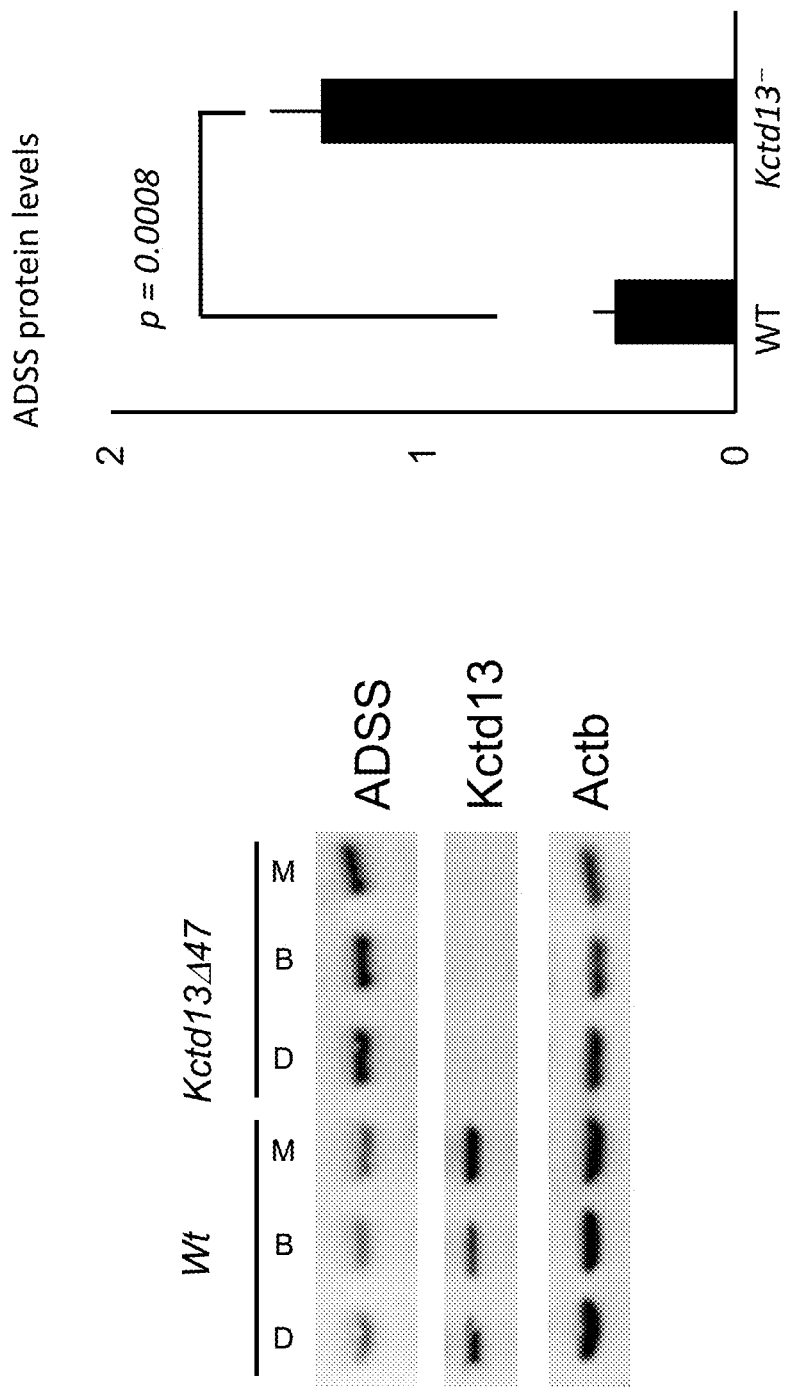
FIGS. 5A-5B shows immunoblot (A) and quantification (B) of ADSS protein levels in neurons from Kctd13Δ47 mice versus wildtype controls (D=DMSO; B=bortezomib; M=MLN4924). Kctd13-refers to Kctd13Δ47 mice.

Western blot results in FIGS. 5A (immunoblot) and 5B (quantification) show that ADSS protein levels are significantly increased by approximately 3.4-fold in neurons from Kctd13Δ47 mice versus wildtype controls. As a control, neurons were contacted with DMSO (D), bortezomib (B), or MLN4924 (M). Bortezomib is a proteasome blocker and MLN4924 is a general CULLIN inhibitor, which blocks the neddylation of the CULLIN subunit required for the ubiquitination of substrate. Bortezomib and MLN4924 are predicted to cause an increase in proteasome substrates. In neurons from Kctd13Δ47 mice, there is no change in ADSS levels after treatment with bortezomib (B) or MLN4924 (M) because in the absence of Kctd13, ADSS is not being ubiquitinated.

Example 3: Evaluation of ADSS Ubiquitination in HEK Cells

A method was developed to study ADSS ubiquitylation in HEK cells. The following plasmids were used for experiments: pCMV6 hADSS-myc-flag (Origene: RC204256), V82 hKCTD13_IRESPuro, V17 hCUL3-HA-Flag_IRESPuro, V20 hRBX1_IRESPuro, His-ubiquitin (W B Kailin, Dana-Farber Institute, Harvard Medical School).

A day before transfection (day −1) HEK 293T (HEK) cells were plated in 10 cm dishes at 3.8-4 million cells per dish. The next day (day 0), the plasmids containing His-Ub (Gift of Dr. W G Kaelin, Harvard Medical School), KCTD13, CUL3 and ADSS-myc-flag constructs were transfected into HEK cells. Two days following transfection, bortezomib was added to the transfected cells to a final concentration of 2 μM. Five hours later cells were harvested into PBS by scraping. 1 mL of the cell suspension was transferred to a tube for use as transfection controls and spun at 2500 rpm at 4° C. The remaining 9 mls were transferred to a 15 mL Falcon tube and spun at 1K for 5 minutes at 4° C. The supernatant was removed. The cell pellets were then frozen in liquid $N_2$. Samples were stored at −80° C. until ready to proceed with pulldown. Cell pellets were resuspended in 1 mL of chilled (4° C.) Buffer C (6M Gnd-HCl, 0.1M NaPO4, 10 mM Imidazole) then sonicated (Branson sonicator, microtip, power 30%, cycle 50, 10 to 15 pulses). Buffer C equilibrated Ni-NTA magnetic beads (Invitrogen) were added to the sonicated lysate. Beads were incubated 2 hours at 4° C. with rocking to collect His-Ub conjugated proteins. Beads were then washed twice with Buffer C supplemented with 2 mM PMSF, 1× Roche Protease inhibitors, twice with Buffer D (1:3 volume ratio Buffer C:Buffer E)/2 mM PMSF/Protease inhibitors (Roche), and once with Buffer E (25 mM Tris. CL, pH 6.8/20 mM imidazole/ protease inhibitor (Roche)/2 mM PMSF). Bound proteins were then eluted by boiling in 300 mM imidazole, 2× Laemli PAGE buffer, 500 mM β-mercaptoethanol. Eluted samples were loaded on a 4-12% Bolt Bis-Tris PAGE gel (Invitrogen) and run in MOPS buffer. A western transfer was performed and probed with the appropriate primary and secondary antibodies.

For transfection controls, cell pellets were resuspended in 100 μl of CST lysis buffer or RIPA buffer+PMSF+1× protease inhibitor tablet (Roche) and sonicated with a Diagenode water bath sonicator for 10 minutes. Samples were spun 10 min, 12K rpm and supernatant was transferred to a new tube. An equal volume of 4× gel loading dye+BME was added and the samples were boiled for 10 min. Samples were western blotted with the appropriate primary and secondary antibodies.

FIG. 6A presents the experimental protocol to study the effect of KCTD13 on ubiquitination of ADSS in the HEK model with exogenous expression of HisUb and RBX1/CUL3. Results in FIG. 6B show that ubiquitination of ADSS was seen when KCTD13, HisUb, and RBX/CUL3 were cotransfected with ADSS.

Figures 7A, 7B:
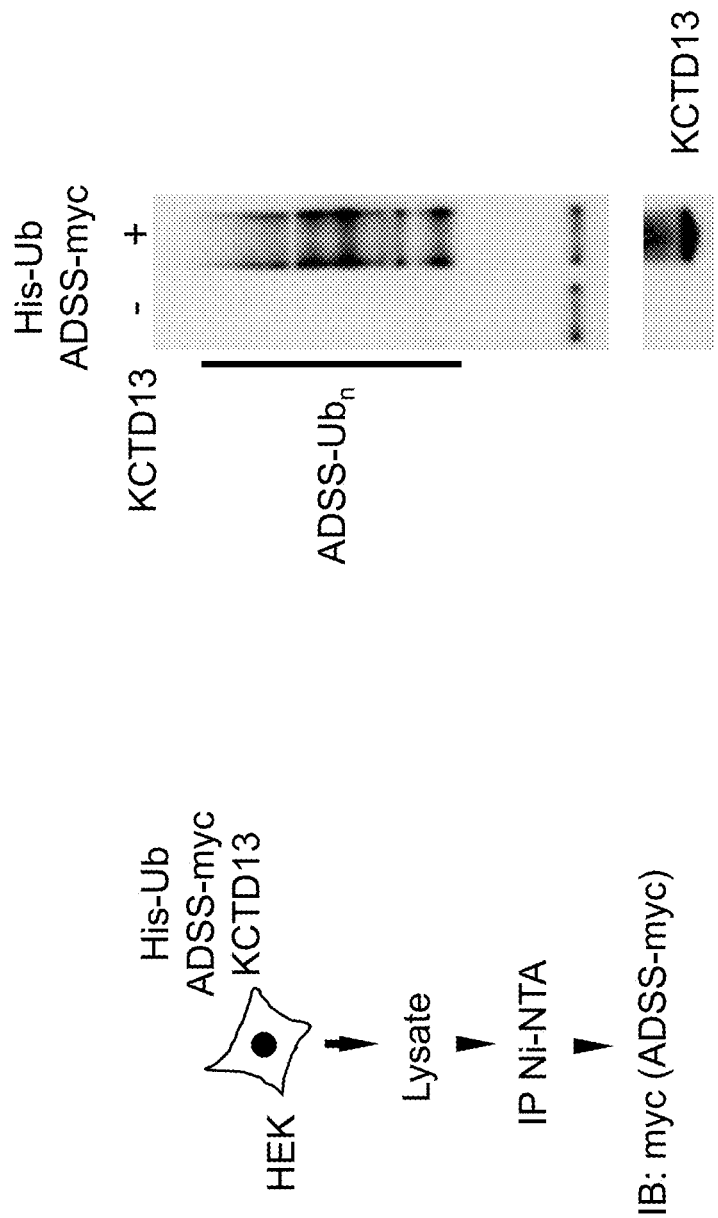
FIGS. 7A-7B show experimental protocol (A) and results (B) on the effect of KCTD13 and HisUb cotransfection with ADSS in a HEK model without exogenous RBX/CUL3.

FIG. 7A presents the experimental protocol to study the effect of KCTD13 on ubiquitination of ADSS in the HEK model with exogenous expression of His-Ub. Results in FIG. 7B show that ubiquitination of ADSS was seen when KCTD13 and HisUb were cotransfected with ADSS without exogenous RBX/CUL3. Ubiquitination of ADSS was not seen in the absence of coexpression of KCTD13.

Figures 8A, 8B:
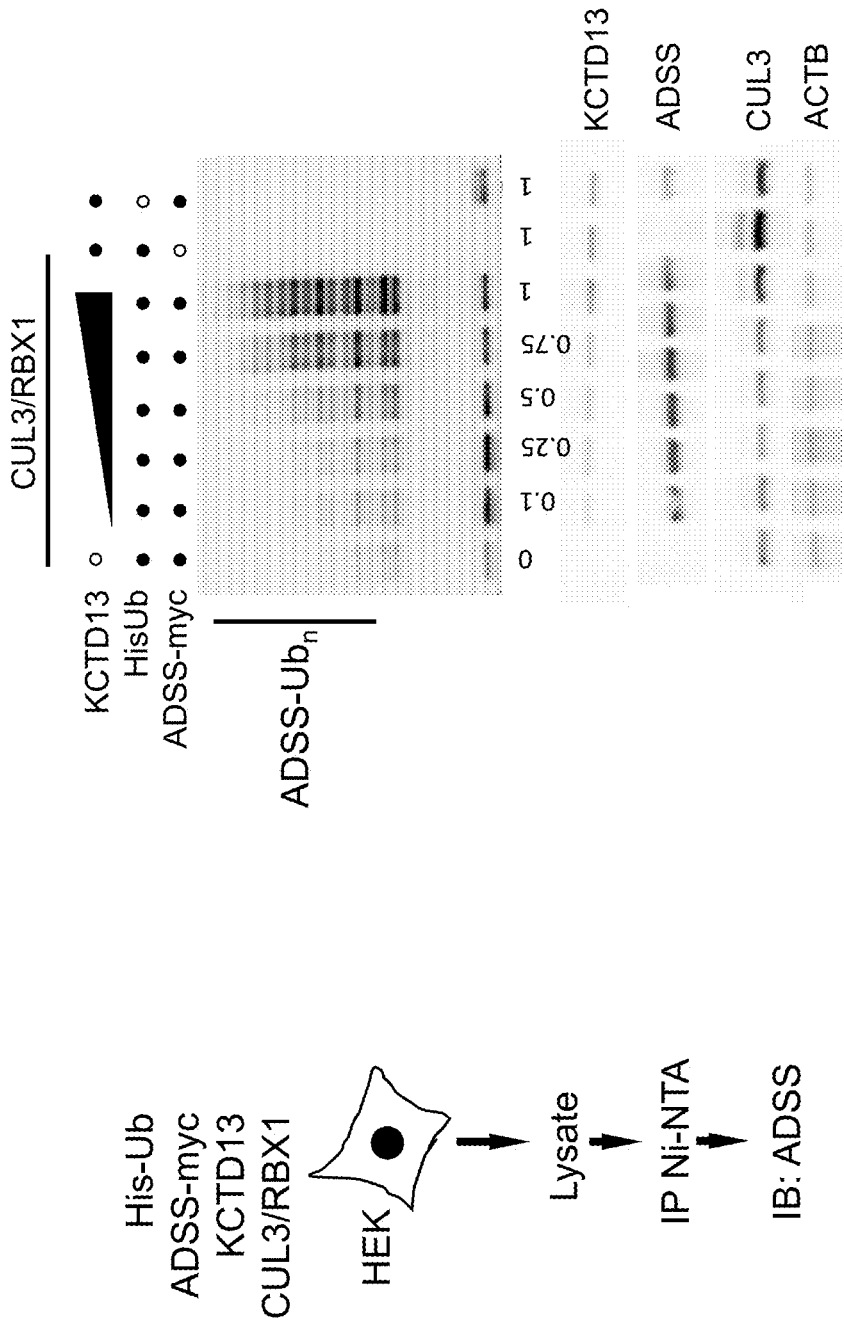
FIGS. 8A-8B show experimental protocol (A) and results (B) on the concentration-dependent effect of KCTD13 transfection on ubiquitination of ADSS in HEK cells.

FIGS. 8A and 8B show the concentration-dependent effect of KCTD13 transfection on ubiquitination of ADSS. Ubiquitination of ADSS increased as the concentration of KCTD13 transfected was increased from 0 to 1 μg in the transfection.

Figure 9A:
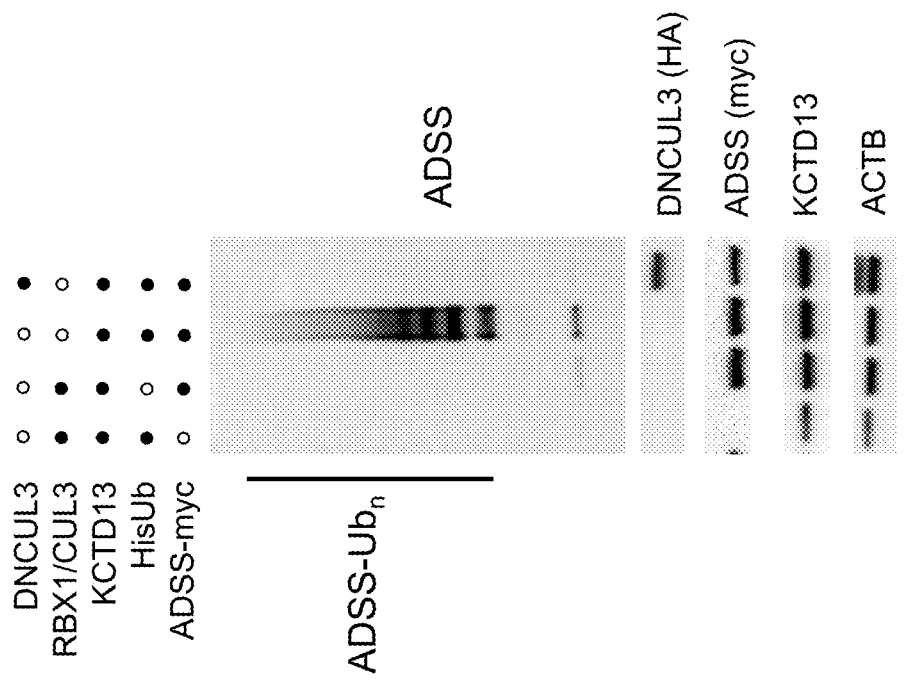
FIGS. 9A-9C show experimental design (A), signaling effect (B), and experimental results (C) of a dominant-negative CUL3 (DNCUL3) on ADSS ubiquitination by KCTD13 in HEK cells.
Figure 9B:
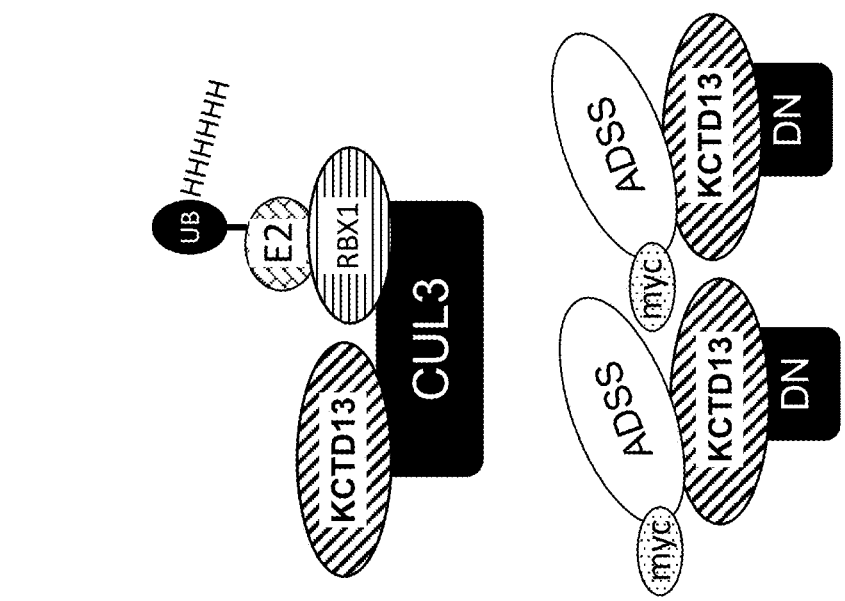
Figure 9C:
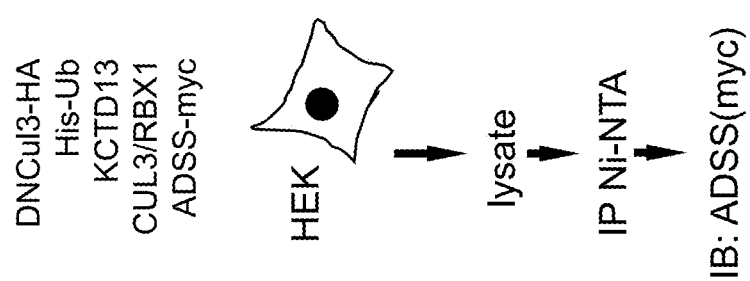

FIG. 9A shows the experimental design to study the effect of a dominant-negative CUL3 (DNCUL3) on ADSS ubiquitination by KCTD13 in HEK cells. This DNCUL3 construct would be expected to block any ubiquitin-mediated effects of a cul3-dependent ubiquitin ligase, as shown in FIG. 9B. As shown in FIG. 9C, expression of the DNCUL3 construct blocked the effect of KCTD13 to increase ubiquitination of ADSS.

Example 4: Co-Immunoprecipitation Experiments in HEK 293 Cells

Experiments were performed in HEK 293 cells to study interactions between KCTD13 and ADSS in a heterologous system.

The co-immunoprecipitation protocol was as follows. For transfections, 3.8 million cells were plated in a 10 cM tissue culture dish 24 hours in advance of transfection. Cells were transfected according to manufacturer's instructions using Lipofectamine 2000 in 6 well plates. Cells were collected 72 hours post-transfection. Media was aspirated, washed 1× with chilled PBS, collected in 10 mL chilled PBS, centrifuged (1000 RPM, 5 min, 4° C.). Supernatant was aspirated and pellets were snap frozen in LN2. Pellets were stored at −80° C. until processed. Cell pellets were lysed with 1 mL Ubiquitin lysis buffer (1×CST lysis buffer (Cell Signaling Technology), PIC2 (Sigma), PIC3 (Sigma), 0.1 mM chloracetimide (Sigma), 10 mM NaF (Sigma), 2 mM PMSF (Aldrich), Roche protease inhibitor mini (Roche), 50 uM PR-619 (Lifesensors), 2 mM 1,10 orthophenanthroline (Sigma). Prior to collecting antibody protein complexes, protein A magnetic Dynabeads (Thermo-Fisher/Invitrogen) were blocked in 5% BSA for 1 hr with rocking at 4° C. Dynabeads were then loaded with 0.5 μg CHIP grade IgG (Abcam) with rocking at 4° C. for 1 hr and then 50 μL of beads were added to the protein lysates to preclear of any nonspecific IgG-Dynabead binding proteins. Whole cell lysates were prepared from frozen pellets by sonicating pellets resuspended in 1 mL ubiquitin lysis buffer in a Diagenode water bath sonicator on HIGH for 5 minutes at 4° C. Lysates were spun at 14K RPM for 10 min at 4° C. Supernatant were transferred to a new tube and 50 µL of a 50% slurry of pre-loaded, pre-blocked beads were added to the lysate for 1 hour at 4° C. with rocking. Beads were collected using a magnet and supernatant was transferred to a clean tube. Lysate was divided among 8 aliquots (125 µL) and primary antibody against myc epitope (CST, clone) (rb) or KCTD13 or rabbit IgG was added at a 1:50 (i.e., 2.5 µL) dilution. Lysates were rocked at 4° C. for 1 hour. While antibody-lysate mixtures were rocking, a fresh 50% slurry of protein A magnetic Dynabeads was prepared in ubiquitin lysis buffer (50% bead slurry). Beads were washed and resuspended as described previously. At the end of 1 hour 50 µL of bead slurry was added to each protein antibody mixture to collect antibody protein immunocomplexes. Following collection of immunocomplexes, beads were washed 5 times with 0.5 mL RIPA wash Buffer (10 mM Tris-Cl, pH 8.0, 1 mM EDTA, 1% Triton X-100, 0.1% sodium deoxycholate, 0.1% SDS, 140 mM NaCl) supplemented with 2 mM PMSF and 1× Roche protease inhibitor cocktail (Roche). After each addition of RIPA wash buffer, beads were collected using a magnet. After the final wash step buffer was completely aspirated to ensure all wash buffer was completely removed. Proteins were eluted from the beads by resuspending in 75 uL of 2× Laemli buffer (Bio-Rad) containing 500 mM mM β-mercaptoethanol. Samples were then heated at 95° C. for 6 minutes to denature proteins and either western blots were run as described below or samples were stored at −80° C. To measure the input levels of transfected proteins in whole cell lysates, 50 µL of starting lysate was mixed with 48 µL 4× Laemli buffer plus 2 µL BME and heated at 95° C. for 6 minutes. When necessary, lysates were further diluted with 2× Laemli buffer. Western transfers and immunoblotting were carried out using the Thermo-Fisher/Invitrogen Bolt system Briefly, 5 µL of each eluted IP sample was loaded on an 8% Bolt Bis-Tris-Plus Gel (15-well) and run in Bolt 1×MOPS Running buffer (BOLT). Gels were run at 165V for 32 minutes and transferred using an iBLOT2 to nitrocellulose for 7 minutes. Following western transfer, membranes were blocked in 5% BSA in 1× Tris Buffered Saline plus Tween (TBS-T, Sigma) for 1 hour at RT on a rocking platform. Following blocking, primary antibody (Myc or Kctd13) was added at 1:1000 and incubated on a rocking platform at 4° C. overnight. Subsequently, membranes were washed with 3 brief washes to remove the antibody mixture, followed by three washes with 1×TBS-T for 5 min each. Secondary antibody consisting of Donkey and rabbit conjugated to horseradish peroxidase (HRP, GE Healthcare, NA934V) diluted 1:5000 in 5% blotting milk (Bio-Rad) in TBS-T was then added to membranes and incubated at RT for 1 hour on a rocking platform. Membranes were washed with 3 brief washes to remove the antibody mixture, followed by three washes with 1×TBS-T for 5 min each. Just prior to imaging, the membranes were rinsed once with Tris-Buffered Saline without Tween. Membranes were imaged by incubating each membrane in Femto ECL (Pierce) for 1 min and then imaging on a Bio-Rad Chemidoc. For loading controls for input levels of proteins, membranes were incubated with an antibody to B-actin coupled to HRP (Cell Signaling Technology) diluted in 5% BSA in TBS-T for total inputs for 1 hour followed by washing as described for other primary and secondary antibodies.

FIG. 10A shows the experimental conditions for the immunoprecipitation experiment. FIG. 10B shows that immunoprecipitation (IP) with antibody against KCTD13 (K lanes) led to immunoprecipitation of ADSS, as signal was seen with immunoblotting (IB) for the myc antibody, and CUL3, as signal was seen with IB for the HA antibody. The input lanes (i) show lysate sample that was not subjected to immunoprecipitation.

Figures 11A, 11B:
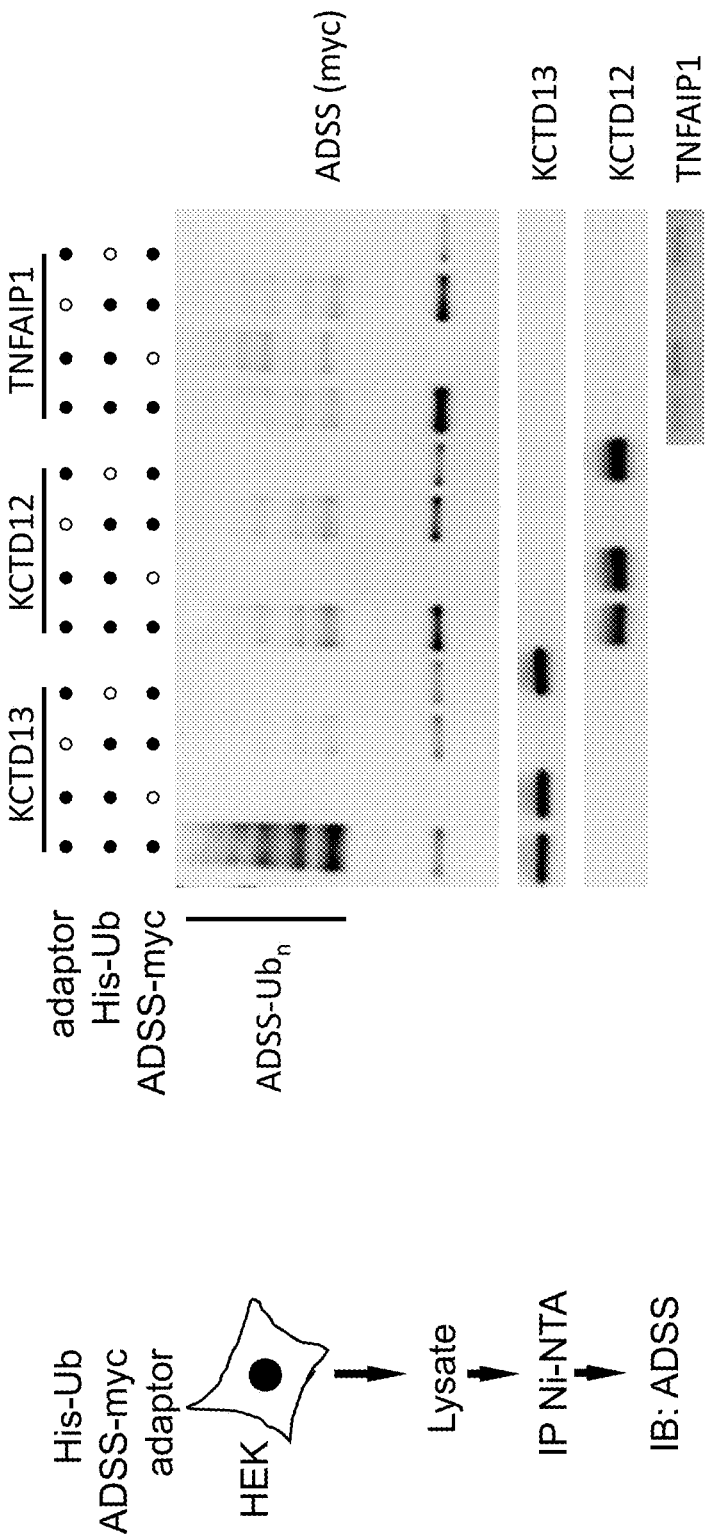
FIGS. 11A-11B show experimental design (A) and results (B) on ubiquitination of ADSS following expression of the different adaptor proteins KCTD13, KCTD12, and TNFAIP1. The top panel in FIG. 11B shows ubiquitination results, while the lower blots show western blots confirming expression of the different adaptor proteins.

KCTD13 is an adapter protein that binds to CUL3. It was next investigated whether other adaptor protein, such as KCTD12 or TNFAIP1, could also promote ubiquitination of ADSS. FIG. 11A shows the experimental outline for the experiment, with the transfection of the adaptor proteins KCTD13, KCTD12, or TNFAIP1 in parallel experiments. FIG. 11B shows that only KCTD13, and not KCTD12 or TNFAIP1, expression increased the ubiquitination of ADSS. These experiments confirm that not all adaptor proteins are equivalent and that KCTD13 has a unique role in regulating ubiquitination of ADSS.

Example 5. Metabolomic Profiling of Fibroblasts and Neurons

16p11.2 deletion patient fibroblast samples were acquired from the Simons Foundation VIP collection. For comparison, fibroblasts from unaffected individuals were obtained from Mclean Hospital collection of primary fibroblasts (Cohen, Ongur, McPhee). Fibroblasts were grown in DMEM supplemented with 10% serum (Gibco). For metabolic experiments, 160,000 cells/well were plated in DMEM (Gibco) supplemented with 10% fetal bovine serum (Gibco) in 12 well plates. For neurons, 1 million primary mouse neurons/well were plated in 6 well plates and were extracted similar to fibroblasts as described below except volumes were doubled to accommodate the extra surface area.

Figure 12:
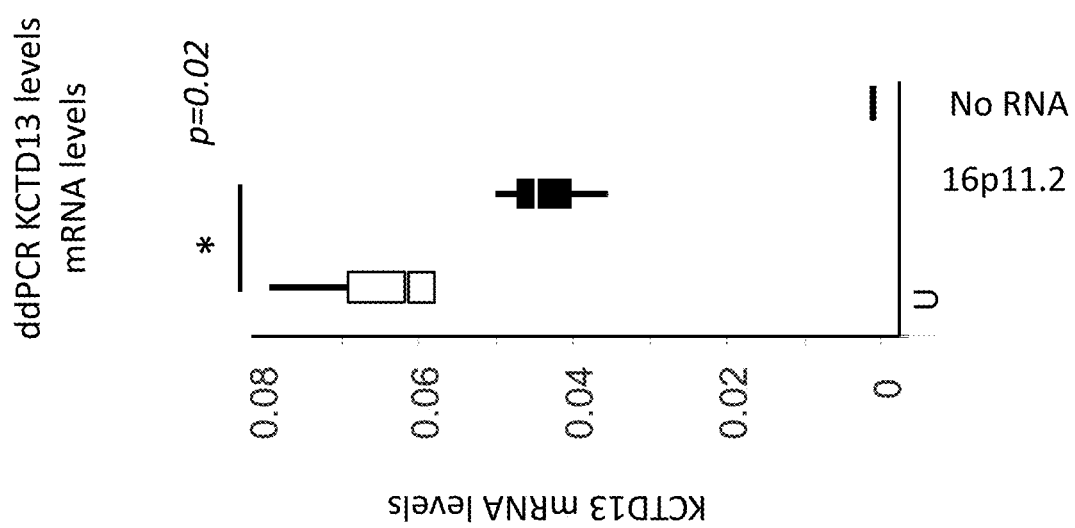
FIG. 12 shows KCTD13 mRNA levels in 16p11.2 deletion patient fibroblasts and unaffected (U) control fibroblasts.

It was first determined whether KCTD13 mRNA levels were altered in 16p11.2 deletion patient fibroblasts compared with control unaffected (U) fibroblasts. FIG. 12 shows that KCTD13 mRNA levels were significantly lower in 16p11.2 deletion patient fibroblasts, confirming an alteration in expression of KCTD13 mRNA with this deletion.

Next, metabolic changes were determined between 16p11.2 deletion patient fibroblasts compared with control fibroblasts. For metabolite extraction, samples were collected from either cells or the cell media. Cell samples were extracted from cells grown in 12 well plates. Cell samples were extracted by washing cells once with 1 mL ice-cold PBS, transferring to dry ice, followed by adding 400 µL of 80% methanol (VWR) containing the internal standards inosine-$^{15}$N4, thymine-d4, and glycocholate-d4 (Cambridge Isotope Laboratories). Cells were then incubated for 15 minutes at −80° C., followed by scraping and transfer of the methanol and cells to a 1.5 mL tube. Cells were centrifuged (10 min, 9,000 g, 4° C.), and the supernatant was transferred to a new 1.5 mL tube. The pellet was extracted again with 50 µL of 80% methanol containing internal standards and centrifuged. The supernatant was then pooled with the previously collected methanol sample. Media supernatant samples (30 µL) were extracted using 120 µL of 80% methanol (VWR) containing the internal standards inosine-$^{15}$N4, thymine-d4, and glycocholate-d4 (Cambridge Isotope Laboratories). The samples were centrifuged (10 min, 9,000 g, 4° C.). The resulting supernatant was transferred to a new tube. Samples were stored at −80° C. until analysis.

A method using basic hydrophilic interaction chromatography (HILIC) separation and negative ionization mode MS detection was established on an LC-MS system consisting of an ACQUITY UPLC (Waters Inc.) coupled to a 5500 QTRAP triple quadrupole mass spectrometer (AB SCIEX). Supernatants were injected directly onto a Luna NH2 column (150×2.0 mm, 5 μm particle size; Phenomenex) that was eluted at a flow rate of 400 μL/min with initial conditions of 10% mobile phase A (20 mM ammonium acetate and 20 mM ammonium hydroxide (Sigma-Aldrich) in water (VWR)) and 90% mobile phase B (10 mM ammonium hydroxide in 75:25 v/v acetonitrile/methanol (VWR)) followed by a 10-min linear gradient to 100% mobile phase A. The ion spray voltage was −4.5 kV and the source temperature was 500° C.

Raw data were processed using MultiQuant 1.2 software (AB SCIEX) for automated LC-MS peak integration. All chromatographic peaks were manually reviewed for quality of integration and compared against a known standard for each metabolite to confirm compound identities. Internal standard peak areas were monitored for quality control, to assess system performance over time, and to identify any outlier samples requiring re-analysis. A pooled plasma reference sample was also analyzed after sets of 20 study samples as an additional quality control measure of analytical performance and to serve as reference for scaling raw LC-MS peak areas across sample batches. Metabolites with a signal-to-noise ratio <10 were considered unquantifiable.

Figure 13:
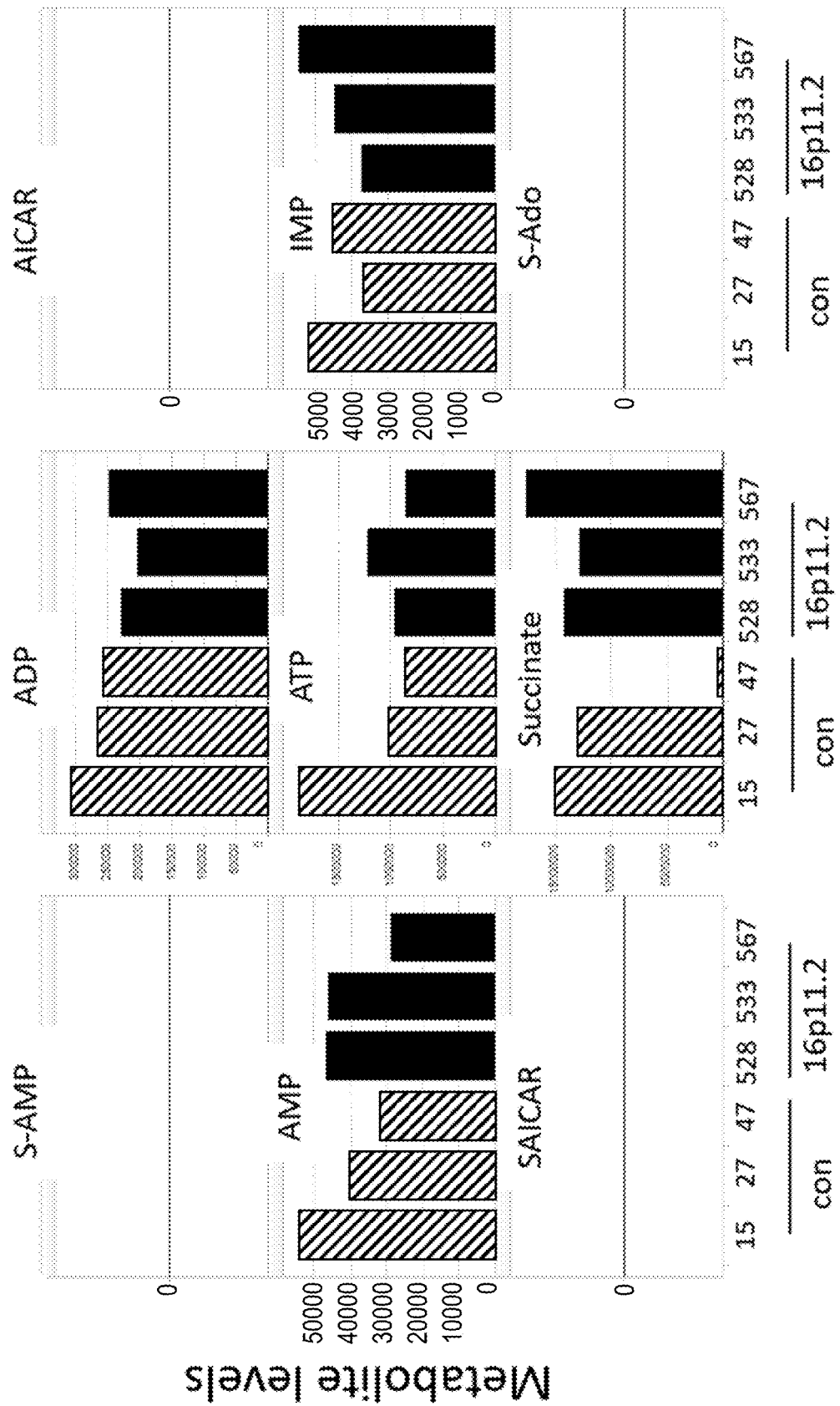
FIG. 13 shows metabolic results from LC/MS analysis of cell lysate samples from 16p11.2 deletion patient fibroblasts and control (con) fibroblasts.
Figure 14:
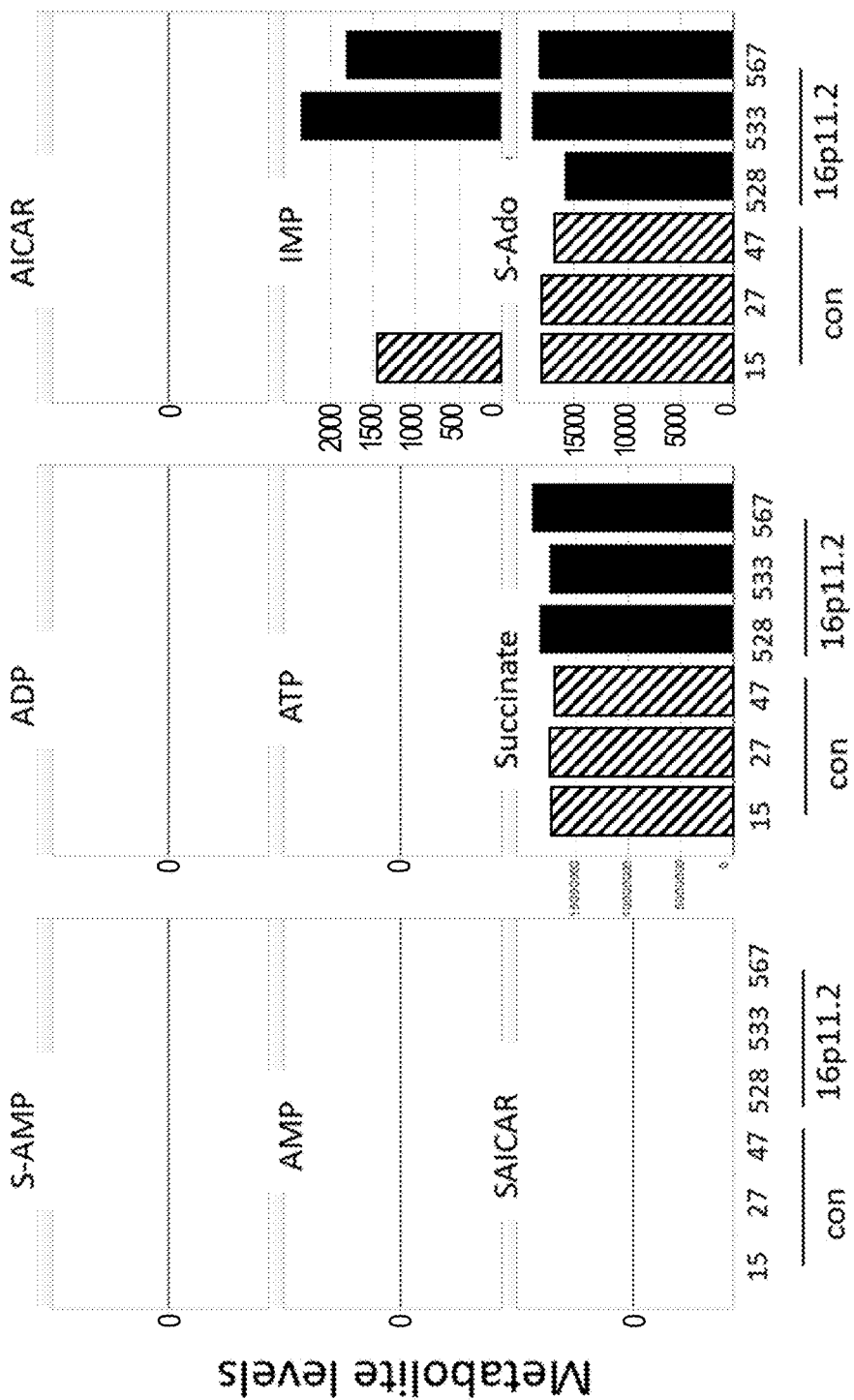
FIG. 14 shows metabolic results from LC/MS analysis of media samples from 16p11.2 deletion patient fibroblasts and control (con) fibroblasts.

Purine metabolites were not altered in fibroblast cell lysates (FIG. 13) or media (FIG. 14) from 16p11.2 deletion patients compared to control patients.

Figure 15:
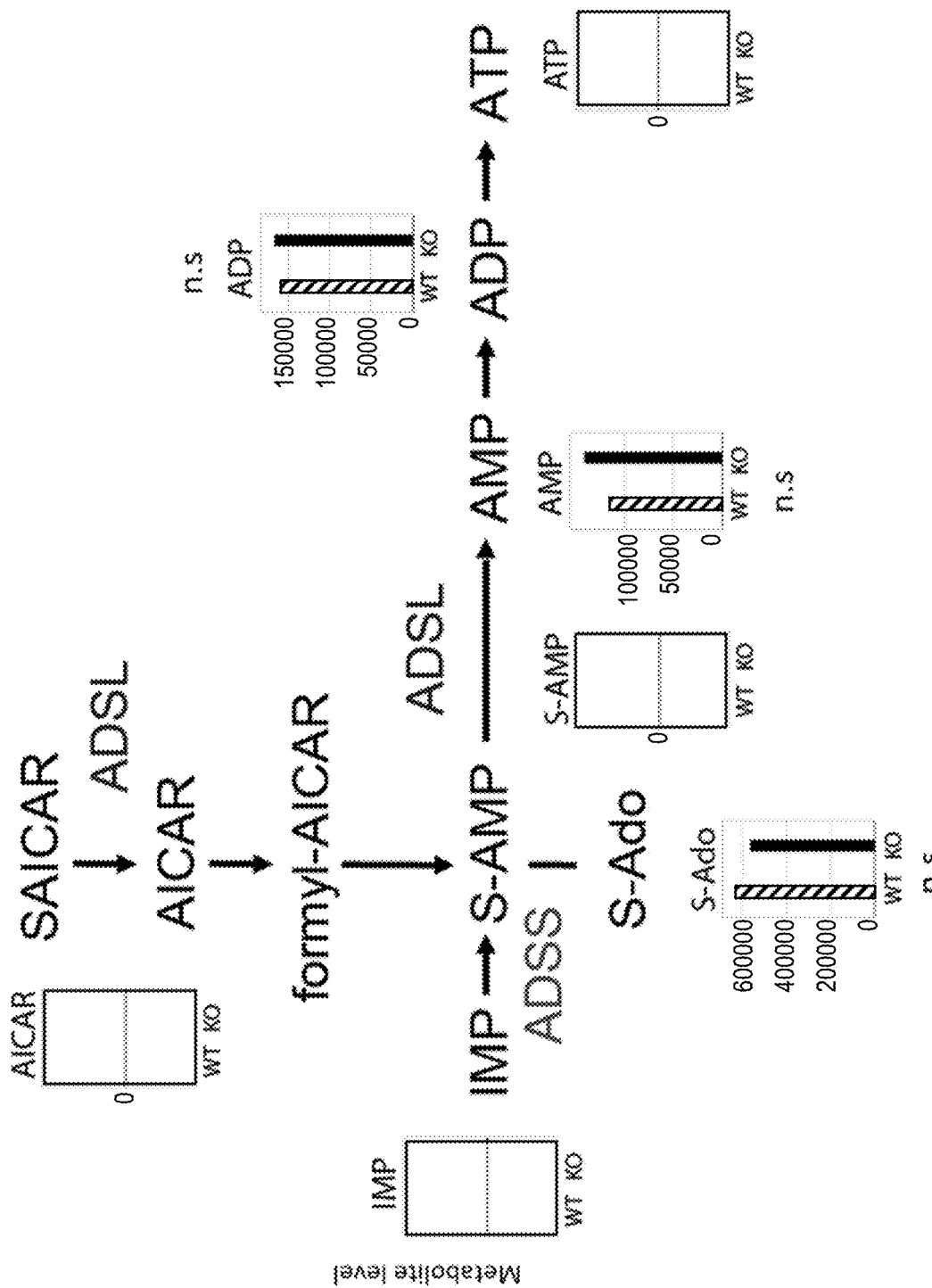
FIG. 15 shows purine metabolite levels in urine from WT or KO (Kctd13Δ47) mice.

Purine metabolites were also compared in urine from adult WT and kctd13Δ47 mice. The kctd13Δ47 mice did not have alterations in purine metabolites in urine compared to WT mice (FIG. 15). Blank graphs in FIG. 15 were not detectable.

Next, purine metabolites were assessed in cell lysates and supernatants of cultured neurons from wild-type and kctd13Δ47 mice. Neurons were cultured until division 21, at which point lysates and supernatants were prepared using the same protocol as for the fibroblast samples.

Figure 16:
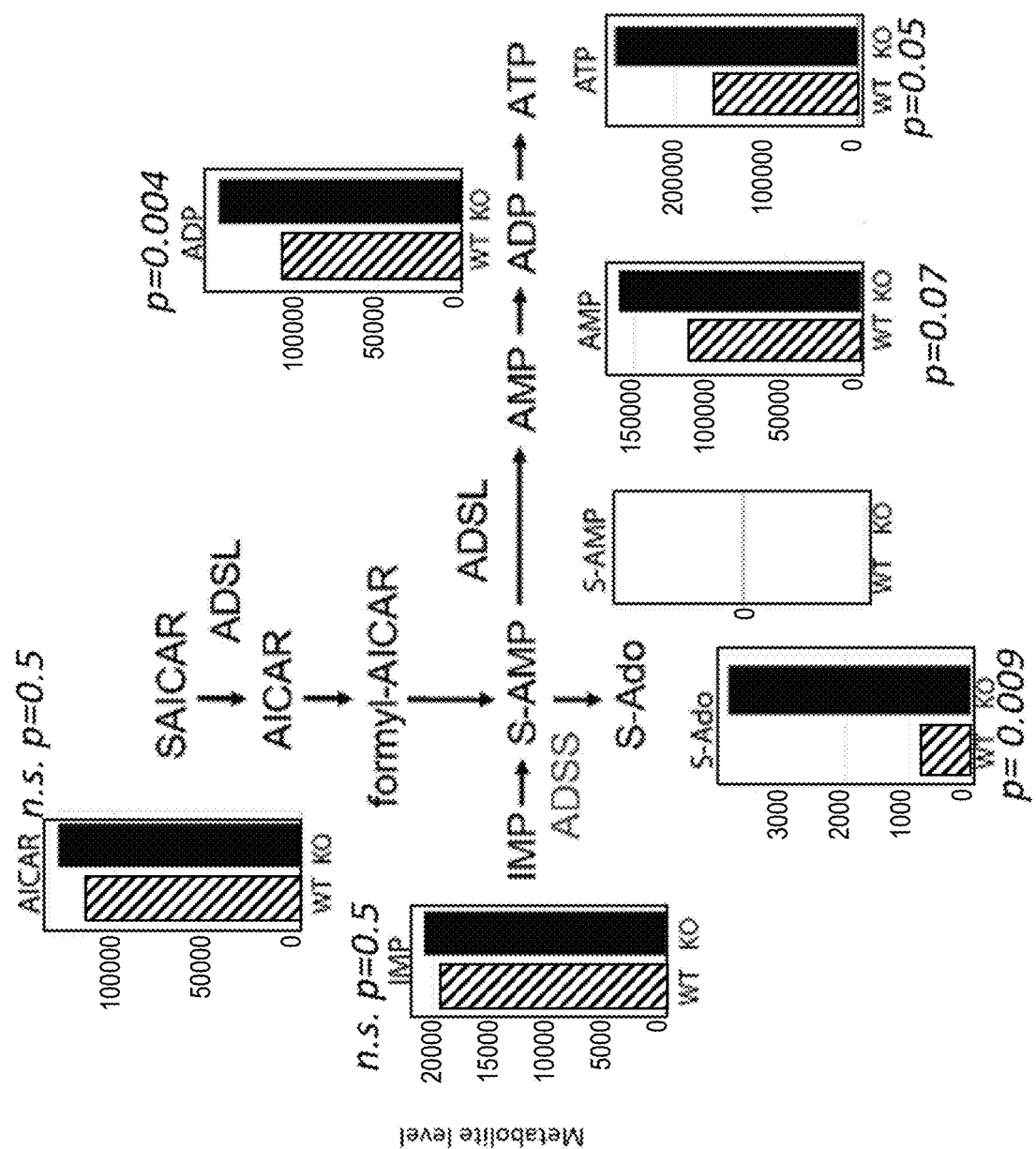
FIG. 16 shows purine metabolite levels in cell lysates of neurons at 21 days in vitro (DIV21) from WT or KO (Kctd13Δ47) mice.
Figure 17:
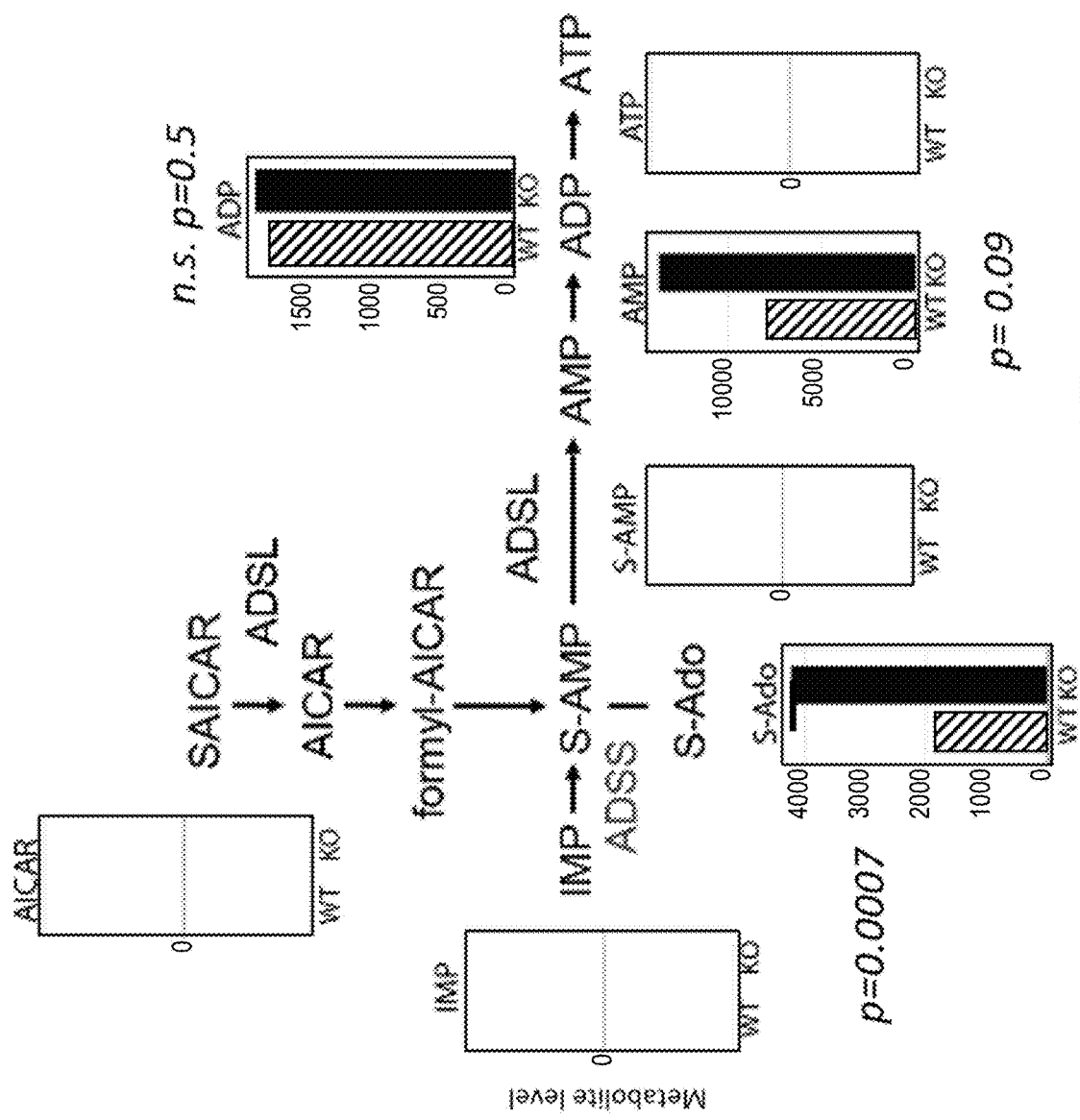
FIG. 17 shows purine metabolite levels in media supernatants of division 21 (DIV21) neurons from WT or KO (Kctd13Δ47) mice.
Figure 18A:
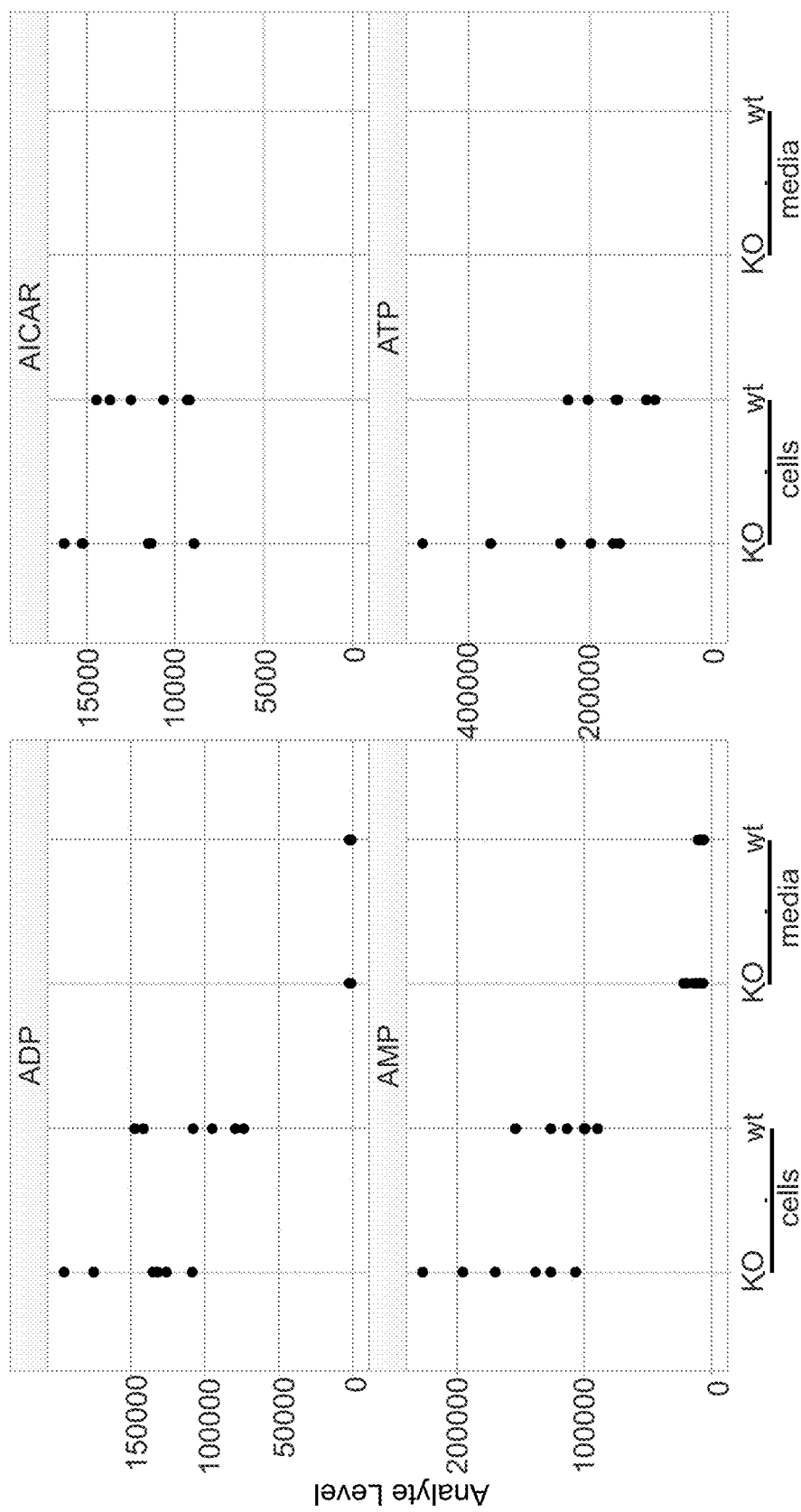
FIG. 18A-D shows a summary of changes in purine metabolites in cell lysates and media supernatants of DIV21 neurons from WT or KO (Kctd13Δ47) mice.
Figure 18B:
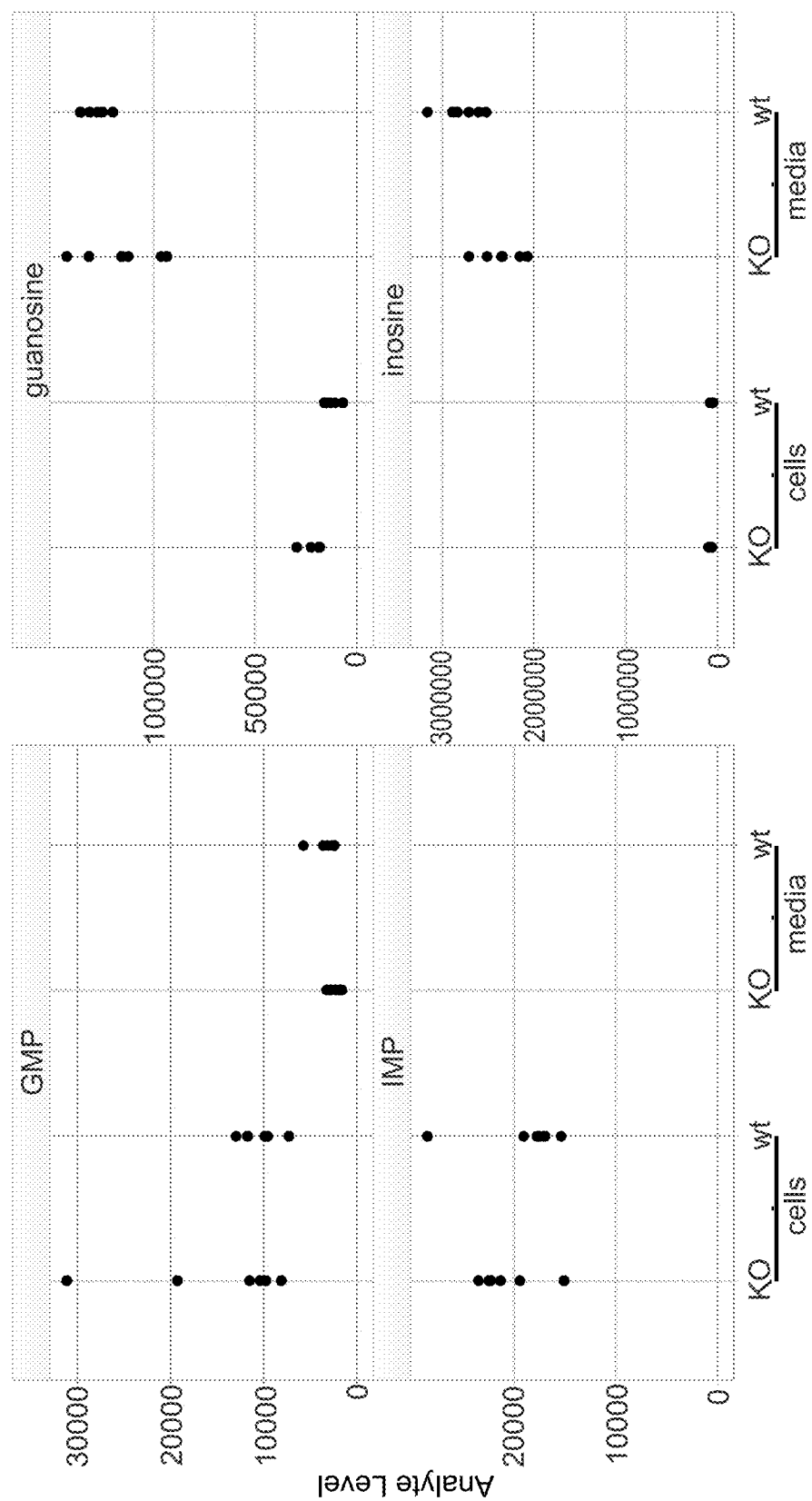
Figure 18C:
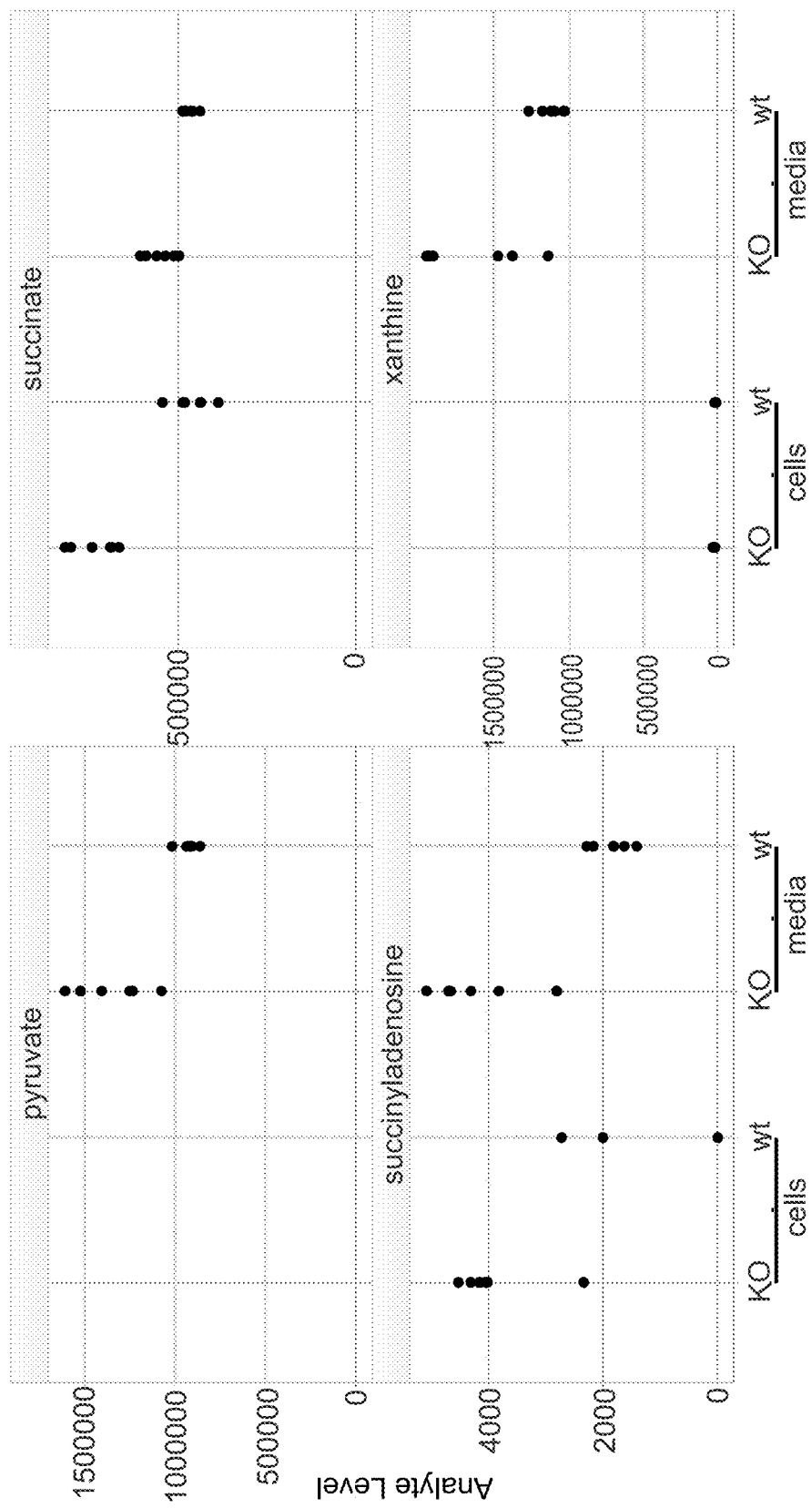
Figure 18D:
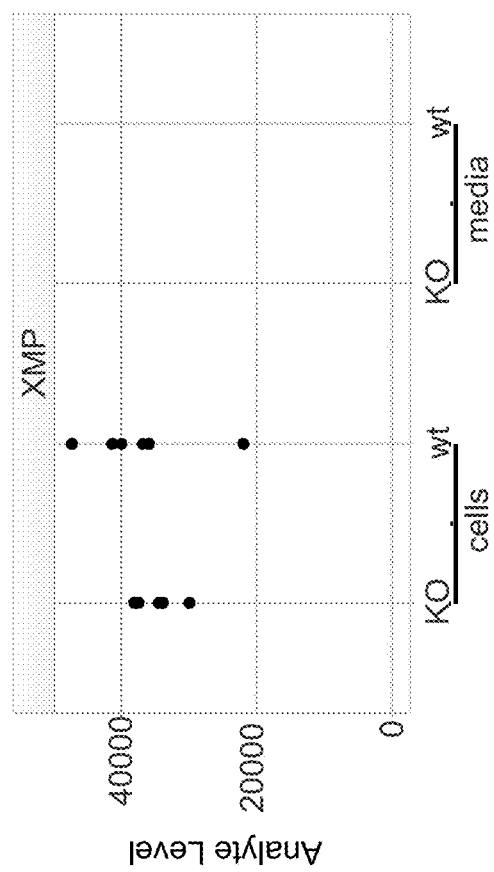
Figure 21:
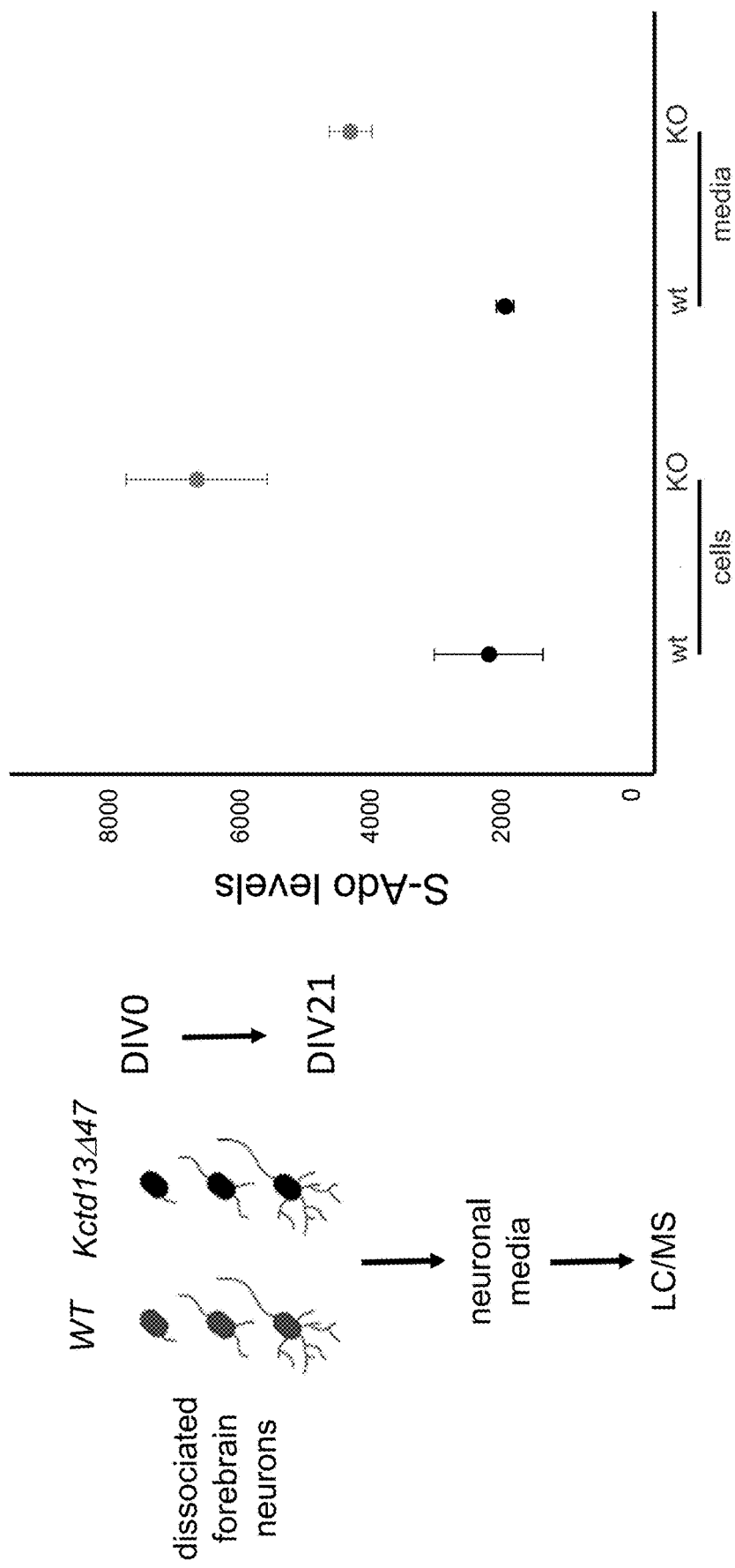
FIG. 21 shows S-Ado levels in cultured neurons from wild-type and Kctd13Δ47 (KO) mice, and in neuronal media.

Purine metabolites downstream of ADSS (including s-Ado, AMP, ADP, and ATP) were present at higher levels in cell lysates of cultured neurons from kctd13Δ47 mice compared to WT (FIG. 16). See also FIG. 21. Similarly, levels of S-Ado and AMP were increased in neuronal media from kctd13Δ47 mice compared to WT (FIG. 17). See also FIG. 21. FIG. 18A-D shows the levels of various purine metabolites in cell lysates and media of WT and kctd13Δ47 (KO) mice. Levels of adenylsuccinate, guanine, and SAICAR were not detectable.

Without intending to be bound by any particular theory, these data suggest that an increase in ADSS activity in kctd13Δ47 mice leads to changes in purine metabolism in neurons, with higher levels of metabolites downstream of ADSS. Since changes in purine metabolites were seen in neurons from kctd13Δ47 mice but not in fibroblasts from 16p11.2 deletion patients, these results may indicate that neurons are particularly impacted by changes in ADSS function.

AMP is known to be able to signal through AMP-kinase to regulate numerous intracellular processes, including energy homeostasis. Thus, ADSS may function to influence energy homeostasis by increasing AMP (see Stenesen D, et al., *Cell Metab* 17(1):101-12 (2013) and Jacquemont S et al., *Nature* 478(7367):97-102 (2011)), which is a positive regulator of AMP-kinase. Thus, inhibition of AMP kinase activity may be another means to mitigate dysfunction of purine metabolism in 16p11.2 deletion patients.

Example 6: Alterations in Purine Metabolism with ADSS Inhibition

L-alanosine has been characterized as an active anabolite and inhibitor of ADSS (see Tyagi A K, et al., *Cancer Res* 40(12):4390-7 (1980)). Thus, L-alanosine may be used as an ADSS inhibitor in metabolic profiling experiments.

Figure 19:
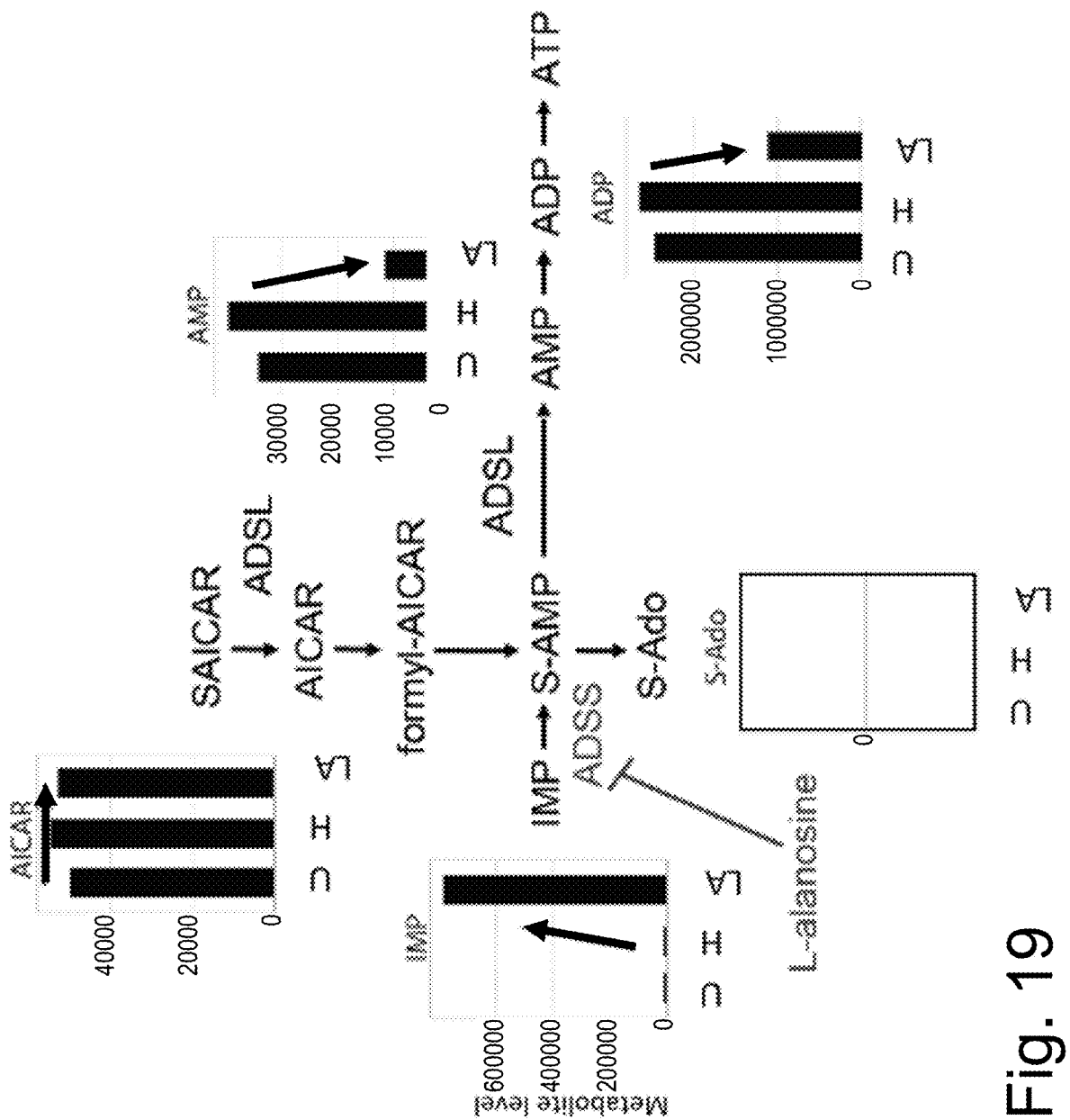
FIG. 19 shows purine metabolite levels in human fibroblast cell lysates following treatment with Hepes (H), L-alanosine (LA, an inhibitor of ADSS), or untreated (U).

Human control fibroblasts in culture were treated for 12 hours with HEPES, 10 mg/mL L-alanosine (LA), or were left untreated. As shown in FIG. 19, treatment with LA increased levels of IMP and decreased levels of AMP and ADP, showing the ability of LA to functionally decrease ADSS activity and alter purine metabolism. Levels of aminoimidazole carboxamide ribotide (AICAR), a metabolite upstream of ADSS, were not affected by LA treatment.

Figure 20A:
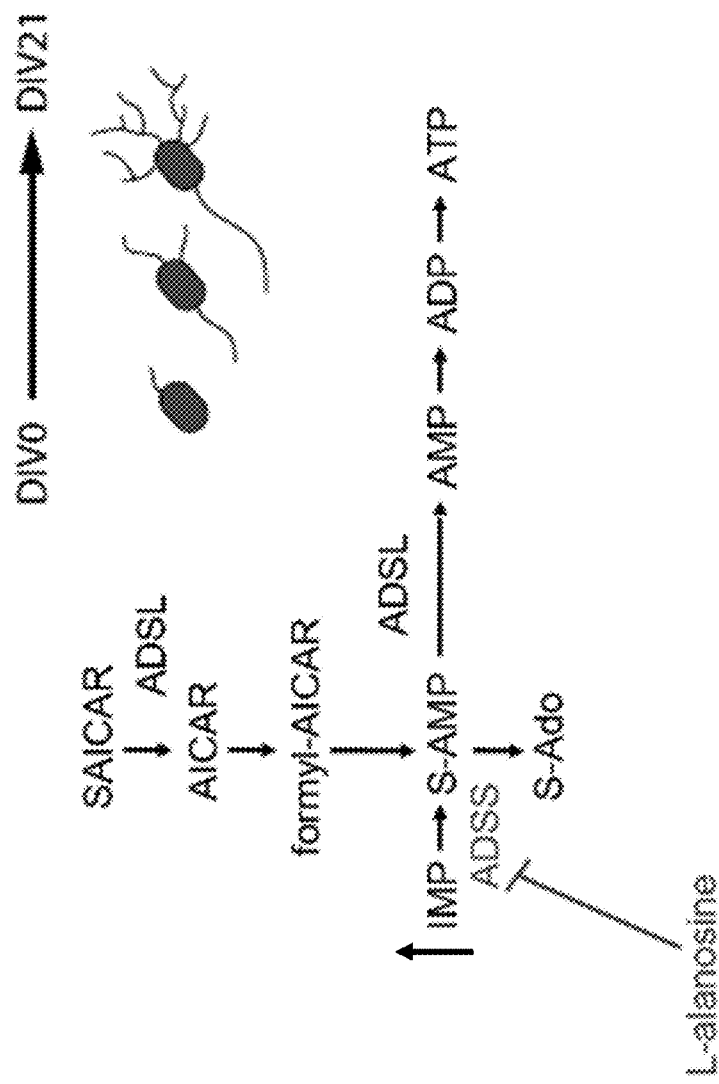
FIGS. 20A-B show IMP levels in cell lysates of DIV21 neurons from WT mice following treatment with D, L-alanosine or L-alanosine, or untreated (U).
Figure 20B:
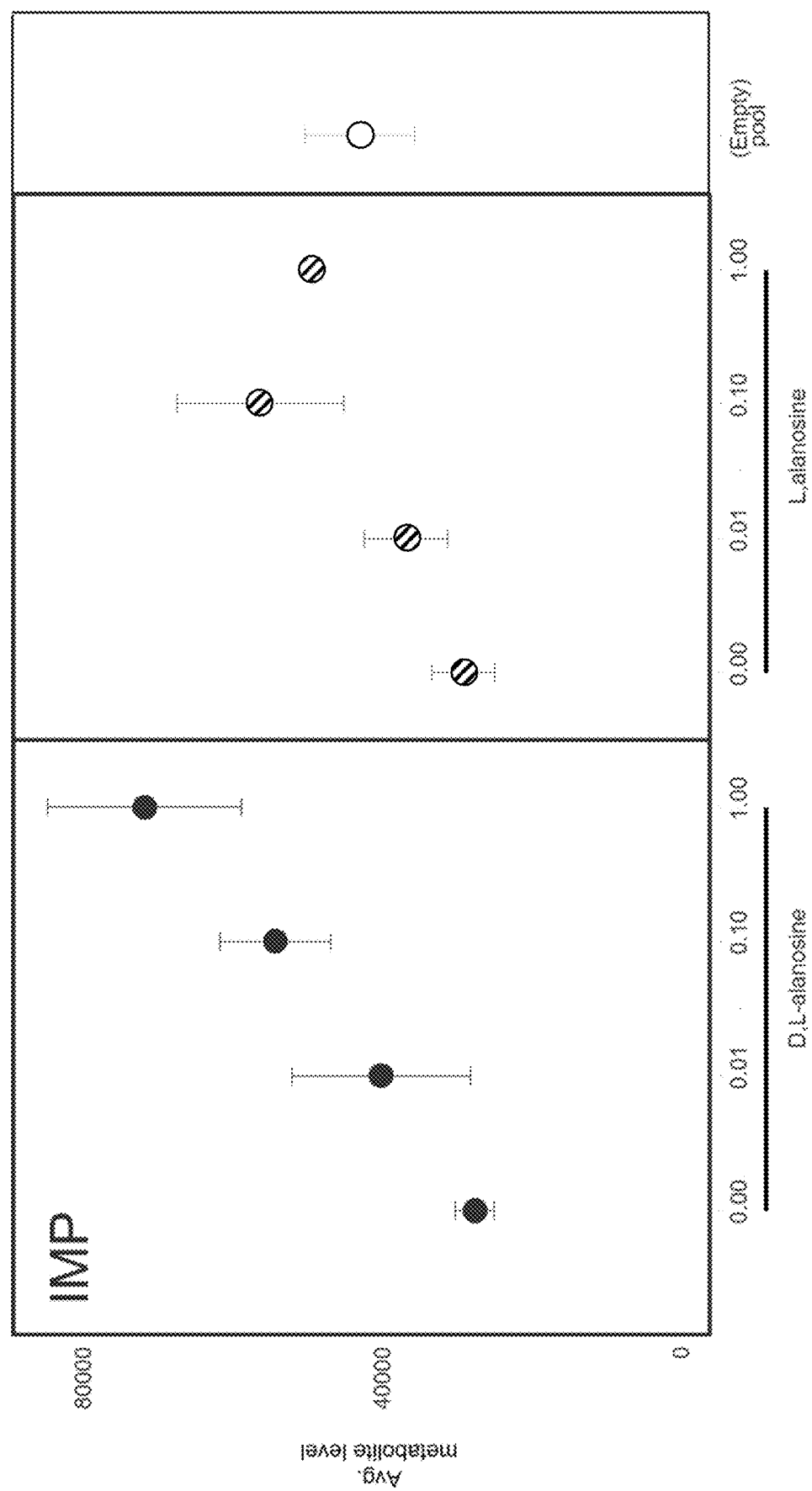

A dose-response was performed with D,L-alanosine and L-alanosine in DIV21 mouse neurons. As shown in FIG. 20, both the D,L and the L forms of alanosine produced a dose-dependent increase in IMP levels. Thus, the D,L and L forms of alanosine can functionally inhibit ADSS and may be useful for regulating purine metabolism.

Figure 22:
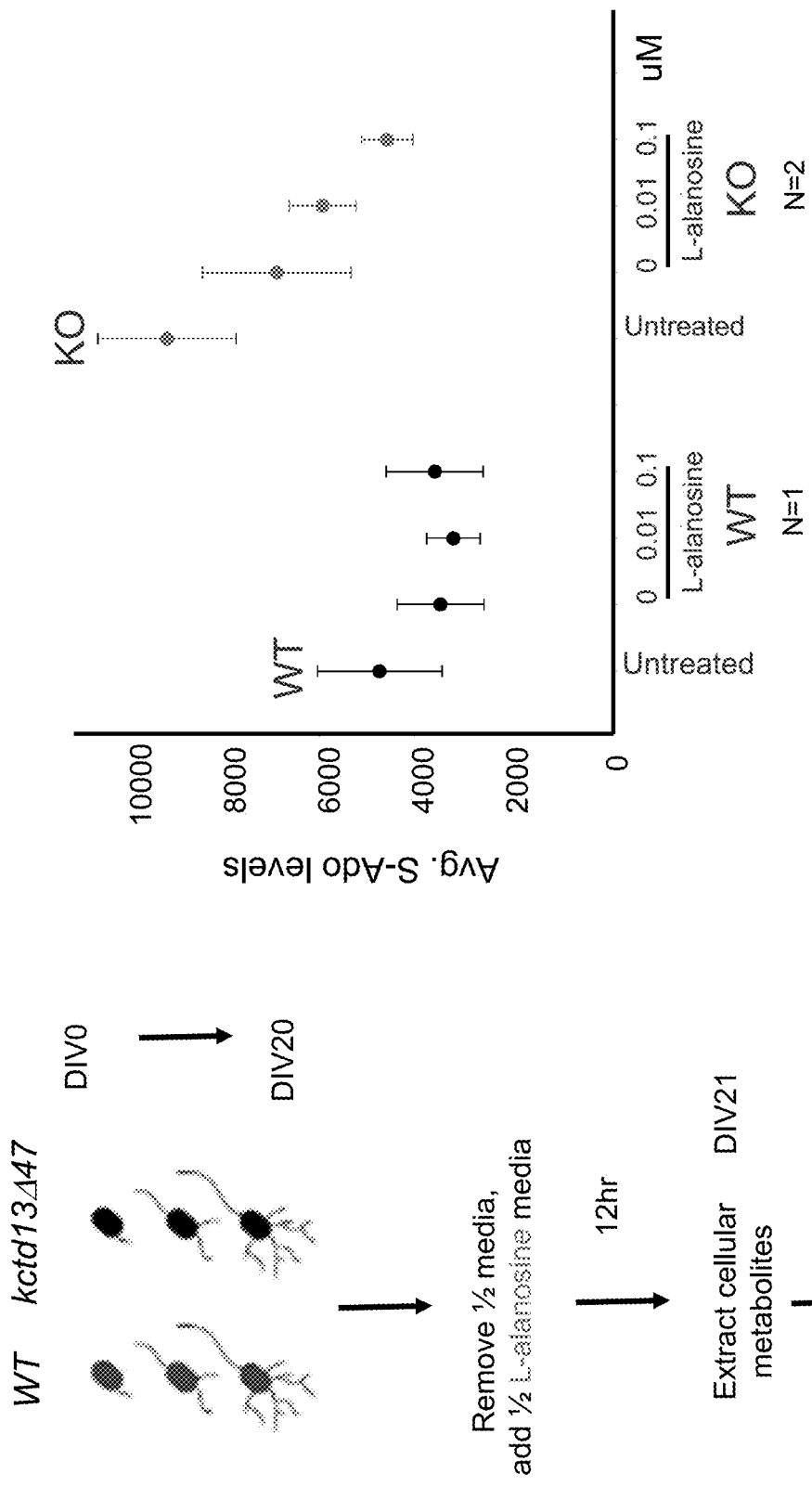
FIG. 22 shows S-Ado levels in cultured neurons from wild-type and Kctd13Δ47 (KO) mice contacted with 0, 0.01, or 0.1 µM L-alanosine.

In addition, S-Ado levels decreased in cultured neurons from kctd13Δ47 mice contacted with increasing concentrations of L-alanosine (FIG. 22).

It can also be determined whether exogenous expression of KCTD13 by viral transduction can rescue purine levels in 16p11.2 deletion patient fibroblasts to levels more similar to control fibroblasts. Transduction of a virus encoding KCTD13 is compared to a vector virus for the ability to rescue the purine phenotype of 16p11.2 deletion patient fibroblasts and make the profile more similar to that of wildtype fibroblasts, these changes include a reduction in AMP levels, S-AMP levels and S-Ado levels. In addition, changes in the metabolic profile of kctd13Δ47 neurons is evaluated following transduction with a virus encoding KCTD13 compared to a vector virus. These data confirm the specific role of KCTD13 in regulating purine levels.

The foregoing written specification should enable one skilled in the art to practice embodiments within the scope of the appended claims. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

TABLE OF SEQUENCES

| SEQ ID NO | Description | Sequence |
|---|---|---|
| 1 | sgRNA1 | gccggctgcggccgaatgct |
| 2 | sgRNA2 | aggggcttcagactgtacga |
| 3 | sgRNA3 | caccacgctgcgcaccctca |
| 4 | Kctd13 forward primer 1 | cggagtagct gtggagagtg g |

TABLE OF SEQUENCES

| SEQ ID NO | Description | Sequence |
|---|---|---|
| 5 | Kctd13 reverse primer 1 | AAAAAAAGCA CCGACTCGGT GCCACTTTTT CAAGTTGATA Acggactagc cttattttaa cttgCTATTT CTAGCTCTAA AACagcattc ggccgcagcc ggcggtgTTT CGTCCTTTCC ACaag |
| 6 | Kctd13 reverse primer 2 | AAAAAAAGCA CCGACTCGGT GCCACTTTTT CAAGTTGATA Acggactagc cttattttaa cttgCTATTT CTAGCTCTAA AACtcgtaca gtctgaagcc cctCggtgTT TCGTCCTTTC CACaag |
| 7 | Kctd13 reverse primer 3 | AAAAAAAGCA CCGACTCGGT GCCACTTTTT CAAGTTGATA Acggactagc cttattttaa cttgCTATTT CTAGCTCTAA AACtgagggt gcgcagcgtg gtgCggtgTT TCGTCCTTTC CACaag |
| 8 | Reverse sgRNA IVT primer 1 | Aaaaaagcac cgactcggtg ccactttttc aagttgataa cggactagcc ttattttaac ttgctatttc tagctctaaa acagcattcg gccgcagccg gcccwww wwww wwww wwww wwww wwww wwww |
| 8 | Reverse sgRNA IVT primer 1 | Aaaaaagcac cgactcggtg ccactttttc aagttgataa cggactagcc ttattttaac ttgctatttc tagctctaaa acagcattcg gccgcagccg gcccta tagt gagtcgtatt a |
| 9 | Reverse sgRNA IVT primer 2 | Aaaaaagcac cgactcggtg ccactttttc aagttgataa cggactagcc ttattttaac ttgctatttc tagctctaaa actcgtacag tctgaagccc tccctatag tgagtcgtat ta |
| 10 | Reverse sgRNA IVT primer 3 | Aaaaaagcac cgactcggtg ccactttttc aagttgataa cggactagcc ttattttaac ttgctatttc tagctctaaa actgagggtg cgcagcgtgg tgccctatag tgAgtcgtat ta |
| 11 | C-terminal peptide of KCTD13 | CVRRHITHDERPHGQQIVFKD |
| 12 | Human adenylosuccinate synthetase (ADSS, isozyme 2) | MAFAETYPAA SSLPNGDCGR PRARPGGNRV TVVLGAQWGD EGKGKVVDLL AQDADIVCRC QGGNNAGHTV VVDSVEYDFH LLPSGIINPN VTAFIGNGVV IHLPGLFEEA EKNVQKGKGL EGWEKRLIIS DRAHIVFDPH QAADGIQEQQ RQEQAGKNLG TTKKGIGPVY SSKAARSGLR MCDLVSDFDG FSERFKVLAN QYKSIYPTLE IDIEGELQKL KGYMEKIKPM VRDGVYFLYE ALHGPPKKIL VEGANAALLD IDFGTYPFVT SSNCTVGGVC TGLGMPPQNV GEVYGVVKAY TTRVGIGAFP TEQDNEIGEL LQTRGREFGV TTGRKRRCGW LDLVLLKYAH MINGFTALAL TKLDILDMFT EIKVGVAYKL DGEIIPHIPA NQEVLNKVEV QYKTLPGWNT DISNARAFKE LPVNAQNYVR FIEDELQIPV KWIGVGKSRE SMIQLF |
| 13 | Human adenylosuccinate lyase (ADSL) | MAAGGDHGSP DSYRSPLASR YASPEMCFVF SDRYKFRTWR QLWLWLAEAE QTLGLPITDE QIQEMKSNLE NIDFKMAAEE EKRLRHDVMA HVHTFGHCCP KAAGIIHLGA TSCYVGDNTD LIILRNALDL LLPKLARVIS RLADFAKERA SLPTLGFTHF QPAQLTTVGK RCCLWIQDLC MDLQNLKRVR DDLRFRGVKG TTGTQASFLQ LFEGDDHKVE QLDKMVTEKA GFKRAFIITG QTYTRKVDIE VLSVLASLGA SVHKICTDIR LLANLKEMEE PFEKQQIGSS AMPYKRNPMR SERCCSLARH LMTLVMDPLQ TASVQWFERT LDDSANRRIC LAEAFLTADT ILNTLQNISE GLVVYPKVIE RRIRQELPFM ATENIIMAMV KAGGSRQDCH EKIRVLSQQA ASVVKQEGGD NDLIERIQVD AYFSPIHSQL DHLLDPSSFT GRASQQVQRF LEEEVYPLLK PYESVMKVKA ELCL |
| 17 | AMP kinase subunit alpha-1 | MRRLSSWRKM ATAEKQKHDG RVKIGHYILG DTLGVGTFGK VKVGKHELTG HKVAVKILNR QKIRSLDVVG KIRREIQNLK LFRHPHIIKL YQVISTPSDI FMVMEYVSGG ELFDYICKNG RLDEKESRRL FQQILSGVDY CHRHMVVHRD LKPENVLLDA HMNAKIADFG LSNMMSDGEF LRTSCGSPNY AAPEVISGRL YAGPEVDIWS SGVILYALLC GTLPFDDDHV PTLFKKICDG IFYTPQYLNP SVISLLKHML QVDPMKRATI KDIREHEWFK QDLPKYLFPE DPSYSSTMID DEALKEVCEK FECSEEEVLS CLYNRNHQDP LAVAYHLIID NRRIMNEAKD FYLATSPPDS FLDDHHLTRP HPERVPFLVA ETPRARHTLD ELNPQKSKHQ GVRKAKWHLG IRSQSRPNDI MAEVCRAIKQ LDYEWKVVNP YYLRVRRKNP VTSTYSKMSL QLYQVDSRTY LLDFRSIDDE ITEAKSGTAT PQRSGSVSNY RSCQRSDSDA EAQGKSSEVS LTSSVTSLDS SPVDLTPRPG SHTIEFFEMC ANLIKILAQ |
| 18 | AMP kinase subunit beta-1 | MGNTSSERAA LERHGGHKTP RRDSSGGTKD GDRPKILMDS PEDADLFHSE EIKAPEKEEF LAWQHDLEVN DKAPAQARPT VFRWTGGGKE VYLSGSFNNW SKLPLTRSHN NFVAILDLPE GEHQYKFFVD GQWTHDPSEP IVTSQLGTVN NIIQVKKTDF |

TABLE OF SEQUENCES

| SEQ ID NO | Description | Sequence |
|---|---|---|
| | | EVFDALMVDS QKCSDVSELS SSPPGPYHQE PYVCKPEERF |
| | | RAPPILPPHL LQVILNKDTG ISCDPALLPE PNHVMLNHLY |
| | | ALSIKDGVMV LSATHRYKKK YVTTLLYKPI |
| 19 | AMP kinase subunit gamma-1 | METVISSDSS PAVENEHPQE TPESNNSVYT SFMKSHRCYD |
| | | LIPTSSKLVV FDTSLQVKKA FFALVTNGVR AAPLWDSKKQ |
| | | SFVGMLTITD FINILHRYYK SALVQIYELE EHKIETWREV |
| | | YLQDSFKPLV CISPNASLFD AVSSLIRNKI HRLPVIDPES |
| | | GNTLYILTHK RILKFLKLFI TEFPKPEFMS KSLEELQIGT |
| | | YANIAMVRTT TPVYVALGIF VQHRVSALPV VDEKGRVVDI |
| | | YSKFDVINLA AEKTYNNLDV SVTKALQHRS HYFEGVLKCY |
| | | LHETLETIIN RLVEAEVHRL VVVDENDVVK GIVSLSDILQ |
| | | ALVLTGGEKK P |

What is claimed is:

1. A method of treating an autism spectrum disorder comprising administering to a subject in need thereof an adenylosuccinate synthetase (ADSS) inhibitor that is a peptide or a small molecule.

2. The method of claim 1, wherein the ADSS inhibitor is a peptide comprising L-aspartate or L-aspartate mimic.

3. The method of claim 2, wherein the ADSS inhibitor is a peptide.

4. The method of claim 1, wherein the ADSS inhibitor is a small molecule.

5. The method of claim 4, wherein the small molecule is selected from L-aspartate, L-aspartate mimic, L-alanosine, D,L-alanosine, hydantocidin, hydantocidin phosphate, hydantocidin-hadacidin S hybrid inhibitor, hydantocidin-hadacidin R hybrid inhibitor, AdSS-1, AdSS-2, GE-101, GE-109, and hadacidin.

6. The method of claim 4, wherein the ADSS inhibitor is a compound having structure A:

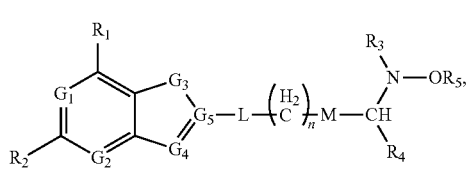

A wherein each of $R_1$ and $R_2$ is independently selected from the group consisting of —H, a halogen, —$NH_2$, —OH, —NH—$R_3$, and —O—$R_3$;

each of $G_1$, $G_2$, and $G_4$, is independently selected from the group consisting of CH, N, O, and S, or $G_4$ is independently CO=group;

$G_3$ is independently selected from the group consisting of $CH_2$, NH, O, CO=O group and S;

$G_5$ is independently selected from the group consisting of C and N;

L is absent or is selected from the group consisting of O, NH, and S;

$R_3$ is selected from a group consisting of —H, an $C_1$-$C_{18}$ alkyl, an aryl, —C(O)—H, and —C(O)-alkyl;

$R_4$ is selected from a group consisting of —H, —C(O) O—; and —C(O)—$R_3$;

$R_5$ is selected from a group consisting of —H, an $C_1$-$C_{18}$ alkyl, and an aryl;

M is absent or is selected from the group consisting of —$CH_2$—; —NH—; —NH—C(O)—; —O—, and —S—; and n is an integer having the value between 1 and 6.

7. The method of claim 6, wherein G1, G2, and G4 are N, G3 is NH, and G5 is C.

* * * * *

UNITED STATES PATENT AND TRADEMARK OFFICE
CERTIFICATE OF CORRECTION

| | |
|---|---|
| PATENT NO. | : 11,273,161 B2 |
| APPLICATION NO. | : 16/438790 |
| DATED | : March 15, 2022 |
| INVENTOR(S) | : Jon Madison and Jeffrey Cottrell |

It is certified that error appears in the above-identified patent and that said Letters Patent is hereby corrected as shown below:

In the Claims

Column 60
Line 45, delete "CO=O" and insert --C=O--

Signed and Sealed this
Twenty-eighth Day of June, 2022

*Katherine Kelly Vidal*

Katherine Kelly Vidal
*Director of the United States Patent and Trademark Office*

SEQUENCE LISTING

<160> NUMBER OF SEQ ID NOS: 19

<210> SEQ ID NO 1
<211> LENGTH: 20
<212> TYPE: DNA
<213> ORGANISM: Artificial Sequence
<220> FEATURE:
<223> OTHER INFORMATION: sgRNA1 designed for Kctd13

<400> SEQUENCE: 1
gccggctgcg gccgaatgct                                              20

<210> SEQ ID NO 2
<211> LENGTH: 20
<212> TYPE: DNA
<213> ORGANISM: Artificial Sequence
<220> FEATURE:
<223> OTHER INFORMATION: sgRNA2 designed for Kctd13

<400> SEQUENCE: 2
aggggcttca gactgtacga                                              20

<210> SEQ ID NO 3
<211> LENGTH: 20
<212> TYPE: DNA
<213> ORGANISM: Artificial Sequence
<220> FEATURE:
<223> OTHER INFORMATION: sgRNA3 designed for Kctd13

<400> SEQUENCE: 3
caccacgctg cgcaccctca                                              20

<210> SEQ ID NO 4
<211> LENGTH: 21
<212> TYPE: DNA
<213> ORGANISM: Artificial Sequence
<220> FEATURE:
<223> OTHER INFORMATION: Kctd13 forward primer 1

<400> SEQUENCE: 4
cggagtagct gtggagagtg g                                            21

<210> SEQ ID NO 5
<211> LENGTH: 125
<212> TYPE: DNA

```
<213> ORGANISM: Artificial Sequence
<220> FEATURE:
<223> OTHER INFORMATION: Kctd13 reverse primer 1

<400> SEQUENCE: 5
aaaaaaagca ccgactcggt gccactttt caagttgata acggactagc cttatttaa      60 cttgctattt ctagctctaa aacagcattc ggccgcagcc ggcggtgttt cgtcctttcc   120
acaag                                                                125

<210> SEQ ID NO 6
<211> LENGTH: 126
<212> TYPE: DNA
<213> ORGANISM: Artificial Sequence
<220> FEATURE:
<223> OTHER INFORMATION: Kctd13 reverse primer 2

<400> SEQUENCE: 6
aaaaaaagca ccgactcggt gccactttt caagttgata acggactagc cttatttaa      60 cttgctattt ctagctctaa aactcgtaca gtctgaagcc cctcggtgtt tcgtcctttc   120
cacaag                                                               126

<210> SEQ ID NO 7
<211> LENGTH: 126
<212> TYPE: DNA
<213> ORGANISM: Artificial Sequence
<220> FEATURE:
<223> OTHER INFORMATION: Kctd13 reverse primer 3

<400> SEQUENCE: 7
aaaaaaagca ccgactcggt gccactttt caagttgata acggactagc cttatttaa      60 cttgctattt ctagctctaa aactgagggt gcgcagcgtg gtgcggtgtt tcgtcctttc   120
cacaag                                                               126

<210> SEQ ID NO 8
<211> LENGTH: 121
<212> TYPE: DNA
<213> ORGANISM: Artificial Sequence
<220> FEATURE:
<223> OTHER INFORMATION: Reverse sgRNA IVT primer 1

<400> SEQUENCE: 8
aaaaaagcac cgactcggtg ccacttttc aagttgataa cggactagcc ttattttaac     60
ttgctatttc tagctctaaa acagcattcg gccgcagccg ccctatagt gagtcgtatt   120 a                                                                    121

<210> SEQ ID NO 9
<211> LENGTH: 122
<212> TYPE: DNA
<213> ORGANISM: Artificial Sequence
<220> FEATURE:
<223> OTHER INFORMATION: Reverse sgRNA IVT primer 2

<400> SEQUENCE: 9
aaaaaagcac cgactcggtg ccacttttc aagttgataa cggactagcc ttattttaac     60
ttgctatttc tagctctaaa actcgtacag tctgaagccc ctccctatag tgagtcgtat   120
ta                                                                   122

<210> SEQ ID NO 10
<211> LENGTH: 122
```

```
<212> TYPE: DNA
<213> ORGANISM: Artificial Sequence
<220> FEATURE:
<223> OTHER INFORMATION: Reverse sgRNA IVT primer 3

<400> SEQUENCE: 10
aaaaaagcac cgactcggtg ccacttttc aagttgataa cggactagcc ttattttaac    60
ttgctatttc tagctctaaa actgagggtg cgcagcgtgg tgccctatag tgagtcgtat   120
ta                                                                  122

<210> SEQ ID NO 11
<211> LENGTH: 21
<212> TYPE: PRT
<213> ORGANISM: Artificial Sequence
<220> FEATURE:
<223> OTHER INFORMATION: C-terminal peptide of KCTD13

<400> SEQUENCE: 11

Cys Val Arg Arg His Ile Thr His Asp Glu Arg Pro His Gly Gln Gln
1               5                   10                  15

Ile Val Phe Lys Asp
            20

<210> SEQ ID NO 12
<211> LENGTH: 456
<212> TYPE: PRT
<213> ORGANISM: Homo sapiens

<400> SEQUENCE: 12

Met Ala Phe Ala Glu Thr Tyr Pro Ala Ala Ser Ser Leu Pro Asn Gly
1               5                   10                  15

Asp Cys Gly Arg Pro Arg Ala Arg Pro Gly Gly Asn Arg Val Thr Val
                20                  25                  30

Val Leu Gly Ala Gln Trp Gly Asp Glu Gly Lys Gly Lys Val Val Asp
            35                  40                  45

Leu Leu Ala Gln Asp Ala Asp Ile Val Cys Arg Cys Gln Gly Gly Asn
        50                  55                  60

Asn Ala Gly His Thr Val Val Val Asp Ser Val Glu Tyr Asp Phe His
65                  70                  75                  80

Leu Leu Pro Ser Gly Ile Ile Asn Pro Asn Val Thr Ala Phe Ile Gly
                85                  90                  95

Asn Gly Val Val Ile His Leu Pro Gly Leu Phe Glu Glu Ala Glu Lys
                100                 105                 110

Asn Val Gln Lys Gly Lys Gly Leu Glu Gly Trp Glu Lys Arg Leu Ile
            115                 120                 125

Ile Ser Asp Arg Ala His Ile Val Phe Asp Phe His Gln Ala Ala Asp
        130                 135                 140

Gly Ile Gln Glu Gln Gln Arg Gln Glu Gln Ala Gly Lys Asn Leu Gly
145                 150                 155                 160

Thr Thr Lys Lys Gly Ile Gly Pro Val Tyr Ser Ser Lys Ala Ala Arg
                165                 170                 175

Ser Gly Leu Arg Met Cys Asp Leu Val Ser Asp Phe Asp Gly Phe Ser
                180                 185                 190

Glu Arg Phe Lys Val Leu Ala Asn Gln Tyr Lys Ser Ile Tyr Pro Thr
            195                 200                 205

Leu Glu Ile Asp Ile Glu Gly Glu Leu Gln Lys Leu Lys Gly Tyr Met
        210                 215                 220
```

```
Glu Lys Ile Lys Pro Met Val Arg Asp Gly Val Tyr Phe Leu Tyr Glu
225                 230                 235                 240

Ala Leu His Gly Pro Pro Lys Lys Ile Leu Val Glu Gly Ala Asn Ala
            245                 250                 255

Ala Leu Leu Asp Ile Asp Phe Gly Thr Tyr Pro Phe Val Thr Ser Ser
            260                 265                 270

Asn Cys Thr Val Gly Val Cys Thr Gly Leu Gly Met Pro Pro Gln
        275                 280                 285

Asn Val Gly Glu Val Tyr Gly Val Val Lys Ala Tyr Thr Thr Arg Val
    290                 295                 300

Gly Ile Gly Ala Phe Pro Thr Glu Gln Asp Asn Glu Ile Gly Glu Leu
305                 310                 315                 320

Leu Gln Thr Arg Gly Arg Glu Phe Gly Val Thr Thr Gly Arg Lys Arg
                325                 330                 335

Arg Cys Gly Trp Leu Asp Leu Val Leu Leu Lys Tyr Ala His Met Ile
                340                 345                 350

Asn Gly Phe Thr Ala Leu Ala Leu Thr Lys Leu Asp Ile Leu Asp Met
            355                 360                 365

Phe Thr Glu Ile Lys Val Gly Val Ala Tyr Lys Leu Asp Gly Glu Ile
370                 375                 380

Ile Pro His Ile Pro Ala Asn Gln Glu Val Leu Asn Lys Val Glu Val
385                 390                 395                 400

Gln Tyr Lys Thr Leu Pro Gly Trp Asn Thr Asp Ile Ser Asn Ala Arg
                405                 410                 415

Ala Phe Lys Glu Leu Pro Val Asn Ala Gln Asn Tyr Val Arg Phe Ile
            420                 425                 430

Glu Asp Glu Leu Gln Ile Pro Val Lys Trp Ile Gly Val Gly Lys Ser
            435                 440                 445

Arg Glu Ser Met Ile Gln Leu Phe
            450                 455

<210> SEQ ID NO 13
<211> LENGTH: 484
<212> TYPE: PRT
<213> ORGANISM: Homo sapiens

<400> SEQUENCE: 13

Met Ala Ala Gly Gly Asp His Gly Ser Pro Asp Ser Tyr Arg Ser Pro
1               5                   10                  15

Leu Ala Ser Arg Tyr Ala Ser Pro Glu Met Cys Phe Val Phe Ser Asp
            20                  25                  30

Arg Tyr Lys Phe Arg Thr Trp Arg Gln Leu Trp Leu Trp Leu Ala Glu
        35                  40                  45

Ala Glu Gln Thr Leu Gly Leu Pro Ile Thr Asp Glu Gln Ile Gln Glu
    50                  55                  60

Met Lys Ser Asn Leu Glu Asn Ile Asp Phe Lys Met Ala Ala Glu Glu
65                  70                  75                  80

Glu Lys Arg Leu Arg His Asp Val Met Ala His Val His Thr Phe Gly
                85                  90                  95

His Cys Cys Pro Lys Ala Ala Gly Ile Ile His Leu Gly Ala Thr Ser
            100                 105                 110

Cys Tyr Val Gly Asp Asn Thr Asp Leu Ile Ile Leu Arg Asn Ala Leu
        115                 120                 125

Asp Leu Leu Leu Pro Lys Leu Ala Arg Val Ile Ser Arg Leu Ala Asp
    130                 135                 140
```

Phe Ala Lys Glu Arg Ala Ser Leu Pro Thr Leu Gly Phe Thr His Phe
145                 150                 155                 160

Gln Pro Ala Gln Leu Thr Thr Val Gly Lys Arg Cys Cys Leu Trp Ile
            165                 170                 175

Gln Asp Leu Cys Met Asp Leu Gln Asn Leu Lys Arg Val Arg Asp Asp
            180                 185                 190

Leu Arg Phe Arg Gly Val Lys Gly Thr Thr Gly Thr Gln Ala Ser Phe
        195                 200                 205

Leu Gln Leu Phe Glu Gly Asp Asp His Lys Val Glu Gln Leu Asp Lys
    210                 215                 220

Met Val Thr Glu Lys Ala Gly Phe Lys Arg Ala Phe Ile Ile Thr Gly
225                 230                 235                 240

Gln Thr Tyr Thr Arg Lys Val Asp Ile Glu Val Leu Ser Val Leu Ala
                245                 250                 255

Ser Leu Gly Ala Ser Val His Lys Ile Cys Thr Asp Ile Arg Leu Leu
            260                 265                 270

Ala Asn Leu Lys Glu Met Glu Pro Phe Glu Lys Gln Gln Ile Gly
        275                 280                 285

Ser Ser Ala Met Pro Tyr Lys Arg Asn Pro Met Arg Ser Glu Arg Cys
290                 295                 300

Cys Ser Leu Ala Arg His Leu Met Thr Leu Val Met Asp Pro Leu Gln
305                 310                 315                 320

Thr Ala Ser Val Gln Trp Phe Glu Arg Thr Leu Asp Asp Ser Ala Asn
                325                 330                 335

Arg Arg Ile Cys Leu Ala Glu Ala Phe Leu Thr Ala Asp Thr Ile Leu
            340                 345                 350

Asn Thr Leu Gln Asn Ile Ser Glu Gly Leu Val Val Tyr Pro Lys Val
        355                 360                 365

Ile Glu Arg Arg Ile Arg Gln Glu Leu Pro Phe Met Ala Thr Glu Asn
    370                 375                 380

Ile Ile Met Ala Met Val Lys Ala Gly Gly Ser Arg Gln Asp Cys His
385                 390                 395                 400

Glu Lys Ile Arg Val Leu Ser Gln Gln Ala Ala Ser Val Val Lys Gln
                405                 410                 415

Glu Gly Gly Asp Asn Asp Leu Ile Glu Arg Ile Gln Val Asp Ala Tyr
            420                 425                 430

Phe Ser Pro Ile His Ser Gln Leu Asp His Leu Leu Asp Pro Ser Ser
        435                 440                 445

Phe Thr Gly Arg Ala Ser Gln Gln Val Gln Arg Phe Leu Glu Glu Glu
    450                 455                 460

Val Tyr Pro Leu Leu Lys Pro Tyr Glu Ser Val Met Lys Val Lys Ala
465                 470                 475                 480

Glu Leu Cys Leu

<210> SEQ ID NO 14
<211> LENGTH: 18
<212> TYPE: DNA
<213> ORGANISM: Artificial Sequence
<220> FEATURE:
<223> OTHER INFORMATION: Genotyping primer Kctd13 F 47_64nt

<400> SEQUENCE: 14
tccgctcact ggcatgtc                                                    18

```
<210> SEQ ID NO 15
<211> LENGTH: 18
<212> TYPE: DNA
<213> ORGANISM: Artificial Sequence
<220> FEATURE:
<223> OTHER INFORMATION: Genotyping primer Kctd13 R 47_64nt

<400> SEQUENCE: 15
cacactcgag gggctagg                                                 18

<210> SEQ ID NO 16
<211> LENGTH: 22
<212> TYPE: DNA
<213> ORGANISM: Artificial Sequence
<220> FEATURE:
<223> OTHER INFORMATION: Genotyping probe Kctd13 probe 47_64nt
<220> FEATURE:
<221> NAME/KEY: misc_feature
<222> LOCATION: (1)..(1)
<223> OTHER INFORMATION: 5'6-FAM fluorescent dye attached
<220> FEATURE:
<221> NAME/KEY: misc_feature
<222> LOCATION: (10)..(10)
<223> OTHER INFORMATION: ZEN quencher attached
<220> FEATURE:
<221> NAME/KEY: misc_feature
<222> LOCATION: (22)..(22)
<223> OTHER INFORMATION: 3IABkFQ quencher attached

<400> SEQUENCE: 16
tgcggccgaa tgcttggagt cc                                            22

<210> SEQ ID NO 17
<211> LENGTH: 559
<212> TYPE: PRT
<213> ORGANISM: Homo sapiens

<400> SEQUENCE: 17

Met Arg Arg Leu Ser Ser Trp Arg Lys Met Ala Thr Ala Glu Lys Gln
1               5                   10                  15

Lys His Asp Gly Arg Val Lys Ile Gly His Tyr Ile Leu Gly Asp Thr
            20                  25                  30

Leu Gly Val Gly Thr Phe Gly Lys Val Lys Val Gly Lys His Glu Leu
        35                  40                  45

Thr Gly His Lys Val Ala Val Lys Ile Leu Asn Arg Gln Lys Ile Arg
    50                  55                  60

Ser Leu Asp Val Val Gly Lys Ile Arg Arg Glu Ile Gln Asn Leu Lys
65                  70                  75                  80

Leu Phe Arg His Pro His Ile Ile Lys Leu Tyr Gln Val Ile Ser Thr
                85                  90                  95

Pro Ser Asp Ile Phe Met Val Met Glu Tyr Val Ser Gly Gly Glu Leu
            100                 105                 110

Phe Asp Tyr Ile Cys Lys Asn Gly Arg Leu Asp Glu Lys Glu Ser Arg
        115                 120                 125

Arg Leu Phe Gln Gln Ile Leu Ser Gly Val Asp Tyr Cys His Arg His
    130                 135                 140

Met Val Val His Arg Asp Leu Lys Pro Glu Asn Val Leu Leu Asp Ala
145                 150                 155                 160

His Met Asn Ala Lys Ile Ala Asp Phe Gly Leu Ser Asn Met Met Ser
                165                 170                 175

Asp Gly Glu Phe Leu Arg Thr Ser Cys Gly Ser Pro Asn Tyr Ala Ala
            180                 185                 190
```

```
Pro Glu Val Ile Ser Gly Arg Leu Tyr Ala Gly Pro Glu Val Asp Ile
            195                 200                 205

Trp Ser Ser Gly Val Ile Leu Tyr Ala Leu Leu Cys Gly Thr Leu Pro
210                 215                 220

Phe Asp Asp Asp His Val Pro Thr Leu Phe Lys Lys Ile Cys Asp Gly
225                 230                 235                 240

Ile Phe Tyr Thr Pro Gln Tyr Leu Asn Pro Ser Val Ile Ser Leu Leu
                245                 250                 255

Lys His Met Leu Gln Val Asp Pro Met Lys Arg Ala Thr Ile Lys Asp
            260                 265                 270

Ile Arg Glu His Glu Trp Phe Lys Gln Asp Leu Pro Lys Tyr Leu Phe
        275                 280                 285

Pro Glu Asp Pro Ser Tyr Ser Ser Thr Met Ile Asp Asp Glu Ala Leu
    290                 295                 300

Lys Glu Val Cys Glu Lys Phe Glu Cys Ser Glu Glu Val Leu Ser
305                 310                 315                 320

Cys Leu Tyr Asn Arg Asn His Gln Asp Pro Leu Ala Val Ala Tyr His
                325                 330                 335

Leu Ile Ile Asp Asn Arg Arg Ile Met Asn Glu Ala Lys Asp Phe Tyr
            340                 345                 350

Leu Ala Thr Ser Pro Pro Asp Ser Phe Leu Asp Asp His His Leu Thr
        355                 360                 365

Arg Pro His Pro Glu Arg Val Pro Phe Leu Val Ala Glu Thr Pro Arg
    370                 375                 380

Ala Arg His Thr Leu Asp Glu Leu Asn Pro Gln Lys Ser Lys His Gln
385                 390                 395                 400

Gly Val Arg Lys Ala Lys Trp His Leu Gly Ile Arg Ser Gln Ser Arg
                405                 410                 415

Pro Asn Asp Ile Met Ala Glu Val Cys Arg Ala Ile Lys Gln Leu Asp
            420                 425                 430

Tyr Glu Trp Lys Val Val Asn Pro Tyr Tyr Leu Arg Val Arg Arg Lys
        435                 440                 445

Asn Pro Val Thr Ser Thr Tyr Ser Lys Met Ser Leu Gln Leu Tyr Gln
    450                 455                 460

Val Asp Ser Arg Thr Tyr Leu Leu Asp Phe Arg Ser Ile Asp Asp Glu
465                 470                 475                 480

Ile Thr Glu Ala Lys Ser Gly Thr Ala Thr Pro Gln Arg Ser Gly Ser
                485                 490                 495

Val Ser Asn Tyr Arg Ser Cys Gln Arg Ser Asp Ser Asp Ala Glu Ala
            500                 505                 510

Gln Gly Lys Ser Ser Glu Val Ser Leu Thr Ser Ser Val Thr Ser Leu
        515                 520                 525

Asp Ser Ser Pro Val Asp Leu Thr Pro Arg Pro Gly Ser His Thr Ile
    530                 535                 540

Glu Phe Phe Glu Met Cys Ala Asn Leu Ile Lys Ile Leu Ala Gln
545                 550                 555

<210> SEQ ID NO 18
<211> LENGTH: 270
<212> TYPE: PRT
<213> ORGANISM: Homo sapiens

<400> SEQUENCE: 18

Met Gly Asn Thr Ser Ser Glu Arg Ala Ala Leu Glu Arg His Gly Gly
1               5                   10                  15
```

His Lys Thr Pro Arg Arg Asp Ser Ser Gly Gly Thr Lys Asp Gly Asp
              20                  25                  30

Arg Pro Lys Ile Leu Met Asp Ser Pro Glu Asp Ala Asp Leu Phe His
          35                  40                  45

Ser Glu Glu Ile Lys Ala Pro Glu Lys Glu Phe Leu Ala Trp Gln
 50                  55                  60

His Asp Leu Glu Val Asn Asp Lys Ala Pro Ala Gln Ala Arg Pro Thr
 65                  70                  75                  80

Val Phe Arg Trp Thr Gly Gly Lys Glu Val Tyr Leu Ser Gly Ser
              85                  90                  95

Phe Asn Asn Trp Ser Lys Leu Pro Leu Thr Arg Ser His Asn Asn Phe
             100                 105                 110

Val Ala Ile Leu Asp Leu Pro Glu Gly Glu His Gln Tyr Lys Phe Phe
             115                 120                 125

Val Asp Gly Gln Trp Thr His Asp Pro Ser Glu Pro Ile Val Thr Ser
 130                 135                 140

Gln Leu Gly Thr Val Asn Asn Ile Ile Gln Val Lys Lys Thr Asp Phe
145                 150                 155                 160

Glu Val Phe Asp Ala Leu Met Val Asp Ser Gln Lys Cys Ser Asp Val
             165                 170                 175

Ser Glu Leu Ser Ser Ser Pro Pro Gly Pro Tyr His Gln Glu Pro Tyr
             180                 185                 190

Val Cys Lys Pro Glu Glu Arg Phe Arg Ala Pro Pro Ile Leu Pro Pro
             195                 200                 205

His Leu Leu Gln Val Ile Leu Asn Lys Asp Thr Gly Ile Ser Cys Asp
 210                 215                 220

Pro Ala Leu Leu Pro Glu Pro Asn His Val Met Leu Asn His Leu Tyr
225                 230                 235                 240

Ala Leu Ser Ile Lys Asp Gly Val Met Val Leu Ser Ala Thr His Arg
             245                 250                 255

Tyr Lys Lys Lys Tyr Val Thr Thr Leu Leu Tyr Lys Pro Ile
             260                 265                 270

<210> SEQ ID NO 19
<211> LENGTH: 331
<212> TYPE: PRT
<213> ORGANISM: Homo sapiens

<400> SEQUENCE: 19

Met Glu Thr Val Ile Ser Ser Asp Ser Ser Pro Ala Val Glu Asn Glu
1               5                   10                  15

His Pro Gln Glu Thr Pro Glu Ser Asn Asn Ser Val Tyr Thr Ser Phe
              20                  25                  30

Met Lys Ser His Arg Cys Tyr Asp Leu Ile Pro Thr Ser Ser Lys Leu
          35                  40                  45

Val Val Phe Asp Thr Ser Leu Gln Val Lys Lys Ala Phe Phe Ala Leu
 50                  55                  60

Val Thr Asn Gly Val Arg Ala Ala Pro Leu Trp Asp Ser Lys Lys Gln
 65                  70                  75                  80

Ser Phe Val Gly Met Leu Thr Ile Thr Asp Phe Ile Asn Ile Leu His
              85                  90                  95

Arg Tyr Tyr Lys Ser Ala Leu Val Gln Ile Tyr Glu Leu Glu Glu His
             100                 105                 110

Lys Ile Glu Thr Trp Arg Glu Val Tyr Leu Gln Asp Ser Phe Lys Pro

-continued

```
              115                 120                 125
Leu Val Cys Ile Ser Pro Asn Ala Ser Leu Phe Asp Ala Val Ser Ser
    130                 135                 140
Leu Ile Arg Asn Lys Ile His Arg Leu Pro Val Ile Asp Pro Glu Ser
145                 150                 155                 160
Gly Asn Thr Leu Tyr Ile Leu Thr His Lys Arg Ile Leu Lys Phe Leu
                165                 170                 175
Lys Leu Phe Ile Thr Glu Phe Pro Lys Pro Glu Phe Met Ser Lys Ser
            180                 185                 190
Leu Glu Glu Leu Gln Ile Gly Thr Tyr Ala Asn Ile Ala Met Val Arg
        195                 200                 205
Thr Thr Thr Pro Val Tyr Val Ala Leu Gly Ile Phe Val Gln His Arg
    210                 215                 220
Val Ser Ala Leu Pro Val Val Asp Glu Lys Gly Arg Val Val Asp Ile
225                 230                 235                 240
Tyr Ser Lys Phe Asp Val Ile Asn Leu Ala Ala Glu Lys Thr Tyr Asn
                245                 250                 255
Asn Leu Asp Val Ser Val Thr Lys Ala Leu Gln His Arg Ser His Tyr
            260                 265                 270
Phe Glu Gly Val Leu Lys Cys Tyr Leu His Glu Thr Leu Glu Thr Ile
        275                 280                 285
Ile Asn Arg Leu Val Glu Ala Glu Val His Arg Leu Val Val Val Asp
    290                 295                 300
Glu Asn Asp Val Val Lys Gly Ile Val Ser Leu Ser Asp Ile Leu Gln
305                 310                 315                 320
Ala Leu Val Leu Thr Gly Gly Glu Lys Lys Pro
                325                 330
```